US011753644B2

(12) United States Patent
Kamme

(10) Patent No.: US 11,753,644 B2
(45) Date of Patent: Sep. 12, 2023

(54) COMPOUNDS AND METHODS FOR REDUCING IFNAR1 EXPRESSION

(71) Applicant: Ionis Pharmaceuticals, Inc., Carlsbad, CA (US)

(72) Inventor: Fredrik Carl Kamme, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 17/842,960

(22) Filed: Jun. 17, 2022

(65) Prior Publication Data

US 2023/0025910 A1 Jan. 26, 2023

Related U.S. Application Data

(60) Provisional application No. 63/212,454, filed on Jun. 18, 2021.

(51) Int. Cl.
*C12N 15/113* (2010.01)
*A61K 31/713* (2006.01)

(52) U.S. Cl.
CPC ........ *C12N 15/1138* (2013.01); *A61K 31/713* (2013.01); *C12N 15/1136* (2013.01); *C12N 2310/14* (2013.01); *C12N 2310/315* (2013.01); *C12N 2320/11* (2013.01)

(58) Field of Classification Search
CPC ............ C12N 15/1138; C12N 15/1136; C12N 2310/14; C12N 2310/315; C12N 2320/11; A61K 31/713
See application file for complete search history.

(56) References Cited

U.S. PATENT DOCUMENTS

| | | | |
|---|---|---|---|
| 3,687,808 | A | 8/1972 | Merigan et al. |
| 4,415,732 | A | 11/1983 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,725,677 | A | 2/1988 | Koster et al. |
| 4,845,205 | A | 7/1989 | Huynh Dinh et al. |
| 4,973,679 | A | 11/1990 | Caruthers et al. |
| 4,981,957 | A | 1/1991 | Lebleu et al. |
| 5,013,830 | A | 5/1991 | Ohutsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| RE34,036 | E | 8/1992 | McGeehan |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,188,897 | A | 2/1993 | Suhadolnik et al. |
| 5,194,599 | A | 3/1993 | Froehler et al. |
| 5,214,134 | A | 5/1993 | Weis et al. |
| 5,216,141 | A | 6/1993 | Benner |
| 5,220,007 | A | 6/1993 | Pederson et al. |
| 5,223,618 | A | 6/1993 | Cook et al. |
| 5,235,033 | A | 8/1993 | Summerton et al. |
| 5,256,775 | A | 10/1993 | Froehler |
| 5,264,423 | A | 11/1993 | Cohen et al. |
| 5,264,562 | A | 11/1993 | Matteucci |
| 5,264,564 | A | 11/1993 | Matteucci |
| 5,185,444 | A | 12/1993 | Summerton et al. |
| 5,276,019 | A | 1/1994 | Cohen et al. |
| 5,286,717 | A | 2/1994 | Cohen et al. |
| 5,319,080 | A | 6/1994 | Leumann |
| 5,321,131 | A | 6/1994 | Agrawal et al. |
| 5,359,044 | A | 10/1994 | Cook et al. |
| 5,366,878 | A | 11/1994 | Pederson et al. |
| 5,367,066 | A | 11/1994 | Urdea et al. |
| 5,378,825 | A | 1/1995 | Cook et al. |
| 5,386,023 | A | 1/1995 | Sanghvi et al. |
| 5,393,878 | A | 2/1995 | Leumann |
| 5,399,676 | A | 3/1995 | Froehler |
| 5,403,711 | A | 4/1995 | Walder et al. |
| 5,405,938 | A | 4/1995 | Sumerton et al. |
| 5,405,939 | A | 4/1995 | Suhadolnik et al. |
| 5,432,272 | A | 7/1995 | Benner |
| 5,434,257 | A | 7/1995 | Matteucci |
| 5,446,137 | A | 8/1995 | Maag et al. |
| 5,453,496 | A | 9/1995 | Caruthers et al. |
| 5,455,233 | A | 10/1995 | Spielvogel et al. |
| 5,457,187 | A | 10/1995 | Gmelner et al. |
| 5,457,191 | A | 10/1995 | Cook et al. |
| 5,459,255 | A | 10/1995 | Cook et al. |

(Continued)

FOREIGN PATENT DOCUMENTS

| | | |
|---|---|---|
| WO | WO 1996/023878 | 8/1996 |
| WO | WO 2004/045543 | 6/2004 |

(Continued)

OTHER PUBLICATIONS

International Search Report for PCT/US22/033936 dated Oct. 27, 2022.

(Continued)

*Primary Examiner* — J. E. Angell
(74) *Attorney, Agent, or Firm* — Sheppard Mullin

(57) ABSTRACT

Provided are oligomeric compounds, methods, and pharmaceutical compositions for reducing the amount or activity of IFNAR1 RNA in a cell or animal, and in certain instances reducing the amount of IFNAR1 protein in a cell or animal Such oligomeric compounds, methods, and pharmaceutical compositions are useful to treat diseases and conditions associated with neuroinflammation, including Aicardi-Goutières Syndrome, stroke, neuropsychiatric systemic lupus erythematosus, neuroinflammation following traumatic brain injury, neuro-autoimmune disorders, Alzheimer's disease, post-operative delirium and cognitive decline, cranial radiation-induced cognitive decline, viral infection-induced cognitive decline, neuromyelitis optica, and ataxia telangiectasia.

22 Claims, No Drawings

Specification includes a Sequence Listing.

(56) References Cited

U.S. PATENT DOCUMENTS

| | | | |
|---|---|---|---|
| 5,466,677 | A | 11/1995 | Baxter et al. |
| 5,466,786 | A | 11/1995 | Burh et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,489,677 | A | 2/1996 | Sanghvi et al. |
| 5,491,133 | A | 2/1996 | Walder et al. |
| 5,502,177 | A | 3/1996 | Matteucci et al. |
| 5,508,270 | A | 4/1996 | Baxter et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,711 | A | 6/1996 | Hawkins et al. |
| 5,527,899 | A | 6/1996 | Froehler |
| 5,536,821 | A | 7/1996 | Agrawal et al. |
| 5,541,306 | A | 7/1996 | Agrawal et al. |
| 5,541,307 | A | 7/1996 | Cook et al. |
| 5,550,111 | A | 8/1996 | Suhadolnik et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,350 | A | 10/1996 | Kmiec |
| 5,565,555 | A | 10/1996 | Froehler et al. |
| 5,567,811 | A | 10/1996 | Mistura et al. |
| 5,571,799 | A | 11/1996 | Tkachuk et al. |
| 5,576,427 | A | 11/1996 | Cook et al. |
| 5,587,361 | A | 12/1996 | Cook et al. |
| 5,587,469 | A | 12/1996 | Cook et al. |
| 5,587,470 | A | 12/1996 | Cook et al. |
| 5,591,722 | A | 1/1997 | Montgomery et al. |
| 5,594,121 | A | 1/1997 | Froehler et al. |
| 5,596,086 | A | 1/1997 | Matteucci |
| 5,596,091 | A | 1/1997 | Switzer |
| 5,597,909 | A | 1/1997 | Urdea et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,614,617 | A | 3/1997 | Cook et al. |
| 5,618,704 | A | 4/1997 | Sanghvi et al. |
| 5,623,065 | A | 4/1997 | Cook et al. |
| 5,623,070 | A | 4/1997 | Cook et al. |
| 5,625,050 | A | 4/1997 | Beaton et al. |
| 5,627,053 | A | 5/1997 | Usman et al. |
| 5,633,360 | A | 5/1997 | Bishofberger et al. |
| 5,639,873 | A | 6/1997 | Barascut et al. |
| 5,645,985 | A | 7/1997 | Froehler et al. |
| 5,646,265 | A | 7/1997 | McGee |
| 5,646,269 | A | 7/1997 | Matteucci |
| 5,652,355 | A | 7/1997 | Metelev et al. |
| 5,652,356 | A | 7/1997 | Agrawal |
| 5,663,312 | A | 9/1997 | Chaturvedula |
| 5,670,633 | A | 9/1997 | Cook et al. |
| 5,672,697 | A | 9/1997 | Buhr et al. |
| 5,677,437 | A | 10/1997 | Teng et al. |
| 5,677,439 | A | 10/1997 | Weis et al. |
| 5,681,941 | A | 10/1997 | Cook et al. |
| 5,698,685 | A | 12/1997 | Summerton et al. |
| 5,700,920 | A | 12/1997 | Altmann et al. |
| 5,700,922 | A | 12/1997 | Cook |
| 5,721,218 | A | 2/1998 | Froehler |
| 5,750,692 | A | 5/1998 | Cook et al. |
| 5,763,588 | A | 6/1998 | Matteucci et al. |
| 5,792,608 | A | 8/1998 | Swaminathan et al. |
| 5,792,847 | A | 8/1998 | Burh et al. |
| 5,801,154 | A | 9/1998 | Baracchini et al. |
| 5,808,027 | A | 9/1998 | Cook et al. |
| 5,830,653 | A | 11/1998 | Froehler et al. |
| 5,859,221 | A | 1/1999 | Cook et al. |
| 5,948,903 | A | 9/1999 | Cook et al. |
| 5,994,517 | A | 11/1999 | Ts'O |
| 6,005,087 | A | 12/1999 | Cook et al. |
| 6,005,096 | A | 12/1999 | Matteucci et al. |
| 6,166,199 | A | 12/2000 | Cook et al. |
| 6,300,319 | B1 | 10/2001 | Manoharan |
| 6,426,220 | B1 | 7/2002 | Bennett et al. |
| 6,525,191 | B1 | 2/2003 | Ramasamy |
| 6,531,584 | B1 | 3/2003 | Cook et al. |
| 6,582,908 | B2 | 6/2003 | Fodor et al. |
| 6,600,032 | B1 | 7/2003 | Manoharan et al. |
| 6,660,720 | B2 | 12/2003 | Manoharan |
| 6,770,748 | B2 | 8/2004 | Imanishi et al. |
| 7,015,315 | B1 | 3/2006 | Cook et al. |
| 7,053,207 | B2 | 5/2006 | Wengel et al. |
| 7,101,993 | B1 | 9/2006 | Cook et al. |
| 7,262,177 | B2 | 8/2007 | Ts'o et al. |
| 7,399,845 | B2 | 7/2008 | Seth et al. |
| 7,427,672 | B2 | 9/2008 | Imanishi et al. |
| 7,491,805 | B2 | 2/2009 | Vargeese et al. |
| 7,547,684 | B2 | 6/2009 | Seth et al. |
| 7,569,686 | B1 | 8/2009 | Bhat et al. |
| 7,666,854 | B2 | 2/2010 | Seth et al. |
| 7,691,997 | B2 | 4/2010 | Khvorova et al. |
| 7,696,345 | B2 | 4/2010 | Allerson et al. |
| 7,723,509 | B2 | 5/2010 | Manoharan et al. |
| 7,741,457 | B2 | 6/2010 | Swayze et al. |
| 7,750,131 | B2 | 7/2010 | Seth et al. |
| 7,875,733 | B2 | 1/2011 | Bhat et al. |
| 7,939,677 | B2 | 5/2011 | Bhat et al. |
| 8,022,193 | B2 | 9/2011 | Swayze et al. |
| 8,030,467 | B2 | 10/2011 | Seth et al. |
| 8,080,644 | B2 | 12/2011 | Wengel et al. |
| 8,088,746 | B2 | 1/2012 | Seth et al. |
| 8,088,904 | B2 | 1/2012 | Swayze et al. |
| 8,106,022 | B2 | 1/2012 | Manoharan et al. |
| 8,124,745 | B2 | 2/2012 | Allerson et al. |
| 8,153,365 | B2 | 4/2012 | Wengel et al. |
| 8,268,980 | B2 | 9/2012 | Seth et al. |
| 8,278,283 | B2 | 10/2012 | Seth et al. |
| 8,278,425 | B2 | 10/2012 | Prakash et al. |
| 8,278,426 | B2 | 10/2012 | Seth et al. |
| 8,440,803 | B2 | 5/2013 | Swayze et al. |
| 8,501,805 | B2 | 8/2013 | Seth et al. |
| 8,530,640 | B2 | 9/2013 | Seth et al. |
| 8,546,556 | B2 | 10/2013 | Seth et al. |
| RE44,779 | E | 2/2014 | Imanishi et al. |
| 8,828,956 | B2 | 9/2014 | Manoharan et al. |
| 9,005,906 | B2 | 4/2015 | Swayze et al. |
| 9,012,421 | B2 | 4/2015 | Migawa et al. |
| 9,127,276 | B2 | 8/2015 | Prakash et al. |
| 9,290,760 | B2 | 3/2016 | Rajeev et al. |
| 2001/0053519 | A1 | 12/2001 | Fodor et al. |
| 2003/0158403 | A1 | 8/2003 | Manoharan et al. |
| 2003/0175906 | A1 | 9/2003 | Manoharan et al. |
| 2003/0228597 | A1 | 12/2003 | Cowsert et al. |
| 2004/0171570 | A1 | 9/2004 | Allerson et al. |
| 2005/0130923 | A1 | 6/2005 | Bhat et al. |
| 2006/0148740 | A1 | 7/2006 | Platenburg |
| 2007/0031844 | A1 | 2/2007 | Khvorova et al. |
| 2008/0039618 | A1 | 2/2008 | Allerson et al. |
| 2010/0190837 | A1 | 7/2010 | Migawa et al. |
| 2010/0197762 | A1 | 8/2010 | Swayze et al. |
| 2013/0130378 | A1 | 5/2013 | Manoharan et al. |
| 2014/0107330 | A1 | 4/2014 | Freier et al. |
| 2015/0018540 | A1 | 1/2015 | Prakash et al. |
| 2015/0184153 | A1 | 7/2015 | Freier et al. |
| 2015/0191727 | A1 | 7/2015 | Migawa et al. |
| 2015/0267195 | A1 | 9/2015 | Seth et al. |
| 2015/0275212 | A1 | 10/2015 | Albaek et al. |
| 2015/0368338 | A1 | 12/2015 | Chi et al. |
| 2020/0199589 | A1 | 6/2020 | Kordasiewicz et al. |
| 2020/0399381 | A1 | 12/2020 | Cao et al. |

FOREIGN PATENT DOCUMENTS

| | | |
|---|---|---|
| WO | WO 2005/116204 | 12/2005 |
| WO | WO 2008/070137 | 6/2008 |
| WO | WO 2010/103292 | 9/2010 |
| WO | WO 2012/068636 | 5/2012 |
| WO | WO 2013/173637 | 11/2013 |
| WO | WO 2015/200165 | 12/2015 |
| WO | WO 2017/216390 | 12/2017 |
| WO | WO 2018/154412 | 8/2018 |

(56) References Cited

FOREIGN PATENT DOCUMENTS

| | | |
|---|---|---|
| WO | WO 2019/157531 | 8/2019 |
| WO | WO 2020/072991 | 4/2020 |
| WO | WO 2022/266415 | 12/2022 |

OTHER PUBLICATIONS

International Search Report for PCT/US22/033935 dated Nov. 4, 2022.
Adang et al., "Developmental outcomes of Aicardi Goutieres Syndrome" J Child Neuro (2020) 35: 7-16.
Akwa et al., "Transgenic Expression of IFN-α in the Central Nervous System of Mice Protects Against Lethal Neurotropic Viral Infection but Induces Inflammation and Neurodegeneration" J Immunol (1998) 161: 5016-5026.
Baruch et al., "Aging-induced type I interferon response at the choroid plexus negatively affects brain function" Science (2014) 346: 89-93.
Bialas et al. "Microglia-dependent synapse loss in type I interferon-mediated lupus" Nature (2017) 546: 539-543 [Retracted].
Blank et al., "Brain Endothelial- and Epithelial-Specific Interferon Receptor Chain 1 Drives Virus-Induced Sickness Behavior and Cognitive Impairment" Immunity (2016) 44: 901-912.
Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Cho et al., "Transcription modules in microglial gene expression regulation" Keystone Presentation (2017).
Crooke et al., "Basic Principles of Antisense Therapeutics" Antisense Research and Application (1998) Chapter 1:1-50.
Crooke, St., et al., "Antisense Drug Technology" Second Edition, CRC Press (2008) Chapters 1-28.
Crow et al., "Aicardi-Goutieres syndrome and the type I interferonopathies" Nature Reviews Immunology (2015) 1-12.
Crow et al., "Treatments in Aicardi-Goutieres syndrome" Developmental Medicine & Child Neurology (2019) 42-47.
Crow et al., "Targeting of Type I Interferon in Systemic Autoimmune Diseases" Trans Res (2015) 165: 296-305.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Gautschi et al., "Activity of a novel bcl-2/bcl-xLbispecific antisense oligonucleotide against tumors of diverse histologic origins" J. Natl. Cancer Inst. (2001) 93:463-471.
Goldmann et al., "Fine-tuning of type I IFN-signaling in microglia—implications for homeostasis, CNS autoimmunity and interferonopathies" Curr Opin in Neurobiol (2016) 36: 38-42.
Hartlova et al., "DNA damage primes the type I interferon system via the cytosolic DNA sensor STING to promote anti-microbial innate immunity" Immunity (2015) 42: 332-343.
Hofer et al., "Type I Interferon in neurological disease—The devil from within" Cytokine & Growth Factor Reviews (2013) 24: 257-267.
Hosseini et al., "Type I Interferon Receptor Signaling in Astrocytes Regulates Hippocampal Synaptic Plasticity and Cognitive Function of the Healthy CNS" Cell Reports (2020) 31: 1-21.
Kamme et al., "Modulation of Microglia In Vivo Using Antisense Oligonucleotides" Poster for 50th Meeting of the Winter Conference on Brain Research (WCBR) Big Sky Resort Convention Center (Big Sky, Montana USA) Jan. 28-Feb. 2, 2017.
Kamme et al., "Modulation of Microglia in vivo Using Antisense Oligonucleotides" Abstract for Poster in 50th Meeting of the Winter Conference on Brain Research (WCBR) Big Sky Resort Convention Center (Big Sky, Montana USA) Jan. 28-Feb. 2, 2017.
Karageorgas et al., "Activation of type I interferon pathway in systemic lupus erythematosus: association with distinct clinical phenotypes" J Biolmed Biotechnol (2011) 1-13.
Klok et al., "Interferon-α and the calcifying microangiopathy in Aicardi-Goutières syndrome" Ann Clin Transl Neurol (2015) 2: 774-779.
Li et al., "Type I interferon-regulated gene expression and signaling in murine mixed glial cells lacking signal transducers and activators of transcription 1 or 2 or interferon regulatory factor 9" J Biol Chem (2017) 292: 5845-5859.
Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.
Main et al., "Type-1 interferons contribute to the neuroinflammatory response and disease progression of the MPTP mouse model of Parkinson's disease" Glia (2016) 64: 1590-1604.
Main et al., "Type-I interferons mediate the neuroinflammatory response and neurotoxicity induced by rotenone" J Neurochem (2017) 141: 75-85.
McDonough et al., "Ischemia/Reperfusion Induces Interferon-Stimulated Gene Expression in Microglia" J Neurosci (2017) 37: 8292-8308.
Minter et al., "Deletion of the type-1 interferon receptor in APPswe/PS1e9 mice preserves cognitive function and alters glial phenotype" Acta Neuropathologica Communications (2016) 4:72, 1-23.
Morand et al., "Trial of Anifrolumab in Active Systemic Lupus Erythematosus" N Engl J Med (2020) 382: 211-221.
New England Biolabs 1998/99 Catalog (cover page and pp. 121 and 284).
Owens et al., "Interferons in the central nervous system: A few instruments play many tunes" Glia (2014) 62: 339-355.
Peng et al., "Molecular basis for antagonistic activity of anifrolumab, an anti-interferon-α receptor 1 antibody" MAbs (2015) 7: 428-439.
Reynolds et al., "Rational siRNA design for RNA interference" Nature Biotechnology (2004) 22(3):326-330.
Richards et al., "Neurodegenerative diseases have genetic hallmarks of autoinflammatory disease" Hum Mol Gen (2018) 27: R108-R118.
Rodero et al., "Type I interferon-mediated monogenic autoinflammation: The type I interferonopathies, a conceptual overview" J Exp Med (2016) 213: 2527-2538.
Roselli et al., "Interferons in Traumatic Brain and Spinal Cord Injury: Current Evidence for Translational Application" Front Neurol (2018) 9: 1-12.
Roy et al., "Type I interferon response drives neuroinflammation and synapse loss in Alzheimer disease" J Clin Invest. 2020, 130(4):1912-1930.
Sanghvi et al., "Heterocyclic Base Modifications in Nucleic Acids and Their Applications in Antisense Oligonucleotides" Antisense Research and Applications (1993) pp. 273-288.
Santer et al., "Potent induction of IFN-alpha and chemokines by autoantibodies in the cerebrospinal fluid of patients with neuropsychiatric lupus" J Immunol (2009) 182: 1192-1201.
Schmidt et al., "Type I interferon receptor signalling is induced during demyelination while its function for myelin damage and repair is redundant" Experimental Neurology (2009) 216: 306-311.
Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.
Singh et al., "A pivotal role for Interferon-a receptor-1 in neuronal injury induced by HIV-1" J of Neuroinflammation (2020) 17: 1-23.
Stetson et al., "Trex1 prevents cell-intrinsic initiation of autoimmunity" Cell (2008) 134: 587-598.
Takahashi et al., "Persistent interferon transgene expression by RNA interference-mediated silencing of interferon receptors" J Gene Med (2010) 12: 739-746.
Volpi et al., "Type I interferonopathies in pediatric rheumatology" Pediatric Rheumatology (2016) 14: 1-12.
Witcher et al., "Traumatic Brain Injury Causes Chronic Cortical Inflammation and Neuronal Dysfunction Mediated by Microglia" J Neurosci (2021) 41: 1597-1616.

(56) References Cited

OTHER PUBLICATIONS

Wlodarczyk et al., “Type I interferon-activated microglia are critical for neuromyelitis optica pathology” Glia (2021) 69: 943-953.
Woolf et al., “Specificity of antisense oligonucleotides in vivo” PNAS (1992) 89: 7305-7309.
Zeng et al., “Interferon-α exacerbates neuropsychiatric phenotypes in lupus-prone mice” Arthritis Res Ther (2019) 21: 1-11.

SEQUENCE LISTING

<160> NUMBER OF SEQ ID NOS: 15

<210> SEQ ID NO 1
<211> LENGTH: 42000
<212> TYPE: DNA
<213> ORGANISM: Homo sapiens

<400> SEQUENCE: 1
tttcaagata cataaattat acctctaaga tgtttttaaa ataggcatat ttcccctggg 60
cgtggtgact cacgcctgca atcccagcac tccgggaagc aaaggtgagc ggatcacttc 120
aggtcaggag ttccagacca gcctgggtaa cacagcggaa atcccatctc cactaaaaat 180

-continued

```
acaaaaacta gccgggcgca atagcgcaca gctgtaatct cagctactca ggaggctgaa    240
gcaggagaat cgcttgaacc cggaaggcgg aggttgtggt gagccgagat cgcgccactg    300
cactccagcc cgggtgacag agcaagactc cgattcgaac aatgcaatgg aatatataca    360
tatatgtata tatggaacat atatacatat gtggaacaaa tacatatatg gaacatacat    420
atgtggaaca aatacatata tggaacatac atatgtggaa ccaatacata tatggaacat    480
acatatgtgg aaccaataca tatatgcaac atacatatgt ggaaccaata catatatgca    540
acatatatat gtggaaccaa tacatatatg caacatatat atgtggaacc aatacatata    600
tgcaacatat atatgtggaa ccaatacata tatgcaacat atatatgtgg aaccaataca    660
tatatgcaac atatatatgt ggaaccaata catatatgca acatatatat gtggaaccaa    720
tacatatatg caacatatat atgtggaacc aatacatata tgcaacatat atatgtggaa    780
ccaatacata tatagaacat atatatgtgg aaccaatata tatggaacat acgtatgtgg    840
aacatacata tgtggaacat acgtatgtgg accatacata tgtggaacat acgtatgtgg    900
accatacata tgtggaacat acgtatgtgg accatacata tgtgaaacat acgtatgtcg    960
accatacgta tgggtcccat atacatatgg gacacatacg tatggaatat atatatggga   1020
cacatacgta tggaatatat acgtatatat acatatggga cacatacgta tggaatatac   1080
atatggaata tacatatatg ggacacataa gtatggaata tatacgtatg gaatatacac   1140
gcatggaata tatacgtatg gaatatatat gtatggaata tacacgtctg gaatatatat   1200
gtatggaata ttcacgtatg gaatatatat ctggaatata tatatatgga atatatatct   1260
ggaatatata tatggaatat atatctggaa tatatatata tggaatatat atctggaata   1320
tatatatatg gaatatatat ctggaatata tatatggaat atatatctgg aatatatata   1380
tatggaatat atatctggaa tatatatata tggaatatat atatggaata tatatatatg   1440
gaatatatat ggaatatata tatatggaat atatatatgc aatatacata tatggaatat   1500
atatatgcaa tatacatata tggaatacat atatgcaata tatatatgga atatatatat   1560
ggaatatata tatggaatat atatataata tatatacgga atatatatat acggaatata   1620
tatataatat atatacggaa tatatatata cggaatatat atataatata tatacggaat   1680
atatatatac ggaatatata tataatatat atataatata tatacggaat atatatatac   1740
ggaatatata tataatatat gtatggaata tatatatacg gaatatatat ataatatatg   1800
tatggaatat atatatacgg aatatatata taatatatgt atggaatata tatatacgga   1860
atagatatat aatatatgta tggaatatat atatacggaa tatatatata atatatatat   1920
atggcatata tacatggaat atatatatat ggaatatata catggaatat atatatatgg   1980
aatatataca tggaatatat atatatggaa tatatacatg gaatatatat atatggaata   2040
tatacatgga atatatatat atggaatata tacatggaat atatatatat ggcatatata   2100
catggaatat atatatatgg catatataca tggcatatat atatatggca tatatatata   2160
tggcatatat atatggcata tatatatatg gcatatatat atggcatata tatatatggc   2220
atatatatat ggcatatata tatatggcat atatatatgg catatatata tatggcatat   2280
atatatggca tatatatata tggcatatat atatggcata tatatatggc atatatatat   2340
ggcatatata tatggcatat atatatggct atagagatgg catatatata tggcatatag   2400
agatggcata tagagatggc atatagagat ggcatataga gatggcatat agagatggca   2460
tatagagatg gcatatagag atggcatata gagatggaat atagagatgg aatatatatg   2520
gcatatagag atggaatata tatggcatat agagatggaa tatatatggc atatagagat   2580
```

-continued

```
ggcatataga gatggaatat agagatggaa tatagagatg gaatagatat ggaatataga   2640
gatggaatag atatggaata tagagatgga atagagatgg aatatagaga tggaatatag   2700
agatgggata tagagatggg atatagagat gggatataga gatgggatat agagatggga   2760
tatagagatg ggatatagtg atggaatata gagatgggat atagagatgg aatagatatg   2820
gaatatagag atggaataga tatggaatat agagatggaa tagatatgga atatagagat   2880
ggaatataga gatgggatat agagatggga tatagagatg gaatatagag atgggatata   2940
gagatggaat atagagatgg gatatagaga tggaatatag tgatgggata tagagatgga   3000
atatatagat ggaatataga gatggaatat atagatggaa tacatatata ttccattgca   3060
ttgttcttta caaacattca tttaattatg taattgctaa ttaattgctt ggttgttata   3120
acaacgaagt atttgattcc ttattttatc tcatcattta aattttattt cgcatatttt   3180
cacaatgcac tggatctatt actgaggaat ttaattaaat aatcattcga accatgggct   3240
cgaattgttt actgataaag cccgacgacc aaaacagcct agcgactgct gtttggagcc   3300
cctcggccca gggcccgtgg ctgttctctc caagggacca tctcgcccct cagccaagtc   3360
gcccggaaaa cgagcgctcg accgcctctg ccccgctctc gctctgcaca cagcaacggt   3420
ctggtcgctc agccacttcc tccttccagc ctcatctggt tcccaggccg ctggggactc   3480
ccaacgccac tgtccaagac tctagggtca gcaagcgccc cgggcggaga agggcgagga   3540
cgaagagcgc cgggccgcga ccaggagccc acccgcgccc tccgactgca gacatgggga   3600
agagacgcgg gaactccaaa gtcgctgggt ctgcgcaggt gtgtgccgcg atcctgtgaa   3660
ggtcaaggcc tcctgtgagg gggagtcgtc ctggaatgcg atggtgaagt gctccagacc   3720
ggccataggc cggaaagagt gaggaagaag agaatgcagg aggcctgcga tttctaaggc   3780
gcgcgcgcac aggggtgctg caattaggat ggggcaatgg gagcttggag aaggggtgct   3840
agctaggagg aaaggcgcgt gcgtggagga acggcgcgtg cgcggagggg cggtgtgtgt   3900
gtcagaagag gcggcgcgtg cgtagagggg cggtgagagc taagaggggc agcgcgtgtg   3960
cagaggggcg gtgtgactta ggacggggcg atggcggctg agaggagctg cgcgtgcgcg   4020
aacatgtaac tggtgggatc tgcggcggct cccagatgat ggtcgtcctc ctgggcgcga   4080
cgaccctagt gctcgtcgcc gtggcgccat gggtgttgtc cgcagccgca ggtgagaggc   4140
ggggaggaga gtcttggcgc agggcgggag gtagggcacg cagctgggct acgggggcgg   4200
cgatgctgtt gggggcgaca gacgcccagt ctgggaaacc ttcggtccac tttgccgcgc   4260
caaagattaa acccgacctg ggctcgcaaa tcaaccagga gaaagtggtg ttctgggtcc   4320
tctcttgccg cttgcctgtg gccgtgtacg ggtcctcggg agcgcccggg tcccaccccc   4380
gtgaaatggc ggtgccagag ctttgtgtcg agtttgattc tttccgggaa agtaccgcgg   4440
ctccgctggt ctgtttgata ataaacaaaa catttcccga aatgcatttc ctcaatctgg   4500
tgaataggcg cccagtccca cgggggagtg agctaagtgt ggccaggatt tctctgccct   4560
caggattcat acaggccaat aaaaaatgac agtcggagtg actgaagcat aattgtcagt   4620
tctcgaggtt tactaagcct gcttcagggc gcatccggga aaaacgtgag ccacaaacac   4680
gtctgtgact ggttttccag aggttttcag gaggtggggc aggaaggcag taaggcaaat   4740
agttctgtga gaatttagtt agtgcccaag aaatctgtat tttaagatac catgagtgtc   4800
ttgaagagaa aaagagagta aagggagtca gttatgcaga tgcctctggg tagatggagt   4860
cttgactttg ttttgcacct gagaagataa gcttgtaatt gacatggtca gtgtggaagg   4920
cctgaactag tttttcagat taactttgga atgccatttg ttgagaggag aggtccattc   4980
```

-continued

```
acattgttgg ggggcttaga attttatttt tggtttactt aactacctac tttttttccca   5040
aagaaataat catgttcaaa actcaatgaa atgttatctc aatgagattg taatgttgct   5100
cagtctttca gaagtcataa aaatagtcat actttttaaa ctagtaaatg caattctagg   5160
acccaagact aagaaaactg tccaaaatat gggaagacat ttttatttat actttttttt   5220
tttttttttt gagacagcct gttgcccagg ctggtgtgca gaggcgtgat ctcagctcac   5280
tgcaacctct gcctcccagg ttcaggcgat tctcctgcct cagcctcttg agtagctgga   5340
attacaggtg cacgccacca catccggcta tttttgtat ttctagtaga gatggggttt   5400
tgccatgttg gccaggctgg tctcgaactc ctgacctcaa acaatccact tcagcctccc   5460
aaagtgctgg gattacaggt gtgagccacc acgcccgatc tatttatgtt ttagacttta   5520
gttttaggaa ctagacttag gttgtagacc tgaagttaca gttggcatcc ccttgtttat   5580
gggagaccag caaagaattg acttatgaat gatctgtcag ggtagccctt cgcagatggc   5640
tgagtctttt tatccttcct tggggatttg gctgaagcat aatgctagta acagccattc   5700
gtttggaaga gggtgttgca gtcacttggc ctctgggctt aactaacttc cctttttgcgt   5760
aagaaagttg ggagaggtcc tgagattttt tttttcttt tacaaaaata ataaaagaaa   5820
aatacaaagg cagggcgtca ccaggctaat ttgctgaaat tcttcatact tacttgggat   5880
gcatgggggga atggcaacta ttacaaggtt gatagagagt gagaggtaat tttgtagtga   5940
ggaggggtac ccaaagagaa tcagggctag catcccagtg caggagtcca ggtggtctgt   6000
gagcctgcaa gtgagttcaa aatactttac ctgttggctt aggaaaccat atacctgtgt   6060
ggtacatgat atcctatttc tcaaactttt ccacaaatat gtagtatact tttcctagga   6120
tgtgggtact agggtcctgg tgcatcccat agtaatttct ttgaagtctt ttgtttatga   6180
aaaacttgca ttaaactcat gtttggtttg atgtgaaaaa agctttccca gaattttcat   6240
ataaaattga cattccagga gggtgtgcat taagaaatta atttaaaatt aggttagcgg   6300
acaggtggca agatataatt tataggcatt tatcatttct taagctctta gctgtgtgcc   6360
aggcagtaat ctaagtgttt taaaggtata aactcattaa gctttcagag cagtgtagat   6420
actgttatgc ttagttaaca gacaaggaaa ctgagcaacg gagagatcaa gtaacttgcc   6480
tgaggctgta taggccagtc cgtggaggag tgggaagtca aatcctgagt ctggactaat   6540
agccttgggg cttaaccaga ctagactgtt ttcccaaagg ccaaacaatt taaattcctg   6600
attgtccact tgtatgttaa gggcctaatt atcagtatct ttcagttaac tgtgagccca   6660
aaaatatctg agaccggtct gaaatcaact tagaaagttt attttgccaa ggttaaggat   6720
gcattcatga cacagcctca agaggtcctg gccacatgtg cccaaggtgg tcaaggtcca   6780
gcttgctttt atacatttta gggagacata tcaatcagta catctaagat gtacatttga   6840
ttggttcgat ctggaaaggc aggacaactc aaagcaaggc ttccaggtca taggtagatt   6900
taaagatttt ctgattggta attggttgaa atcaatggaa aggaatgtct gggatgtcct   6960
aaggggttgt ggagaccaaa attttatcat gcagatcaag cttgtccaac ccacagccca   7020
ctggccgcgt gcagcccatg atggctttga atgcagtcca acacaaattc gtaaactttc   7080
ttaaaacatg aggggttttt gttttgtttg ttttctttct gtttttttgt ttgtttgttt   7140
ttagctcatc agatattgtt agtgtatttt gtgtgtggcc caagacagtt gttcttccag   7200
tgtggcccac ggaagcaaaa agagtggaca cccttgatgc agatgaggcc tgcagatagc   7260
aggcttcaga gagaatagat tgtaactgtt tcttgtgaaa cttaacgtct gtgttgttgt   7320
taatggtggt tagcttttttc tgaattccag aagagaggag ggtataatga ggcatatcca   7380
```

aacctcactt cgcatcatgg cctgaagtag tttttcaggt tagctttgga atgcccttgg 7440
tcaggagaag gggtccattc tgatggttgg gggacttaga attttatttt tggtttacgt 7500
aactatctac tttttcccca aaaaaaatca tgttgaaaac tcaagacctt aagtttacag 7560
ctcaagctga tcctgaaagt tatctcagtg agattgtaat gttgctcagt ctttcagaag 7620
ttgtataaat gtacctttta gcctagtaaa tgcaattcta ggactctaga ttaagaaaac 7680
tatccaaaat atgggaagac atttacttac atatttgtac agatatctat atttggattt 7740
atgtcagact taaagatata gtaaaccatt ttggtcgtga aaatgaatgt gaaaggttga 7800
aagcaaccaa aattataaat gcattatata tatattagat taaatgtcca tttatacatt 7860
tacatgtggg gtaattaatt gttaatatac taatataaaa cattttaata tactagtaaa 7920
ttaatatatt gtatgttaat gttacataac aatttatgaa aaaattatta aaaggagatt 7980
gccaataata atagagcaaa atctgtgaaa actaaaatcc tgtttaataa ctttatttcc 8040
aagcccctgt ccatttatca gtcagttatt tgttggtctt ccaaatgcca acatgcctgt 8100
aacttcaggg tctccttctt ttagcagtaa aggatttttt ttctccctga ggaaatcact 8160
agctgtaccc tataacattt tctattcttg tctcaaggcc caaaattact agaattataa 8220
tattctgcac aagatattgt aaatactaca aatgccatca gatcttttgt taaactctgt 8280
aaacccagtt gctacccttt ggctgcatag aatctataaa ttctaacaaa tggatgagaa 8340
ccaagttaag aattctagag tgggataagg ggatgtgatg tattctattc agggatgaag 8400
ttttagagac tccaagtatg aaacagaaaa ttgaggatgg ggagacctga tgggtaccac 8460
attaagttta aaaaaaaaaa aagtgtttc tcagctgtct ccccttttga ccccatacta 8520
taagatctaa ctggaaagag caagaagctg tctcagttaa gaaagttcta tacaagaacc 8580
cctgtggtag aacaagtcta caacaagata acatgattgc cccaaggcag aagtaaaaga 8640
aatattgtag gaaccataaa tgaatttaaa agctgatctt ttaaaaaata tataacttat 8700
caaagtgaga gatcagtcct ttatgatatt taaggagttc ctgtgaatgc accattatgc 8760
tggatactct gaaaaaatgc aaatcaagta tgaagcgata taaattctgc ccttaaggaa 8820
cttgcaatct agttggagat ttatgtttaa cacaaagaag cagtttttac aaatacttct 8880
tttgaggatt ctgggaagat ggcagagtag aaagcaccag gaatctgtct cctcacctag 8940
acaagaattg tactggcaga atctgatgta actattttgg aactctggag tctattgcag 9000
gcttgcaact tccaggggac agacttagat ggtaaattgc agttaatttt ggtctatttg 9060
agctcttagt acagtagcag ctacccatct tccacctctc aacccttagc agacagctgt 9120
gcacgttatt agagcaatct gcacacaact tacaggaatc aggtgggcaa aaagaaacac 9180
accatccaga tatctgggat ctgtgctctt gattggtcat tgctccttct cgtcacaaaa 9240
gcgcaaagag atgggcggtt gttgttgtta caccttactc attgttacaa ccccctcccc 9300
actcactccc ctgccccatg gatttaaagg gctagaaatc tccctctgct tcatttttct 9360
ctttcacttt tgggagccgg atattaaaga ctaggacatt taaaaacaac tgcatttatg 9420
gggaaaatta gaaagtcact gtacatacct agggaaaggc tcaggagaga ccttaagttt 9480
atagctcaag ctgatccttg gcacaggatt aacaacaatt acacagcaat taaacaaagc 9540
aaacacacac acacacaatg tagtctggga gagtgatgtt agcaagatgg ccaactagaa 9600
gccccttctg ctcatcccct cataagacag ccagaacaac aaataaacaa ctacatttta 9660
gcaaacttaa ctaagagtgc tagagtgcat caaagaagta acagaaatcc tagtgagcag 9720
agaaaagtgg gatggccaca tggagaatgg gaggaaatgc caggattcct aggatcatct 9780

-continued

```
gggaacgagg aggaacttct tcctatggca aggagataaa caagaagatc ccagctacac   9840
catgggcacc aacagatctc accactgggg ttccttagag tccagacagc aactaagcca   9900
agctgaggaa gctgcctaga gtctgcacag ctgtgttccc tccagagaag gagccaacac   9960
tgtgctccac ctgctgtggc ccacacagct actgtgccac tccaccttgg aactggaact  10020
acttctggag tgtgtcttgc ttcggggact tgtagccatg gcttcctttc atctgaacca  10080
cgccaggctg gtggctcaac atccctaagc taaactttaa gcagctgtta caccettccc  10140
tgtggagtca agcagaggtg gaactactcc acctactcct accccactgc ccttgggcta  10200
gagctgaagc agtatcctat ttcctgggaa cacactacct tggccaccca gagcagtcat  10260
gcacccctgt gcctaagctg aagtggtata cggcattcca gggaaacagg gcctgaacca  10320
cccagagcag tcacactccc cgggcctcag ctgaaggagc acatcactcc ctgcagaatc  10380
agtgccctgg ccaaaccgag cagctatgca tcccagggct gagctgatgt agtatcctat  10440
gtctcaggga aacagagcag tggctgagct gagacaccct gttctacagg ccaaataact  10500
gtagtacccc gcttccctgg agctggacta gtcctctaga gcctgagctg ctgagacact  10560
ctgaggagtg gagtcatcac tgtgctgttc cctacccccc attcccagcc cagacaacag  10620
ctatgcttca ccattttgta gtacttgctg ctgctgctac acttggcctc acagtctggg  10680
gtactgctta tccctagcta ttccaagatt tagagtcatg acttcatggt gcctcatccc  10740
ttgggacctg tgttgccact gagccctatt agctcatatt cccaaattaa aaccataccc  10800
tgctccccag gcccaaacct ccagagaacc ccttctttat agtcaggcca gtgctatgcc  10860
ctgaccccca taggggtaga atcaaagcta caacccattc tctgggccta agctgccagg  10920
aagcacctcc aggtcacaaa tcctggctct gtgagcaact acgtccaagc cctgccacag  10980
agagcaaacc cacctcagca accaagtgtc tcagtaggtt tgtgagatcc tgagcctagg  11040
acctttgccc agtagccact ctgaatacct tcatctggaa tcaagagctg ctgcagctgc  11100
atatatatag cccctgtcag acctgacacc aagaggtgtt gccttggctg agtctcccca  11160
ttgtggggaa gacaagaata ggaggatcct aaaagccttc aacactgaga acattaacaa  11220
cctacactac cactgccaca aacttctgca gcctaggccc ctgaggcacc catttactac  11280
tgacattgaa cacaggtaaa gcagctgctt taccatacca ctgcatctgt caggaaacag  11340
tcaccacacc cttcgaaacc agcatactga aacccaactg ctaataaaag actttatctt  11400
tgaaagccac tgtctgtaaa gtttggaaga ggtaattatc ctatcaacac aaagacacaa  11460
aaacatgaaa aagcaaggaa atatgacacc accaaaggaa agtaagaact ctctaatggt  11520
ggcccaatga aaagaagatc aacaaattgc tggaaaagga attcaaacta atgatcttaa  11580
ggaaactcaa caagatacaa gaaaatacag atagttcaat gaatcaggaa aacaattcac  11640
aatacaaaaa attcaacaaa aaaattaaaa catgatgaaa aacaaccaaa caaatcctac  11700
agttgaagaa ttcaatgaat tacatttaaa aaatacaata aagagcttca ataacagact  11760
tggtaaagca gaagaaagaa tctctgaact tgaagatata ccatttgata ttacttaatt  11820
gtagaaaaaa caagtgaaac cctacaagac ttatgggaca tcattaaagg aacaaacgtt  11880
catactatgt aagttacaga aagaggagaa aaggtaagag gcatatacaa actatttaat  11940
gaaataatag ctgaaaactt cccaagtctg gagagagata cagacatcca gatccagaaa  12000
gctcaatgat tcccaaatag atttaaccca aaaaggttct ctccaaagca cattattatc  12060
tgttgtcaaa agtcaaagac agagaaagaa ttctaaaaat agcaagagaa aggcatcaag  12120
tcacatttaa gaaaatcccc attcagctaa cagcagattt cttcacagaa accttacagt  12180
```

-continued

```
gcagaagagg atgggatgat atactcaaac agccaagaat gctatgccca gcaaaactat  12240
ccttcaggaa tgagggagaa atacagtttt tcccagacaa gcaaaaactg agggaattca  12300
tcactgctag accagcctta tgagaaatgc tccagggagt cctacatctg gaagtgaaaa  12360
gagagcagtc agtatcttga aaacatggaa aagtataaaa ctctctgata gagcagatac  12420
acaaaggaga aagagaaaag aattaaacct tatcaaacca tcaaaccaca atgataaata  12480
ataagagagg aagaaagggg caaaggatat tattagaaaa ctttaacaaa atgacaaatg  12540
taagggctca aatatcaata ataatcttaa atgtaaatgg attaaattcc atacttaaag  12600
agactggcgg aatatttttt tttttctttt tttttttttt tgagacggag tctcgctctg  12660
ttgcccaggc tggagtgcag tggcgcgatc tcggctcact gcaagctccg cctcccgggt  12720
tcacgccatt ctcctgcctc agcctcctga gtagctggga ctacaggcgc ccgctaccac  12780
gcccggctaa tttttgtat ttttagtaga gacggggttt caccgtgtta gccaggatgg  12840
tctcgatctc ctgacctcgt gatccacccg cctcggcctc ccaaagtgcg gaatattttt  12900
taaatgactc aattatatgc tttctataag aaacccactt cacctataaa gacacatata  12960
aactgaaatt gaagggatgg aaaaagttat tccaagcaaa tggaaaccaa aagctgtcag  13020
gaattgctat acttatgtca gattaaacag acattaagtc aaaaactgta aaaacagaca  13080
aagaaggtta ttatataatg ataaagggac caattcagca agaggatata acaattctaa  13140
acatacatgt acccaacacc agagcaccca gatatataaa gtaaatatta ctatacgtaa  13200
agggaaagat agactccaat atgatagtag ttggggactt cagcacccca ctctcagctt  13260
cggacagatc agcaaactcc aagtacagtg aactcaaaga gaccacacca agaaacagtc  13320
aaacttttga aagccaaaga cagagaagtg acttgtcata cacaagggat ctttgataac  13380
atgatcagca gatttctcac ctgatacttt ggagaccagt gtattcaaag tgctaaaaaa  13440
aacaaaacca aaaaactcaa aaccctgtat atggcaaaat tgcccttcaa aagcataagg  13500
aaattaagat gttcttagat agacaaaagc taagggagtt cattaccgct agaactgccc  13560
tgcgagaaat gcttaaggaa gtcctgaaag gtgaaatgaa agggcactag acagagggga  13620
cagtgcagat tcaggcaggt gcaatggctt ctggggaaga cccagccagt ggggctattg  13680
ccagcatcca gtcagctgcc accttccctg accccagtgt caagtgatgc gcagggtgat  13740
ccaggtgtgt gaggggcagc tggatgtcca gactgagggc actggtgcca tcagtggcta  13800
tcctaccact caattcatga cccaggtggt gatccagggt gatatcacca gttatgatgc  13860
agttaacaca gaggggaaag ctgctgagat acactatact ttcccacccc tgcagtggga  13920
gatggggcag gggtaccac atcagggagt acagctgctg ttgttactac ccagggctca  13980
gaggcactgc ttgggcaggt gactcttcct ggcactggtc aattatttgt gatgatgtca  14040
ccacaaggag tactgcaggg aggaagccag cacttgattg cccctaggac tcaaccttat  14100
ttatttggac gtaacaccat tgtaagtcaa gaagcatctc tatctatcta tgaacataca  14160
atgtgaaatc aaattgaggc cataaaacag ttgaacctca tcataagagt gactcatcgg  14220
tgtcacttct aagaccaaga aaaattctat ttttatgcag agaccatttg tttttttaatt  14280
aaaagacaac tctatttcaa agaggaaaaa aaatcaactc ttttttcagc tctctcagat  14340
gcagaaatgt aattatcagc atccctgtgc tgggagcaat cattagtttt tttagatttt  14400
taaaatatac ttcattatgt ttcactgtat tcattcttta atcagggatg tgagggatag  14460
aataacattt agaatatctg tacagtttgt atataatgtt cttatttctt gttgctttta  14520
taggtggaaa aaatctaaaa tctcctcaaa aagtagaggt cgacatcata gatgacaact  14580
```

-continued

```
ttatcctgag gtggaacagg agcgatgagt ctgtcgggaa tgtgactttt tcattcgatt  14640
atcaaaagta tgtgactcta cttactgatt tgtcagaatg acctgaataa tttttacaag  14700
tttaacaaca ccataatttt tagatttgga aagtgtttgg tttttctatt ttttagaaat  14760
gttacgccta ttttacataa tatttttaac tttgtttctg tagagactta gtcaaataca  14820
tctttgggtg ttgaagcaaa aaattgggga tgagggtggt agacagcgtc tctaacccat  14880
agccattcct tctttcttct gggtgttcca gcttcttttt tttttttttt taattattat  14940
actttaagtt ttagggtaca tgtgcacaat gtgcaggtta gttacgtatg tatacatgtg  15000
ccatgctggt gcgctgcacc cactaactcg tcatctagca ttaggtatat ctcccaatgc  15060
tatccctccc ccctcccccc atcccacaac aggccccaga gtgtgatgtt ccccttcctg  15120
tgtccatgtg ttctcattgt tcagttccca cctatgagtg agaatatgcg gtgtttggtt  15180
ttttgttctt gcgatagttt actgagaatg atgatttcca atttcatcca tgtccctaca  15240
aaggacatga actcatcatt ttttatggct gcatagtatt ccatggtgta tatgtgccac  15300
atttttcttaa tccagtctat cattgttgga catttgggtt ggttccaagt ctttgctatt  15360
gtgaataatg ccgcaataaa catacgtgtg catgtgtctt tatagcagca tgatttatag  15420
tcctttgggt atatacccag taatgggatg gctgggtcaa atggtatttc tagttctaga  15480
tccctgagga atcgccacac tgacttccac aatggttgaa ctagtttaca gtcccaccaa  15540
cagtgtaaaa gtgttcctat ttctccacat cctctccagc tccagcttct ttcaatataa  15600
gttggggtct gagctagggt atatcttgaa gatatggcat tgtactccaa aaggtccatc  15660
gaagaccttg gaataggcca ccaggtttcc tgtgatcagg ctttcctatt atctccatga  15720
tatactatat tttaatttta ggtacacttt tttttttttt ttttttttga ggtggagtct  15780
tgctgtgtta accaggctgg agtgcagtgg cacaatcttg gctcactgca acctccactt  15840
cccggtttca agcgattctc ctgccttagc ctctcgagta gctgggattg caagcacatg  15900
ccaccatgtt tgactaattt ttttattttt agtagagatg gggtttcgcc atgttggcca  15960
ggctgatctc aaacttctta cctcaggtgg tctgctcacc tcagcctccc aaagtgctag  16020
gattacaggc gtgagccact gccctggcct agatacactt tgtaaatata ttgttaactg  16080
ggcatggtgg catgtgtctg taatcccacc tacttgggaa gctgaggcag aagaatcgct  16140
tgaacccagg agacagaggt tgctgtgagc caagtttgca ccactgtact ccagcctggg  16200
agacagcaag actccatctc aaaaataaat aaataaataa aataaaataa aaatcgatat  16260
attggacctt gcatttctaa agactcagtt tttctggagt gttgatgtct cttccttagt  16320
actttctact taattattca agaggagagg caggcagaag gaggaatata gaagggaaca  16380
cagatcagga agtacagtac tttgccttcc gattatgtgt tggggcccca cctgccaacc  16440
atgttcccct gtccaagaaa aagcaggcaa tgaagaaata aggcattagg ccctccggaa  16500
ccaggagccc accacttcag ccacagctgt gacactattc tcgagttgta actaaaactg  16560
gcatatgaat ctcacagctt cagtaattgt gtatgcatat ataaacaaat acacactgta  16620
tatatgcata tatacactat atatatacat actgtatata tacattacac tatatataat  16680
acatactgta tacatacata tacacacatt gtgtatacat acatatacac acattgtgta  16740
tacatacata tacacactat atatacatat acacactgta tatgtatatg tatatacaca  16800
cacaaattca tatatgactt ttctcagaat tgatcattta aaatttttta tctctagaga  16860
ttttcattaa attgaacttt gagtttggtt accagttttg ttttttccct tagtttggaa  16920
tttccttatg aacaactatt ttaggtagag aaggaattat ttcagatacc cttatttaat  16980
```

-continued gttacttgta taaagaaact atttgcaaaa tatgcatcca acaagagctt aatatccaag 17040
gaactcaaac aatcaacaac aaaacccaaa tccatcaaaa ggtaggcaaa agataggaat 17100
agatattttt caaaagaaaa catacagtgg ccaacaagta tgtgaaaaaa tggtcaacat 17160
cactctaatc atcagagaaa tgcaaacgaa acctgccatg agatattgtc tccccgcagt 17220
cagaatggct gttattaaaa agttaaaaaa ggctgggcat ggtggctcac acctgtaatc 17280
ccagcacttt gggaggccaa ggcaggtgga tcacctgaag tcaggagttc gagaccagcc 17340
tgaccaacat ggtgaaaccc catctctact aaaaatacaa aaacttcagc cggatgtggt 17400
ggtgcgtgct gtaatcccac ctacttggga ggctgaggca ggagaatcgc ttgaacccag 17460
gaggcacagg ttgcagtgag ctgaaatcgt gcccctgcac tccagcctgg gtgacagcaa 17520
gacttcatct caaaaaaaaa aaaaaaccca acaaatattg aatatatttc atgccaaaca 17580
ctcttctgac tgcttagact gcctcagtga acaggagagg caaagatggc atgaagttat 17640
attatgaaac ggatttcatg aagtaaatat tacattagtt acatattcat atttcatatt 17700
ctgttctgag ctaattattg catatgataa tagttttttt gttgttggtt tttttttttt 17760
gagacggagt cttgctctgt tgcccaggct ggagtgcaat ggcgcaatct cggctcaccg 17820
caacctccgc ctcccgggtt caagcaattc tcctgtctca gcctcccgag tgcctgggat 17880
tacaggcatg cacccccacg cccggctaat tttgtatttt tagtagagac aggatttctc 17940
catgttgatc gggctgatct cgaactcctg atctcaagtg atccaccccc ctcggcctcc 18000
caaagtgctg ggattacagg tgtgagccac cgagcccggc caataatgat ttttttaaga 18060
aaatataaaa gtagcttctg ctgcaatatc ttgattagat gtaaaacagt tttaatggag 18120
catgcttcag catctcctga agtaggaaag acagatgtaa acagtgaggt tgggttgaaa 18180
ttatattaag ttttaaattt ttgataaggt tttctgttta taatgagagt ttctggattt 18240
ttagaaatag attctgatgt ggaacctttt caagaatgtt taaggtattt ttaatgccag 18300
ctctaatctc aggcctcaga tatgtaaaag tggaagtgaa aactggccaa gaatgaagta 18360
tttcatatgc tagtgtatat ttttggtaat ttcttaaaaa tgtttccatt ttgaaaaaca 18420
aggtagactt gtatttggtt cagcaacaaa attattttgg tattatctct ggtttctaat 18480
atctaaatcg tctttaaaat ggcatctgtg atattattaa aaataaataa atcagctaat 18540
gaattaggct tgacaaaaat gccttcccag aagatagttt ctctgctact tatggtcaat 18600
gggcttaaca taggtaaaag ttctcaaatc tgctaaattg gccgggcatg gtggctcacg 18660
cctgtaatcc cagcactttg ggaggctgag gtgggcagat cacctgaggt gaggagttta 18720
agatcagtct agccaacatg gcaaaacccc atctctacta aaaaaaaaaa tacaaaaatt 18780
agccagacgt ggtggcacac gcctgtaatc acagctagtt gagaggctga ggcaggagaa 18840
ttgcttgaac ctaggaagtg gaggttgcag tgggccgaga ttgcaccact gcactccagc 18900
ctgggcaaca gagtaagact ctgtctcaaa aaaaaaaaaa aaaaaaaaaa gaaatctgct 18960
aagttcgttt ctatccctca ctttccctgc aagctcttct tccccttttct gggcaacatg 19020
tccttttctg ctttaggcac tccatgccca ctttattttt catgtttgcc cctttttttga 19080
aaggaagaat ctaatatcac ttcagctttc tgattggcca gttccacttc caaaaattta 19140
tttgtttatg taaacatttt cagttttgtg gtttctgatg atgtaataga agaaattacg 19200
gagacaggca agcagaaggg atggtttgct tttggagagg gcagaggaaa ccttgaaacc 19260
atactgattc tgaggtcttt cttagggaag gtaagtctat tcataggagg aggtcagaag 19320
ggaatcatca aatccaattc cccagtttct atttaatttt attttattag agacagggtc 19380

-continued ttgctcggtt gctgaggctg gagtgcagtg atatgatcat agcctactgc agcctgcagc 19440
cttgaacccc tatgctcaaa tgaccctctc acctcagcct acccagtagc taggactgtg 19500
ggcatgtgcc accatgccct gctttgcctt tttttttttt tatttctcat agagacaggg 19560
tttgctatgt tgaccaggct ccaaactttc aataaggaag ataagatcca gaaacacaaa 19620
atagtttacc aaaagtcaca cagctatttt taacagagcc aacatactaa atccactttt 19680
accttatggg tcatttattt ctctgcttcc tgaagcaacc acccacaaaa ttatataaag 19740
aactgtattt taaaattcag tttcataagt aataacttgg cttatatgca ttgaaaaaga 19800
gtggaagggt gtatgctaaa atgttaatag gacattagct caagtagaag aaataactct 19860
taaaccaaaa atagaaataa ctcttaaaca agagttatta agagttaaga aataactctt 19920
ataccagtaa atagaaagta tttgacactt acatttatac atttgctcac tcattcattt 19980 gttttttttta ctttaaagaa ctgggatgga taattggata aaattgtctg ggtgtcagaa 20040
tattactagt accaaatgca actttcttc actcaagctg aatgtttatg aagaaattaa 20100
attgcgtata agagcagaaa aagaaaacac ttcttcatgg tatgaggttg actcatttac 20160
accatttcgc aaaggtaaga aaaagttgct agctgaatta tattctttag taaatattac 20220
cagagcagtt cactttccaa gccattcatt tgcatgatgc aaaatctaac atcttttaaa 20280
aagaacaaaa attcccttaa acctatatct tcttcctgct atggctccat ttgtcctact 20340
ttccctgtag tagtggttct caaagagtga tcctcaaggc cctttcaggg ggctgtaaag 20400
acaaagctat atttatgaca aatctaagac ttagttgcct ttttaatttt tgttctttct 20460
tgtattcaca gtggagtttt ccagaggagg ctgtttgatg tgtgatgtgg tgatatggtc 20520
actgatttaa catagaattc aatgtgaaat tcatctgcct tctttattaa tccaaacatt 20580
caaaagattt ggaaaaaaaa tgtaaaacag caccactctg aagtttctat gttccttttg 20640
gcaaatgttt gttaccataa aataggttta tcattgttat ttctttcttt tttttttga 20700 gacagagttt tgttcttgtt gcccaggctg gagtgcaatg gcacaatcac ggctcactac 20760
agcctctgcc tcctgggttc aagtgactct cccgcctcag cctcccgagt acctgggatt 20820
accagcatgc atcaccatgc ctggccaatt ttgtattttt agtagagaca gggtttctcc 20880
atgttggtca ggctgacctc aaactcccaa cctcaggtga tctgcccacc tcaacctccc 20940
aaagtgctgg gattacaggc gtgagccacc atgcccagtc cattgttatt tcttaatgga 21000
ttaattagtt aaaatggatt gaaaacttta ccagttttaa tgtttaatat gctaatataa 21060
aaatatacag cccacataaa taatggctgt ttgggattct cgataattcc tttaagaatg 21120
taaaggagct gagtgtagtg gcccacacct gtaattccaa cactttggga ggctgaggtg 21180
ggaggatcac ttgaggccag aagttcaaga ccaacctagg caacatagtg agaccccatc 21240
tctacaaaaa atatataaaa attagccagg catggtggtg cacacctgta gtcccagcta 21300
ttcaggaagc tgaagaggga ggatcacttg agcctgggag atcaaggttg cagtgagctg 21360
tgtttgtgcc actgcactcc agcctgagca acagagctag accatatctc aaaaaaaagt 21420
ggggatcctg agaccaaaag gtttgagaac cactgccctg taccaagaat gatctgtact 21480
ccctttctat actaatcttc caattccctg tcagccctct ccattcaaat tctgttcctc 21540
ctcacttaaa accactcttt ttggccaggc gcggtggctc acgcctgtaa tcccagcact 21600
ttgggaggcc aaggcgggca gatcacgagg tcaggagatc gagaccatcc tggctaacac 21660
ggtgaaaccc tgtctctact aaaaatacaa aaaaaaaaaa aaaaaaacta gccgggcatg 21720
gtggcgggag cctgtagtcc cagctactcg ggaggctgag gcaggagaat gacatgaacc 21780

```
cgggaggcgg agcttgcagt gagccgagat cgtgccactg cactccagcc tgggcgacag  21840
agcgagactc cgtctcaaaa aaaaaaaata aataaaccac tcttctcaag gtcacagcag  21900
cctccacaat gccaagcaaa ttcccagtcc tcttctggct tcatccctct gtagcataga  21960
tgtggtcatc actcagtttt tcctttactg gatctctggg acactgctct ttcctggttc  22020
tcctcctgct cattgatcgc ttcatcttcc caacttttca gtgttagact gctgctgggc  22080
tcagtcattg aacctcttct ctttctgtat cactccactg gtgatcttac agctttctat  22140
cctatctgta tgctcttaac tcccagaagt ggcaggcaca tattaagtgc tcagaattat  22200
ttgttgaatg aaggttttgg cattgtatta ataaagttcc atagtaattg ttttgatttt  22260
tttgcagctc agattggtcc tccagaagta catttagaag ctgaagataa ggcaatagtg  22320
atacacatct ctcctggaac aaaagatagt gttatgtggg ctttggatgg tttaagcttt  22380
acatatagct tagttatctg gaaaaactct tcaggtgtag aagtaagcat tatttttacc  22440
tctgtttaat cgatgtgaga gaaaaattag gcgaattaat cctaaaattt gactttatac  22500
tttttaaag aaccaactta tatttgtgtt ataggaaagg attgaaaata tttattccag  22560
acataaaatt tataaactct caccagagac tacttattgt ctaaaagtta aagcagcact  22620
acttacgtca tggaaaattg gtgtctatag tccagtacat tgtataaaga ccacaggtaa  22680
ggaagatgtt ttgttttaga ttcaataaat atataaacag attgtcaatt ttggcatctt  22740
ccccatattg ctgaagttta catgataggt caatatatgt taaaaacatt gtaacattta  22800
cataagcaaa ataaatgtta cttgggattt ttgtctcaaa tagtaatgaa aattaattct  22860
acttaaaagt tcaggctggg cgtagtggcc cacgcctgta atcccagcac tttgagaggc  22920
tgaggtagct ggatcacttg aagccagaag ttcgagaaca gcctcgccaa catgggaaaa  22980
ccccgtgtct actaaaaata attagctggg cgtggtggct cacgcctgta gtggtagcta  23040
cttgggaggc tgaggcacaa gaatcccttg aacctgggag gtggaagttg cagtgagcca  23100
agatcgcgcc actgcactcc agtcgggagc aagggggaca aagagtaagg ctccgtctta  23160
gaaaaaaaaa aaagttcaaa tattttgtaa tgacaaaact tttcatttgt tcagaatcca  23220
catgaagcag gaggtagctg aactatgagt tctgcaagtg ggaagaaaag gtggggaagt  23280
agttgctagt agacaagtta ttgttcaaga aagcatacct ttgtaagtgg aatgttaaaa  23340
tatgaaagta tcctgataca tttagtaaca tctttccaat aattaaggtc aagggcagga  23400
gctgggattt gtttatttta attgtaaatt tcatatgctt ttttttttaa tcaaacatta  23460
cggaagggtt taaagtgaag tcttcttctc ccttcttatc cccaattcca ttcactagag  23520
ataagcattg cttagcagtt tgtgtatatc ctttcacaac ttttttcagg atttatgtaa  23580
gcatatacac agacccacag tttcttgggt tttgtttttt aaaattacaa aataaaatct  23640
tactagaagt attttacagc ttgcttactt aacccagtgt gttggggata ttctatatca  23700
ctcaatacag atctattacg ttcttcattt gatcttagcc atctattgca ttctttcttt  23760
tttacttatt tatttattta tttatttatt tatttattta tttttgagac agagtctcac  23820
tctcttgccc agaatggagt gcagtggctc aatctcggct caccgcaacc tctgcctccc  23880
agcttcaagc gattctcctg cctcagcctc ccgagtagct gggattacag gcgtgtgcca  23940
tcatgcctgg ctaatttttg tatttttagt agaaatgggg tttcaccatg ttggccaggc  24000
gcgtctcgaa ctcctgacct caggtgatcc atccacctca gcctcccaaa gttctgggat  24060
tacaggtgtg agccactgcg cccggcctgt agtctttcaa atggctgcat agtattacat  24120
agtgtgaata caaaccatat ttaactatta ccttataatg ataaaatgcg agcctttatc  24180
```

-continued

```
ttcttgccag ttatctcact tgagtaaaaa tgtgtgcttt tttttatctg ttctttggct  24240
tctagttgaa aatgaactac ctccaccaga aaatatagaa gtcagtgtcc aaaatcagaa  24300
ctatgttctt aaatgggatt atacatatgc aaacatgacc tttcaagttc agtggctcca  24360
gtaagttcca ttccataaat ttccttttgc ccagtttgtt ttgattatgc ttcttttcgc  24420
tctgcatcag tcaccaggtc cttgcacaca gaatgaccga ctgggaggtg ggtacgatat  24480
attggaaacg tgagaaatct catttctaac cccagttctg ccagtaacta actggatgac  24540
attgagctaa tcgcttaacc tccatgggcc tcaatttctt cacttgtaaa atagatggat  24600
tctaatatct ggggttctta ctggcttaag aaaaaaaaga aagtgtaact agttgcatgt  24660
gttatttccc caatctggaa gactcgacag ttgaccctga tctttttcta agaactcact  24720
tcttccatga gtccttaaaa tgatctcagt ccactcactt gttcaattca aaaaattagc  24780
cttcctattt tctttattac tttagtggtt ttgacaaaat tttgtagtag atacttcggt  24840
gggaaagaaa gttggaaaga actatgttct atgtggttga gcagaggcta gctaaacatg  24900
gatgaagtcc aggcgctgca taaatgaaag agaactggcc tggtgcagtg gcgcatgcct  24960
atcgtcccag ctactcagtg ggctgaggca ggaggattac ttgaggccag gaattgaggc  25020
tgcagtgttg tatgatcaca cctgctagta gccgctgcac tgcagcctgg gcaacatagt  25080
gagacccccca tctctaagca ttaaaatttt taaaaagctg ataaaagaga actgcatgta  25140
gtttatattg attggaaaat tgtaggagat gaatagagaa aagagaagag gaaaattaag  25200
tagaaggaaa aatgggttat ggggagaaaa gagatggaaa gaaagatata cattggtggc  25260
agaggagtag agagagcaaa ggcaagtata gctaagacag gaaaggaaaa gtcagaagaa  25320
actggaaaga aacagaaaaa atgagggaga agggaagtgt aagtaccgct atgatcaatt  25380
tctatctttt agtgttaatt ttgaaccaag ggtgactggt agaatgcaaa tgcatttatg  25440
tgcatatgtg ccccacaatg catatataac ctcacaaacc aatcaggaaa ctgttcagta  25500
gtcttttgtg tatacctcac tttcagaagt gaataaataa tagggtcacc aaatagataa  25560
tgagaggtat ttctgatagc tgatctctaa gcttcttttg ggtacttacc atattgtaca  25620
aagcactgaa gaaatggaaa gagtcagcag aatcaaacgt ggttcaaaaa ttgaaagcag  25680
ttagccaaca ttgcaaagtg ttgtgtggtt taggactaaa gagtggtata caaattataa  25740
gggttgcaga aattgaaaat gtaaaggtga ataggggcta aagagaccaa agaagccata  25800
aggaaagaga taaggtatga acaaggcctt gattgttaat tcagattttt tttaagtaga  25860
caactattag atgttagttt tctgtgtctg taactaatta ccacagactt agcaacttaa  25920
acagctgttt attgtctcaa agtttctgtg agtcaggagt ccaagcgtgg cttagctggc  25980
tcttctgcta agcagtcaag gagtcagtca ttcatacaag acttgggggc cgctcccaag  26040
ctcacatgtt gttggcagaa tttatttcta gagctcatgg tggctcactt cttagaggcc  26100
atcaggaagg gagagtctga cctctagatc cttttttttt tttttttgag acggagtctc  26160
actctgtcac ccagactgga gtgcagtgac atgatctcag ctcactgcaa cctccgcgtc  26220
ctgggttcaa gtgattcttc tgcctcagcc tcccaagtag ctgggactac aggtgtgcac  26280
caccacaccc agctaatttt tgtagtttta gtagaaacgg ggtttcaccg tattggccag  26340
gctggtctcg aactcctgac ttcaggtgat ccacccgcct cagcctccca aagttctggg  26400
attataggcg tgaggcaccg cgctcagcca ttttttttgt atttttagta gagacggagt  26460
ttctccatgt ttgccaggct gttcgcaaac tcctggcccc aagtgatctg cccacctcag  26520
cctcccaaag tgctgggatt agaggcatga gccaccatgc ctggcctaga tcctctttta  26580
```

-continued aggggttcat ctgattaggt caggcccacc cagaatagtc tctcatttga ttcaactgat 26640
ttgggacctt aattacatct gtgaaatacc ttctcttctg ccacttaatg taacctaatt 26700
atgagaggag ggcctccatc gtatttacag gtcctgccca tgctcaagag gaggggatta 26760
tacaggatgt gtacaccagg gggcaggaat cttgggggcc atctcagaat tttgccttct 26820
ccagtgggga ggatgtcctt ctagagtagc agaacatttg gacaccaggt ggcaatggga 26880
agaaagctga ataagtagaa tgggacaaga ttagggtcaa cctcaggctg tcctgtaggc 26940
ttttggggat tttgtgttgg ggtgatagtt aacctgagct ctggatttga ggaaggtgca 27000
tgcggcgaca tggtatgtgg gagagtggac taaggagaca ctaaagagag ataaggaaac 27060
cagtcaggag gctattagag ttctgggctt gaactgagat gcttttagct gttggtttct 27120
gggcaagtta cttaacctct ttagtctcgt acttatactt gctcttataa ccccgcagtg 27180
tgtctctatt ttagcactta atcagtgtcc attggtatgc tggcgcatgt ttagcagctg 27240
gctttccaga aagaaaaagt cctattttgt agtgtttgct gatttttatg atataaatat 27300
tcccaccatg gccactttca agccaccagc ctgatgtccc tgaatatgga gttgggaaca 27360
tatgcacagt agcacaccac tatcatatag ctacaataga taaagatagc cccaagagct 27420
tagaaaataa aatgtagtaa aataattagg acaagatgaa tttatttatt acctctgtct 27480
ttaaaacaat tttttatttg caaatttata taacttaatt tttagtaatg gtttttcttt 27540
aaaaaccagt ttgtatttta ggaggccgag gtaggtggat cacctgaggt caggagttca 27600
agaccagcct ggccaacatg acgaaacccc atctctacta aaaatacaaa aattaggcag 27660
gcctggtggc gtgcacctgt aatcccagct actcaggggg acagaggcag gagaattgct 27720
tgaacccagg aggcagaggt tgcagtgagc caagatccta ccactccact ccagcctggg 27780
tgacagagcg agactcggtc tcaaaaaaaa agccaaaaaa aataaaccag cttgcagcat 27840
tcctggaaat tctaactaac agatgttctt gcatattgat atgagccacc tccagcagag 27900
cacaacatga ccacagtctg gaacagtctt tggttttctt ttatgttaga tgcatatctc 27960
ttccattgtt tgtgagtttc ctgagtgtgg atactattta tttctgtaac cttagcccct 28020
aacatagtgt ctggcaattg taaatactta ataaatatct aatgaattta aaaaatattt 28080
gtcttaaaag cgccttttta aaaaggaatc ctggaaacca tttgtataaa tggaaacaaa 28140
tacctgactg tgaaaatgtc aaaactaccc agtgtgtctt tcctcaaaac gttttccaaa 28200
aaggaattta ccttctccgc gtacaagcat ctgatggaaa taacacatct ttttggtctg 28260
aagagataaa gtttgatact gaaatacaag gtaaggcagt agtttttact ggagattgta 28320
attctctggt gcaagttttt aaaattgttt ttctaattga acattatttc tttacaaatt 28380
ttttctagct ttcctacttc ctccagtctt taacattaga tcccttagtg attcattcca 28440
tatctatatc ggtgctccaa aacagtctgg aaacacgcct gtgatccagg attatccact 28500
gatttatgaa attatttttt gggaaaacac ttcaaatgct gaggtaaaaa gactgtatag 28560
tataattttg taacttagag ttataattat gatttgggta aataaagctt gaatgtaaaa 28620
tttgggggaa atttttaaac tttatgtggg ctggatgcag tggcctgtaa tcccagcact 28680
tcaggaggcc aaggcgagag gatcacttga gcctaagggt ttgagaccag cctgggcaac 28740
atagggagac cctgtctcaa taaaaatttt aaaaaattag cctggtgtgg tggcgtgcac 28800
ctatattccc agctacttgg ggtgggaggg tcacttgaac ctgggaggtc aaggctgcag 28860
tgagccatga tcgtgccact gcactccagc ctgggtgaca gagtgactga cagcttgtct 28920
ttaaaaaaaa aaaatgtgat taactcagat attaacaaaa tgaagattat gagcattttt 28980

-continued

```
catgttttgc actgtagagt tatgggtgag ctgcatctgg gccccagttt gcttttaaaa  29040
tacagattcc tgagcctatt gttactgaat cattatctct ggggatggaa ctcaggaatt  29100
tgcattttta acatgattcc catgtattca tctaaacctg ggattctcag cactattgac  29160
gtttgggctg gatagttcct tgggaggggg ctgtccagtg cagtgcagga tgcttggcaa  29220
cattctggtt tctgcctact agatgccagt agtgttcctt cctagttgtg acaaccaaaa  29280
acatcttcag atattgtcaa atgtcccctg gtggctcctc caaggggaca aaaattggtt  29340
cttatgggac aaaagaattt atgtagtaca gttgtttgtt ttcctccaaa accattggaa  29400
agcattcttc caaagttcag ctttgcccaa caaaatctta ttccttagta tttaatttta  29460
tgatggggga aggattagga aaaaattgcc caaaaagttg tttagttggg gaggtaatga  29520
aaaaagggtt gacaaacact ggtctaaacc ctaaaattca gataccactg acaaagataa  29580
tatataccgt cagataatat acgtgtttcc cagatcactt ccccctcgtg gacttgtagt  29640
caagaatcga cctttaaaac tcctgtccag tcaggctggt aaattcttta acttcacctc  29700
atttctattt ggaaatctaa gcaaattcca ttgatttggc tgcttccctt tttaattgtc  29760
tgacaaccct gtaaccatag cttaatgtag cccattgaga attatggtcg gttttcagat  29820
gtctgtagat cagacaaacc taaatttcta tctcactgct aaactgtgta accttacgta  29880
cgcagggtgc tttacctctt ggagactttg cttcctcttc tctgaagtgg tggtaatcat  29940
aacaactaaa tttttcaaaa ggatgtttat aaggtttaaa aggaagtaac aaatatgaaa  30000
atacctagca cattgctgga caagtagtag agattcaata aattgtagtt gccatcttaa  30060
cctatactgg ataatatatc aataattgtt actatagaaa ctcttattga atacttatat  30120
gtaaggtact atgctaagta ttgtacatga attgtctcag tcattcttca aaacaaccct  30180
gccggattat gtgattggtt acattgctgt ttggcaaata cttgggacgg tgacttcttc  30240
cctgcaccac cagaccgtag atgctggagc ccaagtagat gtgctgagaa cagaggcctt  30300
aagtgtgctt gcagggtttg gcttggctct tgcactgctc ctatttgcca ggaataaaat  30360
gtattccaca tagtctctgg tccaaggagg attagaggct gctggagctg acctaaaccc  30420
catgcacagc ctccgtggga gctgcccagc cagtctgtag acttgtgagt gagaaactac  30480
ataatcgttt tgtgagccac tgaacgttaa ggcagttttg ttatctatat tttttattt   30540
tattttattt tattttttt tttttgaga caggttctca ttctttttcc caggctggag  30600
tgcactcatg tgatgtcagc tcactgcagc ctcgacttcc tgggcttaag tgatcctccc  30660
acctcagctt cccaagtagc tgggactaca ggcacatgcc accatgccta gctaattttt  30720
tgtatttttg ctaaagatgg agtttcacca cgttgcccag gctttttgg tggtggtggt   30780
ggtggttgtt ttggaaatag ggatttcctc agcctcccaa gtaacagaga ctacaggctc  30840
acaccaccat gcctggccaa tttttttgaa atttcttgta cagacagagt ctagctatgt  30900
tgcccaggct cgtcttgaac tcctgggctc cagtgatcct cctgcttggc ctcccaaagt  30960
gctgggatta caggtgtgac ccaccggctt gttagacatt attctggcga tagctgactg  31020
atacagatag cagcaataac tgtcccgatt ttatagatca gggaatcagg tagagagaaa  31080
ttaaataatg cttgcaagac cacacagctg taagtgatac tcttaataag gcagtttgag  31140
gccaaaaccc ctactcttaa ccattctgtc actaatcaga ggtaatacaa tggcaattac  31200
cccagacttg gcatgtactt gtaaatcaat tagaattctc ttaggaatag atcatatgct  31260
tttttggcag cagcattttt aactttctga tttggttata gtggtgtatc taaaacaaat  31320
ttatatttct cacacatata ctctgtaatc ccagcacttt gggaggccaa ggtgggtgga  31380
```

-continued

```
tcacttgagg ccaggagttc aagaccagcc tgaacaacat ggtgaaaccc catctctacc  31440
aaaaagaaaa aaaaattagg cgtggtggca tctgcatctg taatcccaac tactcaggag  31500
ggtgaggcag gagaatcgct tgaacccagg aggcagagat tgcagtgagc ccagattgca  31560
ccactgcact ctagcctggg tgacagagcg agactgtctc acaaaaaaaa caaaacaaaa  31620
caaaacaaaa caaaaaatac ataccaacta cgtgggagag gccaatgtta gactgaacat  31680
aaaaaattga gaaagcacat attccctgat ttcttgaggt gactaaattt tatcagtgat  31740
ttaattatat tttctagaga aaaattatcg agaaaaaaac tgatgttaca gttcctaatt  31800
tgaaaccact gactgtatat tgtgtgaaag ccagagcaca caccatggat gaaaagctga  31860
ataaaagcag tgtttttagt gacgctgtat gtgagaaaac aaaaccaggt cagaatcttt  31920
tattgtcttt tttaaaaatg tagctagaca taataaaagt aattctatac tgtacattga  31980
aaattgtaaa acattttctc tttactgcaa aaaatatata gaaagaatgt tttcttcatg  32040
aactacatga atcaaaagta gactttttag aaaatatttg taacgcttaa ctctcaagtc  32100
ggtgttgttg gatgctttat atttcatcca gtatccctat aattaatttc cttaatgtat  32160
ttctctttaa catttaataa aactatttta aatttttaga atataatcct taacataatt  32220
atcatgtaga aatcacttag ttcaattgtg agttttttaa tgtgggaatt ggtttagtct  32280
cattttctat tttacagttt ctagtgttga ccggtagagg cttagtcaca gaatatctat  32340
taaattttgc tagttgtatg gtgtaaaagt gctgaaggat acttgcatgt ttggcctgta  32400
tgtcaatatt gtatttctcc ctgaggatct cttacttcag ttcccacgcc aatctttaaa  32460
tgtaaatgtc attgcctatg gttgctgtgg actcagtgct gccagaaata tttttaagag  32520
tattatttaa tagattttat atttcctttc atatggctag tctttcacac agctgtcagc  32580
actgttaagg catttgtatg tcaaaatata tgctaaatat cacgtatatc tttttaggaa  32640
atacctctaa aatttggctt atagttggaa tttgtattgc attatttgct ctcccgtttg  32700
tcatttatgc tgcgaaagtc ttcttgagat gcatcaatta tgtcttcttt ccatcactta  32760
aaccttcttc cagtatagat gaggtatgtt actttttta ttttttgtc aacagctagg  32820
taatgaacag aaaatgtgtt tgatttcaac aggatatatg taggttttct tgatatccag  32880
aaaataatag agactgattt gggtatcttc ttcaaagctt tagtcaatta actttaaaaa  32940
cagtaatttc atgtaataac atagcatgag atagtaatga ttgtccttaa tttcatattt  33000
ttctggcaat tcctagattc actgtggcat ttgttttacc gtttaaagcc tgtgattctt  33060
ggccaagcgt ggtggctcac gcctgtaatc ccagcacttt gggaggctga ggcgggtggg  33120
tcacttgagg tcaggagttc gagaccagcc tggtcaacat ggagaaaccc tgtctctact  33180
aaaaatataa aattagccgg gcgtggtggc acatgcctgt aatcccagct actcgggagg  33240
ctgaggcagg gggatcgctt gaacctggga ggtggaggtt gcagtgagcc gaggtcatgc  33300
cactgcactc cagcctgggt gacagagcaa gactctgtct ctaaataagt aaataaagtc  33360
tgtaatgtga ttcttctcag tacagacagt cccaaactta cgctgtttca atttgtgatg  33420
cgtttgtcag aacgtaattc cattgtaagt taggagcatc tgtatatatc cagaagacta  33480
aaatattcta tcagcgtaga aagtatattc tatggatgaa atcatacaaa atgaaataac  33540
taaaaacatg agactttttt tatgacacac atcacagttt tttgtttggc acttctatga  33600
agctagcata ttaaatgaaa gcactgaatg gtgaaggcct aaacatagaa tctgttcctg  33660
ggaaaccatg tgctcatcta gggtgggttt tgtgaatttg agcaagtcac taagggcagg  33720
taagcaagta cccttggctg taaaccaccc catagaggtg ttaggagcaa aggagttaaa  33780
```

ccataagaac cttaccactc taaaaatgct ccgtaaatat taacaatttt actattatac 33840
ccctgagttt ttaaatgtca ttcctgtgta ctgtaatatt catagctatt atttaaaata 33900
gacttaaaaa ctagttacaa tagccaataa tttctcaatt gtgcttcttc tggatatata 33960
tgtgttggat acaaacattt ttattatttc aaaaaaaaaa agtcatgatc ccagagtccg 34020
cccgctcctg tcctttcccg tgttcttccc cgcctacccc gatggcacag tgtacctttc 34080
ttaggtactc ttcaaagact caccacagaa ggtactaaga tatgagtgac ctcactaatg 34140
atgcttttaa acattataag gcaattagta tgttcttagg cgacttttta atatgcatgc 34200
cagaagatag gttttctcag taatggatgt aagaaactaa agctattaca actagaaaag 34260
gaatttttat tattttaaat aattgatttc tactctttcc cttttttaa attagtattt 34320
ctctgaacag ccattgaaga atcttctgct ttcaacttct gaggaacaaa tcgaaaaatg 34380
tttcataatt gaaaatataa gcacaattgc tacagtagaa gaaactaatc aaactgatga 34440
agatcataaa aaatacagtt cccaaactag ccaagattca ggaaattatt ctaatgaaga 34500
tgaaagcgaa agtaaaacaa gtgaagaact acagcaggac tttgtatgac cagaaatgaa 34560
ctgtgtcaag tataaggttt ttcagcagga gttacactgg gagcctgagg tcctcacctt 34620
cctctcagta actacagaga ggacgtttcc ctgtttaggg aaagaaaaaa catcttcaga 34680
tcataggtcc taaaaatacg ggcaagctct taactattta aaaatgaaat tacaggcccg 34740
ggcacggtgg ctcacacctg taatcccagc actttgggag gctgaggcag gcagatcatg 34800
aggtcaagag atcgagacca gcctggccaa cgtggtgaaa ccccatctct actaaaaata 34860
caaaaattag ccgggtgtgg tggcgcgcgc ctgttgtctt agctactcag gaggctgagg 34920
caggagaatc gcttgaaaac aggaggtgga ggttgcagtg agccgagatc acgccactgc 34980
actccagcct ggtgacagcg tgagactctt taaaaaaaga aattaaaaga gttgagacaa 35040
acgtttccta cattcttttc catgtgtaaa atcatgaaaa agcctgtcac cggacttgca 35100
ttggatgaga tgagtcagac caaaacagtg gccacccgtc ttcctcctgt gagcctaagt 35160
gcagccgtgc tagctgcgca ccgtggctaa ggatgacgtc tgtgttcctg tccatcactg 35220
atgctgctgg ctactgcatg tgccacacct gtctgttcgc cattcctaac attctgtttc 35280
attcttcctc gggagatatt tcaaacattt ggtcttttct tttaacactg agggtaggcc 35340
cttaggaaat ttatttagga aagtctgaac acgttatcac ttggttttct ggaaagtagc 35400
ttaccctaga aaacagctgc aaatgccaga aagatgatcc ctaaaaatgt tgagggactt 35460
ctgttcattc atcccgagaa cattggcttc cacatcacag tatctaccct tacatggttt 35520
aggattaaag ccaggcaatc ttttactatg cattaagacc tctgattcaa aacttattag 35580
aacagtagct tctgctggaa tttgcaatca ctgaagtcat agaaaatagg taactatcta 35640
attagagaaa taattgttgt attttaagat ctgagagtgt gtacaagttt tagtatacat 35700
gccatgccag aagatagtgt atgcaagaag tcttgggacc agaaaatggc aatgatagga 35760
gactgacata gaagaagaat gcttccctag gaaaaaggtc gctggctttg gtgcaagagg 35820
aagaagaatg ttccactgga agcctgagca cctaatcagc tctcagtgat caacccactc 35880
ttgttatggg tggtctctgt cactttgaat gccaggctgg cttctcgtct agcagtattc 35940
agatacccct tctgctcagc ctgcttggcg ttaaaataca aatcattgaa ctgaggggga 36000
aaaatgtaac taggaagaaa aacccaattt aagaaattac ataatgcttt ccaaaggcac 36060
ctacaactta gttttaaatt acttgctact ggggattacc catggatatc cttaataggc 36120
aggaagtctg ggaattctgg tggcctctag ggcagtgttc tcacagcacc gttccgacag 36180

-continued ggaccagtga aagaaaagag acaaagttag aacgtgctgg ggagcggcca tttctaaggc 36240
cagtctggtt taagtagtca tttctgctga aaaaacagat gatcctggtg gaagaaaagg 36300
ttgaaggcag ctgccctcgg gagggctgtg atgctcggca catcctgcct ggcacataca 36360
cgtgtctgca ggccacaccg tgcatgtccc cagacctgcc gcctggcttc tggagtgctt 36420
caagcagagc atggtgggtc attgaggaga cccaggaatc tcatctgaga acccactctc 36480
tgccggagaa ccccatggtg acacatttc atctttctga ccagaggctg ttttttttt 36540 tttttgagac agtctcattc tgttgcccag gctggagtgc agtggcttga tctcggctca 36600
ctgcaacctc gcctcccggg ttcaagcaat tctctgccgc agcctccaga gtagctggga 36660
taacaggtgc ccaccaccac accccactaa tttttgtatt tgtattttta gtagagatgg 36720
ggtttcacca tgttggtcag gctggtcttg gactcctgac ctcatgctcc acccgcttcg 36780
gcctcccaaa gttctgggat tacaggtgtg agccaccgtg cacggccggc ctgacctttg 36840
gaaaagcctt gtcactttgg acgtttgcgt ctttgaagag gcgatgggag catatcatga 36900
ctgcctgcca ccattgcttt tcagactacc acaactcaat catgctgtcc aggacttctg 36960
gccctgtgtt caccactggg aaaacgtact tcagactgga tagcctaaaa aggagcaatg 37020
cccttgtagg atgtggagaa gggaaaatac ggacattaac attaaaagac accagtgaaa 37080
ttgttaggtc tctaggaagt tggagcacaa ggcttcacgc tttaagacca tctgtggttt 37140
tcagtgaaca agcgctgagc accagcagca gaaaacaaca acaaaaaaac acctcgtttt 37200
taccttgtct tctagacatg aaaaggcagt tgcattccac tctgcattat gttctacatg 37260
ttgctttatc agtatatgct tagctgtaag tgacaagtat tttttctgaa cagaagttta 37320
cttagaaata ccatgcactt gggggtacca attaaccgcc tgaaaattag catattgata 37380
gttcttagag agaccagata taatctaaga atttatatga aagatttgta tcattagagc 37440
cagaaataat tttatattaa tatataatac agattaacat tatatataat atgtacctgt 37500
gtcacttctg acatgagcct gtaaacatat attcatatat gtacctgcac atgtacccac 37560
ctgatgtagg tcttattcct ttagtatgga cttaaagtac ttattcatat accttgtaac 37620
taaaaattag aacagctccc tagaattgtg aacttttaag agtctgacta gaaatttgca 37680
acttataaaa aagttacttt taaaaatata agttagggct aggcacagtg gctcatgcct 37740
ataatctcag cacttttggg aggccaagac aggaggatca cttcaggcca ggagttcaag 37800
atcaaccaac ctgggtaaca tggccagacc ccatctctat ttatatatat atatataaaa 37860
cttagagttt ttatcttccc ctaaaagagg ccgtgatatt tgcagcagcc tcaaattgct 37920
cttaaggggt ttaggtgtgc agaagctttc ctttccctac ccagtaacca tgtgactact 37980
aacgtggtat attgatttat tttgtttgct gtctgtctcc cctgccccac tgctggaaca 38040
gaggctccaa gaaaacaggg accttattat tcattactgc atccccagta atgaaagtac 38100
ttagaaaata attattgaat gaatgaaatc taaactgtga acctgagggt gtttgtggca 38160
gtgtttgttt tactgaattg tagaaggaca taaccgtgtt ttcagtgttt ctatggaaca 38220
aacttgtaca ttttatttca cttgtgtttt gtcttaaacc ctactgctgg aaacaatttt 38280
atgtaataag caatgggccc aaaagtctag gagttttttt gtacttagtg aatttgtatg 38340
caacagagat gctgcagctg atgcctttaa aaggtattca tcatggaaga gctgaggcct 38400
gtgcttggtg ttccagagcc cagggttgag catcctgaag gagccactgc agccgtcact 38460
gtccccagag cctgtggaga tagagcctgt ttgctgcttt ttcttcccgc tcttaagaca 38520
tggctggagc tcagtcttca ttgaatgaag tttgctgtgg tattgcatag ccttgctttc 38580

-continued

```
ttgaactaaa ctgtttgccc ttcacaagta gttcttcttt caggattagt tcgttccaag  38640
gaggctcttc agtctcacag ataagtagat ctctcctgct gtctggacac atttcactcg  38700
gaaattgaat acaatttgta ttcaggctgg gaacctgaac acacacttgt gtttttaagc  38760
ttcccttttt tacagtggac aaggacacaa ataataaata aatcatccct aatgcccaag  38820
aaatgccctg gtacttagta ataacaaaat accagtaact tccagttgtt tctcactacc  38880
ttttttcttg agtaggatga taatagaatt acaactcttg agggcaacat aaatataggt  38940
ggatatttgt ggtatgatat tgatggaaaa atagcaatct ttttctttac ctgaggggaa  39000
caaaggcaag aggagaattc gatagttctc ataacaaagg atttctgagt tttcctcccc  39060
tttctgtgat ctgtctccac ttggaactca tgttctagca aaggacattt tgtgggtgaa  39120
gaagtgatta atgattagga tgaagaaaat gttggcagtt ccagcctggc caacatggtg  39180
aaaccccgtc tctactaaaa atacaaaaat tagccaagca tggtggcatg tgcctgtaat  39240
cccagctact ggggaggctg aggcaggaga atcgattgaa cccgggaggc ggaggttaca  39300
gtgagctaag atcgcaccac tgcactccag gctgggcgac agagcgagac tccatctcaa  39360
aagaaaaaaa atgttggcag agaagatgtt ctgttgtttt tttttttttt taaggtcttg  39420
agaaaaggga ggaagttgaa aaattttatc actcaatagc tggattaaat taaacattac  39480
gtctcacagt gactcaccac ccttgagcct ccctcccaga ttttctggat acatcaaagt  39540
taagaagaaa aacctatttt cctatctttc cagtaaaagg accctttttt ctaaacatag  39600
tccttaaata tataataggc tttttgtgta cttgactctg ttgtctattc ccaaatttta  39660
taatactttt aatattctgg aattgtactt agagagatta ttctaaatgt tgtagtataa  39720
aagtacatca tccactctga aatctcccta aaagaactcc actgcataca cgtggagaag  39780
tcatcatgcc ccatctgtgt ctgtacctgc gggtgtgtct agcatgctcc ctagggaagg  39840
gattttatac catttgctta tatttatttg gcaagctcca tgaaaacaag gactgttttt  39900
taactttgtg gctgacactt ggttgcctaa gtgtttaacg gtgattgagc ggggacgttg  39960
acggtacaaa cactgattga atttaccact ggagggcaac aagtcaccct gttcaggctg  40020
acaatcggtt actattcaat aattccattc ccagaagata cgccaagtat gtttatacag  40080
gtggtttctt aaagttctgt ttgtgattat ctcgtcttga gcaaatgagg aaaggatgtg  40140
aagaatctgg tgtccccatg atctcaccca gaaatggttt ggtagttaca aagcaagata  40200
gagcagttga gcaaatactt agcccatcta gtcctctacc actaccacct tcgcctttta  40260
atgagcagga ctttgtagta agcgagttgt tgaaaaggag ctccacatac ttagtaacag  40320
cctcggagcg gatggaaaga agtaggcatt gctgcagagc tgagatgaac ctgcaaggag  40380
acagccttgg ccccagggaa tgatcactgc actgcgcccc ctactggcct ggctgagatg  40440
actagctgtg attccctcct tagtctcacc tgttgaagat ggcgcagaac agttacagcc  40500
atgatcaaaa aagataatta atactttagt gtctcctgcc ctatccgccc ccagggagag  40560
gccagaccat tcagggtgcc agctggaggt tataagggtg gagtgtggag acagtgtttc  40620
gtgtcactac ttcctttttt tttttttttt tttttttttt tgagacagag ttttgctctt  40680
gtcgcccagg ctggagtgcg gtggggcgat ctcggctcac tccaactttc acctcccagg  40740
ttcaagcaat tctcctgcct cagcctgctg aatagctggg attacaggcg cctgccacca  40800
cgcccaacta atttttctat ttttagtaga gagcttcctg atagctgaac atgcagaggc  40860
tgctgggaag ggcatagaat ctctgcagtc cttctcacat accttatcct atgtatctct  40920
tcatctgtat cctttgtaat agccttcata ataaaccggt aaacataagt tagtgtttcc  40980
```

-continued

```
tctagttctg ttaggcaatc tagcaaatca gttgaacaca aggagggggc catgggaccc  41040

tcaatttata gtcattcagt cataacaggt aaaacctggg gcttgcaatt ggcatcggaa  41100

ataaggggc agtcttgtgg gaatgagctc tcaacctgtg agattgaagc agcatggttg  41160

tctggggtaa tacgtgtggt ttgttgcccc acgccaagga aatcgaggat ggggacacaa  41220

aaggagtggg ttcaagagcg gaagtttagc aggcaaaaga aagaagagac cttccctgtg  41280

cagaggaagg agtcccgaac aggtttccgg gtttacagcg agatgcggtt gcttttatag  41340

atgagcttga ggaagcggtg tcttatttac gtagggcaca gaggattggt tggaccaggt  41400

gttccattta catagcacag gaagaggctg gccatcccac cctcatctgt tattatgcaa  41460

atggcacctc tacctagccc aggccttgtt gcctgctttt ttactgcaca cgtggcaaca  41520

aagaaaaggg aaaagggaac ttcaatattg aatatacctg acttccaagt atccctttcc  41580

tattggcaca gctgctggca ttcgcctatg caagcttcca gtttgcttat ctatgtttgc  41640

agcttgagtt ttcaggctct ttttgttaga aaagaaatga tttggggctt ctttttatta  41700

aaaggcaaac cttactgagg actcttttat cctcactaac tgcctaaata aattttgttt  41760

aggtgttgta tcaggatctg atgctatctc caggtagaca gtgtcagaat taaataggag  41820

gatacccaac cagtgtctgc tgcagaattg attgccttct tgttaatggg gagaaatcac  41880

tacgcatttg gtcacagaag tcttctgtgt ttattgttgt ggcatgagag cagaggaaaa  41940

acggtttgag atttttcccc tcaaaaacat aggggaaatc ttcatgatat tggacttggc  42000
```

<210> SEQ ID NO 2
<211> LENGTH: 6099
<212> TYPE: DNA
<213> ORGANISM: Homo sapiens

<400> SEQUENCE: 2

```
aggcggcgcg tgcgtagagg ggcggtgaga gctaagaggg gcagcgcgtg tgcagagggg     60

cggtgtgact taggacgggg cgatggcggc tgagaggagc tgcgcgtgcg cgaacatgta    120

actggtggga tctgcggcgg ctcccagatg atggtcgtcc tcctgggcgc gacgacccta    180

gtgctcgtcg ccgtggcgcc atgggtgttg tccgcagccg caggtggaaa aaatctaaaa    240

tctcctcaaa aagtagaggt cgacatcata gatgacaact ttatcctgag gtggaacagg    300

agcgatgagt ctgtcgggaa tgtgactttt tcattcgatt atcaaaaaac tgggatggat    360

aattggataa aattgtctgg gtgtcagaat attactagta ccaaatgcaa cttttcttca    420

ctcaagctga atgtttatga agaaattaaa ttgcgtataa gagcagaaaa agaaaacact    480

tcttcatggt atgaggttga ctcatttaca ccatttcgca aagctcagat tggtcctcca    540

gaagtacatt tagaagctga agataaggca atagtgatac acatctctcc tggaacaaaa    600

gatagtgtta tgtgggcttt ggatggttta agctttacat atagcttagt tatctggaaa    660

aactcttcag gtgtagaaga aaggattgaa aatatttatt ccagacataa aatttataaa    720

ctctcaccag agactactta ttgtctaaaa gttaaagcag cactacttac gtcatggaaa    780

attggtgtct atagtccagt acattgtata aagaccacag ttgaaaatga actacctcca    840

ccagaaaata tagaagtcag tgtccaaaat cagaactatg ttcttaaatg ggattataca    900

tatgcaaaca tgacctttca agttcagtgg ctccacgcct ttttaaaaag gaatcctgga    960

aaccatttgt ataaatggaa acaaatacct gactgtgaaa atgtcaaaac tacccagtgt   1020

gtctttcctc aaaacgtttt ccaaaaagga atttaccttc tccgcgtaca agcatctgat   1080

ggaaataaca catctttttg gtctgaagag ataaagtttg atactgaaat acaagctttc   1140
```

-continued

```
ctacttcctc cagtctttaa cattagatcc cttagtgatt cattccatat ctatatcggt   1200

gctccaaaac agtctggaaa cacgcctgtg atccaggatt atccactgat ttatgaaatt   1260

attttttggg aaaacacttc aaatgctgag agaaaaatta tcgagaaaaa aactgatgtt   1320

acagttccta atttgaaacc actgactgta tattgtgtga aagccagagc acacaccatg   1380

gatgaaaagc tgaataaaag cagtgttttt agtgacgctg tatgtgagaa aacaaaacca   1440

ggaaatacct ctaaaatttg gcttatagtt ggaatttgta ttgcattatt tgctctcccg   1500

tttgtcattt atgctgcgaa agtcttcttg agatgcatca attatgtctt ctttccatca   1560

cttaaacctt cttccagtat agatgagtat ttctctgaac agccattgaa gaatcttctg   1620

ctttcaactt ctgaggaaca aatcgaaaaa tgtttcataa ttgaaaatat aagcacaatt   1680

gctacagtag aagaaactaa tcaaactgat gaagatcata aaaaatacag ttcccaaact   1740

agccaagatt caggaaatta ttctaatgaa gatgaaagcg aaagtaaaac aagtgaagaa   1800

ctacagcagg actttgtatg accagaaatg aactgtgtca agtataaggt ttttcagcag   1860

gagttacact gggagcctga ggtcctcacc ttcctctcag taactacaga gaggacgttt   1920

ccctgtttag ggaaagaaaa aacatcttca gatcataggt cctaaaaata cgggcaagct   1980

cttaactatt taaaaatgaa attacaggcc cgggcacggt ggctcacacc tgtaatccca   2040

gcactttggg aggctgaggc aggcagatca tgaggtcaag agatcgagac cagcctggcc   2100

aacgtggtga aaccccatct ctactaaaaa tacaaaaatt agccgggtgt ggtggcgcgc   2160

gcctgttgtc ttagctactc aggaggctga ggcaggagaa tcgcttgaaa acaggaggtg   2220

gaggttgcag tgagccgaga tcacgccact gcactccagc ctggtgacag cgtgagactc   2280

tttaaaaaaa gaaattaaaa gagttgagac aaacgtttcc tacattcttt tccatgtgta   2340

aaatcatgaa aaagcctgtc accggacttg cattggatga gatgagtcag accaaaacag   2400

tggccacccg tcttcctcct gtgagcctaa gtgcagccgt gctagctgcg caccgtggct   2460

aaggatgacg tctgtgttcc tgtccatcac tgatgctgct ggctactgca tgtgccacac   2520

ctgtctgttc gccattccta acattctgtt tcattcttcc tcgggagata tttcaaacat   2580

ttggtctttt cttttaacac tgagggtagg cccttaggaa atttatttag gaaagtctga   2640

acacgttatc acttggtttt ctggaaagta gcttacccta gaaaacagct gcaaatgcca   2700

gaaagatgat ccctaaaaat gttgagggac ttctgttcat tcatcccgag aacattggct   2760

tccacatcac agtatctacc cttacatggt ttaggattaa agccaggcaa tcttttacta   2820

tgcattaaga cctctgattc aaaacttatt agaacagtag cttctgctgg aatttgcaat   2880

cactgaagtc atagaaaata ggtaactatc taattagaga aataattgtt gtattttaag   2940

atctgagagt gtgtacaagt tttagtatac atgccatgcc agaagatagt gtatgcaaga   3000

agtcttggga ccagaaaatg gcaatgatag gagactgaca tagaagaaga atgcttccct   3060

aggaaaaagg tcgctggctt tggtgcaaga ggaagaagaa tgttccactg gaagcctgag   3120

cacctaatca gctctcagtg atcaacccac tcttgttatg ggtggtctct gtcactttga   3180

atgccaggct ggcttctcgt ctagcagtat tcagataccc cttctgctca gcctgcttgg   3240

cgttaaaata caaatcattg aactgagggg gaaaaatgta actaggaaga aaaacccaat   3300

ttaagaaatt acataatgct ttccaaaggc acctacaact tagttttaaa ttacttgcta   3360

ctggggatta cccatggata tccttaatag gcaggaagtc tgggaattct ggtggcctct   3420

agggcagtgt tctcacagca ccgttccgac agggaccagt gaaagaaaag agacaaagtt   3480

agaacgtgct ggggagcggc catttctaag gccagtctgg tttaagtagt catttctgct   3540
```

-continued gaaaaaacag atgatcctgg tggaagaaaa ggttgaaggc agctgccctc gggagggctg 3600
tgatgctcgg cacatcctgc ctggcacata cacgtgtctg caggccacac cgtgcatgtc 3660
cccagacctg ccgcctggct tctggagtgc ttcaagcaga gcatggtggg tcattgagga 3720
gacccaggaa tctcatctga gaacccactc tctgccggag aaccccatgg tgacacattt 3780
tcatctttct gaccagaggc tgtttttttt ttttttgag acagtctcat tctgttgccc 3840
aggctggagt gcagtggctt gatctcggct cactgcaacc tcgcctcccg ggttcaagca 3900
attctctgcc gcagcctcca gagtagctgg gataacaggt gcccaccacc acaccccact 3960
aatttttgta tttgtatttt tagtagagat ggggtttcac catgttggtc aggctggtct 4020
tggactcctg acctcatgct ccacccgctt cggcctccca aagttctggg attacaggtg 4080
tgagccaccg tgcacggccg gcctgacctt tggaaaagcc ttgtcacttt ggacgtttgc 4140
gtctttgaag aggcgatggg agcatatcat gactgcctgc caccattgct tttcagacta 4200
ccacaactca atcatgctgt ccaggacttc tggccctgtg ttcaccactg ggaaaacgta 4260
cttcagactg gatagcctaa aaaggagcaa tgcccttgta ggatgtggag aagggaaaat 4320
acggacatta acattaaaag acaccagtga aattgttagg tctctaggaa gttggagcac 4380
aaggcttcac gctttaagac catctgtggt tttcagtgaa caagcgctga gcaccagcag 4440
cagaaaacaa caacaaaaaa acacctcgtt tttaccttgt cttctagaca tgaaaaggca 4500
gttgcattcc actctgcatt atgttctaca tgttgcttta tcagtatatg cttagctgta 4560
agtgacaagt atttttctg aacagaagtt tacttagaaa taccatgcac ttgggggtac 4620
caattaaccg cctgaaaatt agcatattga tagttcttag agagaccaga tataatctaa 4680
gaatttatat gaaagatttg tatcattaga gccagaaata attttatatt aatatataat 4740
acagattaac attatatata atatgtacct gtgtcacttc tgacatgagc ctgtaaacat 4800
atattcatat atgtacctgc acatgtaccc acctgatgta ggtcttattc ctttagtatg 4860
gacttaaagt acttattcat ataccttgta actaaaaatt agaacagctc cctagaattg 4920
tgaactttta agagtctgac tagaaatttg caacttataa aaaagttact tttaaaaata 4980
taagttaggg ctaggcacag tggctcatgc ctataatctc agcacttttg ggaggccaag 5040
acaggaggat cacttcaggc caggagttca agatcaacca acctgggtaa catggccaga 5100
ccccatctct atttatatat atatatataa aacttagagt ttttatcttc ccctaaaaga 5160
ggccgtgata tttgcagcag cctcaaattg ctcttaaggg gtttaggtgt gcagaagctt 5220
tcctttccct acccagtaac catgtgacta ctaacgtggt atattgattt attttgtttg 5280
ctgtctgtct cccctgcccc actgctggaa cagaggctcc aagaaaacag ggaccttatt 5340
attcattact gcatccccag taatgaaagt acttagaaaa taattattga atgaatgaaa 5400
tctaaactgt gaacctgagg gtgtttgtgg cagtgtttgt tttactgaat tgtagaagga 5460
cataaccgtg ttttcagtgt ttctatggaa caaacttgta cattttattt cacttgtgtt 5520
ttgtcttaaa ccctactgct ggaaacaatt ttatgtaata agcaatgggc ccaaaagtct 5580
aggagttttt ttgtacttag tgaatttgta tgcaacagag atgctgcagc tgatgccttt 5640
aaaaggtatt catcatggaa gagctgaggc ctgtgcttgg tgttccagag cccagggttg 5700
agcatcctga aggagccact gcagccgtca ctgtccccag agcctgtgga gatagagcct 5760
gtttgctgct ttttcttccc gctcttaaga catggctgga gctcagtctt cattgaatga 5820
agtttgctgt ggtattgcat agccttgctt tcttgaacta aactgtttgc ccttcacaag 5880
tagttcttct ttcaggatta gttcgttcca aggaggctct tcagtctcac agataagtag 5940

-continued atctctcctg ctgtctggac acatttcact cggaaattga atacaatttg tattcaggct 6000
gggaacctga acacacactt gtgtttttaa gcttcccttt tttacagtgg acaaggacac 6060
aaataataaa taaatcatcc ctaatgccca agaaaaaaa 6099

<210> SEQ ID NO 3
<211> LENGTH: 22
<212> TYPE: DNA
<213> ORGANISM: Artificial sequence
<220> FEATURE:
<223> OTHER INFORMATION: Primer

<400> SEQUENCE: 3
ggaactgagg ccatgattaa ga 22

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
acctccgact ttcgttcttg 20

<210> SEQ ID NO 5
<211> LENGTH: 23
<212> TYPE: DNA
<213> ORGANISM: Artificial sequence
<220> FEATURE:
<223> OTHER INFORMATION: Probe

<400> SEQUENCE: 5
aagacggacc agagcgaaag cat 23

<210> SEQ ID NO 6
<211> LENGTH: 21
<212> TYPE: DNA
<213> ORGANISM: Artificial sequence
<220> FEATURE:
<223> OTHER INFORMATION: Primer

<400> SEQUENCE: 6
ctttcaagtt cagtggctcc a 21

<210> SEQ ID NO 7
<211> LENGTH: 22
<212> TYPE: DNA
<213> ORGANISM: Artificial sequence
<220> FEATURE:
<223> OTHER INFORMATION: Primer

<400> SEQUENCE: 7
cgttttgagg aaagacacac tg 22

<210> SEQ ID NO 8
<211> LENGTH: 35
<212> TYPE: DNA
<213> ORGANISM: Artificial sequence
<220> FEATURE:
<223> OTHER INFORMATION: Probe

<400> SEQUENCE: 8
agttttgaca ttttcacagt caggtatttg tttcc 35

-continued

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
tttatccaat tatccatccc 20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
tcgcctaatt tttctctcac 20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
ctttttctgc tcttatacgc 20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
ctgttttaca ttttttttcc 20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
tttcatattt gttacttcct 20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
ttcgcctaat ttttctctca 20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide -continued
<400> SEQUENCE: 15
tttgcatatg tataatccca 20

COMPOUNDS AND METHODS FOR REDUCING IFNAR1 EXPRESSION

SEQUENCE LISTING

The present application is being filed along with a Sequence Listing in electronic format. The Sequence Listing is provided as a file entitled BIOL0386USSEQ_ST25.txt, created on Jun. 13, 2022 which is 64 KB in size. The information in the electronic format of the sequence listing is incorporated herein by reference in its entirety.

FIELD

Provided are oligomeric compounds, methods, and pharmaceutical compositions for reducing the amount or activity of IFNAR1 RNA in a cell or animal, and in certain instances reducing the amount of IFNAR1 protein in a cell or animal Such oligomeric compounds, methods, and pharmaceutical compositions are useful to treat neurological diseases or conditions associated with neuroinflammation, including Aicardi-Goutières Syndrome, stroke, neuropsychiatric systemic lupus erythematosus, neuroinflammation following traumatic brain injury, neuro-autoimmune disorders, Alzheimer's disease, post-operative delirium and cognitive decline, cranial radiation-induced cognitive decline, viral infection-induced cognitive decline, neuromyelitis optica, and ataxia telangiectasia.

BACKGROUND

Aicardi-Goutières Syndrome (AGS) is a progressive inflammatory encephalopathy associated with several neuropathological manifestations, including seizures, difficulty feeding, dystonia, spasticity, delayed motor development, delayed language development, and delayed social skill development. Imaging of AGS patients reveals white matter abnormalities, T cell infiltration, B cell infiltration, striatal necrosis, brain atrophy, basal ganglia calcification, and microencephaly; patients also have elevated levels of interferon alpha (IFNa) and lymphocytosis in cerebrospinal fluid. AGS has been associated with mutations in one of ten genes: TREX1 (DNA exonuclease), RNASEH2A, B or C (subunits of RNASEH2), SAMHD1 (dNTP hydrolase), ADAR1 (RNA editing enzyme), MDA5 (dsRNA sensor), USP18 (negative regulator of type I IFN signaling), LSM11 and RNU7-1 (components of the replication-dependent histone pre-mRNA—processing complex). Mutations in any one of these genes lead to aberrant activation of the antiviral response and high levels of IFNa (Adang, et al., 2020, J. Child Neurol., 35, 7016; Rodero, et al., 2016, J. Esp. Med., 213, 2527-2538).

Interferon Alpha and Beta Receptor Subunit 1 (IFNAR1) is one of two components of the interferon alpha receptor, involved in type I interferon signaling Type I interferon signaling is elevated in AGS patients and is believed to be a key mediator of neuropathology. Elevated levels of type I interferon signaling are also associated with diseases or conditions such as neuroinflammation associated with stroke, brain injury, Alzheimer's disease, neuropsychiatric systemic lupus erythematosus, neuromyelitis optica, post-operative delirium and cognitive decline, cranial radiation-induced cognitive decline, viral infection-induced cognitive decline, and ataxia telangectasia (Wlodarczyk, et al., 2021, Glia 69, 943-953; Santer, et al., 2009, J. Immunol. 182, 1192-1201; Zeng, et al., 2019, Arthritis Res. Ther. 21, 205.017; Karageorgas, et al., 2011, J Biomed Biotechnol 2011, 273907; Roy, et al., 2020, J Clin Invest. 130, 1912-1930; Witcher, 2021, J. Neurosci. JN-RM-2469-2420; Blank, et al., 2016, Immunity 44, 901-912; Härtlova, et al., 2015, Immunity 44, 901-912; McDonugh, et al., 2017, J Neurosci. 37, 8292-8308). Over-expression of IFNa in transgenic mice leads to elevated levels of type I interferon signaling, resulting in neurodegenerative changes, T cell infiltration, B cell infiltration, microglial cell activation, reactive astrocytosis, activation of endothelial cells, and calcification of the thalamus and cerebellum (Hofer, et al., 2013*, Cytokine & Growth Factor Reviews* 24, 257-267; Klok, et al., 2015*, Ann. Clin. Transl. Neurol.,* 2, 774-779). Type I interferon signaling induces expression of hundreds of genes, including Interferon Induced Protein with Tetratricopeptide Repeats 1 (Ifit1), Interferon Induced Protein with Tetratricopeptide Repeats 3 (Ifit 3), and Interferon Regulatory Factor 7 (Irf7) (Li, et al., 2018*, J. Biol. Chem.* 292, P5845-P5859). Crossing a mouse model of Alzheimer's disease with an IFNAR1 knockout mouse suppressed type I interferon signaling, resulted in a glial cell anti-inflammatory response, and reduced neuroinflammation (Minter, M. R., et al., 2016*, Acta Neuropathologica Commun.* 4:72).

SUMMARY

Oligomeric compounds, methods, and pharmaceutical compositions of certain embodiments described herein are useful for reducing or inhibiting IFNAR1 expression in a cell or animal. In certain embodiments, IFNAR1 RNA or protein levels can be reduced in a cell or animal. In certain embodiments, the subject has Aicardi-Goutières Syndrome. In certain embodiments, the subject has a disease or disorder associated with a mutation in TREX1, RNASEH2A, RNASEH2B, RNASEH2C, SAMHD1, ADAR1, MDA5, USP18, LSM11, or RNU7-1.

Also provided are methods of treating a disease or disorder associated with elevated type I interferon signaling, in certain embodiments, the disease or disorder is AGS, stroke, epilepsy, neuroinflammation following traumatic brain injury, neuro-autoimmune disorders, Alzheimer's disease, post-operative delirium and cognitive decline, cranial radiation-induced cognitive decline, viral infection-induced cognitive decline, neuromyelitis optica or ataxia telangectasia.

DETAILED DESCRIPTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Where permitted, all patents, applications, published applications and other publications and other data referred to throughout in the disclosure are incorporated by reference herein in their entirety.

Unless otherwise indicated, the following terms have the following meanings:

As used herein, "2'-deoxynucleoside" means a nucleoside comprising a 2'-H(H) deoxyfuranosyl sugar moiety. In certain embodiments, a 2'-deoxynucleoside is a 2'-β-D-deoxynucleoside and comprises a 2'13-D-deoxyribosyl sugar moiety, which has the β-D ribosyl configuration as found in naturally occurring deoxyribonucleic acids (DNA). In certain embodiments, a 2'-deoxynucleoside may comprise a modified nucleobase or may comprise an RNA nucleobase (uracil).

As used herein, "2'-MOE" means a 2'-$O(CH_2)_2OCH_3$ group in place of the 2'—OH group of a furanosyl sugar moiety. A "2'-MOE sugar moiety" or a "2'-O-methoxyethyl sugar moiety" means a sugar moiety with a 2'-$O(CH_2)_2OCH_3$ group in place of the 2'—OH group of a furanosyl sugar moiety. Unless otherwise indicated, a 2'-MOE sugar moiety is in the β-D-ribosyl configuration. "MOE" means O-methoxyethyl.

As used herein, "2'-MOE nucleoside" means a nucleoside comprising a 2'-MOE sugar moiety.

As used herein, "5-methylcytosine" means a cytosine modified with a methyl group attached to the 5 position. A 5-methylcytosine is a modified nucleobase.

As used herein, "ameliorate" in reference to a treatment means improvement in at least one symptom or hallmark relative to the same symptom or hallmark in the absence of the treatment. In certain embodiments, amelioration is the reduction in the severity or frequency of a symptom or hallmark or the delayed onset or slowing of progression in the severity or frequency of a symptom or hallmark. In certain embodiments, the symptom or hallmark is one or more of seizures, difficulty feeding, dystonia, spasticity, delayed motor development, delayed language development, delayed social skill development, white matter abnormalities, T cell infiltration, B cell infiltration, striatal necrosis, brain atrophy, basal ganglia calcification, and microencephaly. In certain embodiments, the hallmark is the level of IFNa or lymphocytosis in cerebrospinal fluid in the subject.

As used herein, "population" means a plurality of molecules of identical molecular formula.

As used herein, "chirally enriched" in reference to a population means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom as defined herein. Chirally enriched populations of molecules having multiple chiral centers within each molecule may contain one or more stereorandom chiral centers. In certain embodiments, the molecules are modified oligonucleotides. In certain embodiments, the molecules are oligomeric compounds comprising modified oligonucleotides. In certain embodiments, the chiral center is at the phosphorous atom of a phosphorothioate internucleoside linkage. In certain embodiments, the chiral center is at the phosphorous atom of a mesyl phosphoramidate internucleoside linkage.

As used herein, "chirally controlled" in reference to an internucleoside linkage means chirality at that linkage is enriched for a particular stereochemical configuration.

As used herein, "antisense agent" means an antisense compound and optionally one or more additional features, such as a sense compound. Although RNAis are not claimed, my thinking behind keeping it in was in the event we needed basis to distinguish our compounds from an siRNA sequence.

As used herein, "cerebrospinal fluid" or "CSF" means the fluid filling the space around the brain and spinal cord. "Artificial cerebrospinal fluid" or "aCSF" means a prepared or manufactured fluid that has certain properties (e.g., osmolarity, pH, and/or electrolytes) similar to cerebrospinal fluid and is biocompatible with CSF.

As used herein, "conjugate group" means a group of atoms that is directly attached to an oligonucleotide. Conjugate groups include a conjugate moiety and a conjugate linker that attaches the conjugate moiety to the oligonucleotide.

As used herein, "conjugate linker" means a single bond or a group of atoms comprising at least one bond that connects a conjugate moiety to an oligonucleotide.

As used herein, "conjugate moiety" means a covalently bound group of atoms that modifies one or more properties of a molecule compared to the identical molecule lacking the conjugate moiety, including but not limited to pharmacodynamics, pharmacokinetics, stability, binding, absorption, tissue distribution, cellular distribution, cellular uptake, charge, and clearance.

As used herein, "deoxy region" means a region of 5-12 contiguous nucleotides, wherein at least 70% of the nucleosides comprise a β-D-2'-deoxyribosyl sugar moiety. In certain embodiments, a deoxy region is the gap of a gapmer.

As used herein, "internucleoside linkage" is the covalent linkage between adjacent nucleosides in an oligonucleotide. As used herein "modified internucleoside linkage" means any internucleoside linkage other than a phosphodiester internucleoside linkage.

As used herein, "linked nucleosides" are nucleosides that are connected in a contiguous sequence (i.e., no additional nucleosides are presented between those that are linked).

As used herein, "motif" means the pattern of unmodified and/or modified sugar moieties, nucleobases, and/or internucleoside linkages, in an oligonucleotide.

As used herein, "modified nucleoside" means a nucleoside comprising a modified nucleobase and/or a modified sugar moiety.

As used herein, "non-bicyclic modified sugar moiety" means a modified sugar moiety that comprises a modification, such as a substituent, that does not form a bridge between two atoms of the sugar to form a second ring.

As used herein, "nucleobase" means an unmodified nucleobase or a modified nucleobase. A nucleobase is a heterocyclic moiety. As used herein an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one other nucleobase. A "5-methyl cytosine" is a modified nucleobase. A universal base is a modified nucleobase that can pair with any one of the five unmodified nucleobases.

As used herein, "nucleobase sequence" means the order of contiguous nucleobases in a nucleic acid or oligonucleotide independent of any sugar or internucleoside linkage modification.

As used herein, "nucleoside" means a compound or fragment of a compound comprising a nucleobase and a sugar moiety. The nucleobase and sugar moiety are each, independently, unmodified or modified.

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to an animal Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water, sterile saline, sterile buffer solution or sterile artificial cerebrospinal fluid.

As used herein "pharmaceutically acceptable salts" means physiologically and pharmaceutically acceptable salts of compounds. Pharmaceutically acceptable salts retain the desired biological activity of the parent compound and do not impart undesired toxicological effects thereto.

As used herein "pharmaceutical composition" means a mixture of substances suitable for administering to a subject. For example, a pharmaceutical composition may comprise an oligomeric compound and a sterile aqueous solution. In certain embodiments, a pharmaceutical composition shows activity in free uptake assay in certain cell lines.

As used herein, "stereorandom" or "stereorandom chiral center" in the context of a population of molecules of identical molecular formula means a chiral center that is not controlled during synthesis, or enriched following synthesis, for a particular absolute stereochemical configuration. The stereochemical configuration of a chiral center is random when it is the result of a synthetic method that is not designed to control the stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. In certain embodiments, the stereorandom chiral center is not racemic because one absolute configuration predominates following synthesis, e.g., due to the action of non-chiral reagents near the enriched stereochemistry of an adjacent sugar moiety. In certain embodiments, the stereorandom chiral center is at the phosphorous atom of a stereorandom phosphorothioate or mesyl phosphoroamidate internucleoside linkage.

As used herein, "sugar moiety" means an unmodified sugar moiety or a modified sugar moiety. As used herein, "unmodified sugar moiety" means a 2'-OH(H) ribosyl moiety, as found in RNA (an "unmodified RNA sugar moiety"), or a 2'-H(H) deoxyribosyl sugar moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "symptom or hallmark" means any physical feature or test result that indicates the existence or extent of a disease or disorder. In certain embodiments, a symptom is apparent to a subject or to a medical professional examining or testing said subject. In certain embodiments, a hallmark is apparent upon invasive diagnostic testing, including, but not limited to, post-mortem tests. In certain embodiments, a hallmark is apparent on a brain MRI scan.

As used herein, "target nucleic acid" and "target RNA" mean a nucleic acid that an oligomeric compound is designed to affect. Target RNA means an RNA transcript and includes pre-mRNA and mRNA unless otherwise specified.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "gapmer" means a modified oligonucleotide comprising an internal region positioned between external regions having one or more nucleosides, wherein the nucleosides comprising the internal region are chemically distinct from the nucleoside or nucleosides comprising the external regions, and wherein the modified oligonucleotide supports RNAse H cleavage. The internal region may be referred to as the "gap" and the external regions may be referred to as the "wings." In certain embodiments, the internal region is a deoxy region. The positions of the internal region or gap refer to the order of the nucleosides of the internal region and are counted starting from the 5'-end of the internal region. Unless otherwise indicated, "gapmer" refers to a sugar motif. In certain embodiments, each nucleoside of the gap is a 2'-β-D-deoxynucleoside. As used herein, the term "MOE gapmer" indicates a gapmer having a gap comprising 2'-β-D-deoxynucleosides and wings comprising 2'-MOE nucleosides. Unless otherwise indicated, a gapmer may comprise one or more modified internucleoside linkages and/or modified nucleobases and such modifications do not necessarily follow the gapmer pattern of the sugar modifications.

As used herein, "hybridization" means the annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

As used herein, "RNAi agent" means an antisense agent that acts, at least in part, through RISC or Ago2 to modulate a target nucleic acid and/or protein encoded by a target nucleic acid. RNAi agents include, but are not limited to double-stranded siRNA, single-stranded RNAi (ssRNAi), and microRNA, including microRNA mimics RNAi agents may comprise conjugate groups and/or terminal groups. In certain embodiments, an RNAi agent modulates the amount and/or activity, of a target nucleic acid. The term RNAi agent excludes antisense agents that act through RNase H.

As used herein, "RNase H agent" means an antisense agent that acts through RNase H to modulate a target nucleic acid and/or protein encoded by a target nucleic acid. In certain embodiments, RNase H agents are single-stranded. In certain embodiments, RNase H agents are double-stranded. RNase H compounds may comprise conjugate groups and/or terminal groups. In certain embodiments, an RNase H agent modulates the amount and/or activity of a target nucleic acid. The term RNase H agent excludes antisense agents that act principally through RISC/Ago2.

As used herein, "treating" means improving a subject's disease or condition by administering an oligomeric compound described herein. In certain embodiments, treating a subject improves a symptom relative to the same symptom in the absence of the treatment. In certain embodiments, treatment reduces in the severity or frequency of a symptom, or delays the onset of a symptom, slows the progression of a symptom, or slows the severity or frequency of a symptom.

As used herein, "therapeutically effective amount" means an amount of a pharmaceutical agent or composition that provides a therapeutic benefit to an animal. For example, a therapeutically effective amount improves a symptom of a disease.

CERTAIN EMBODIMENTS

Embodiment 1. A modified oligonucleotide according to the following chemical structure:

(SEQ ID NO 10)

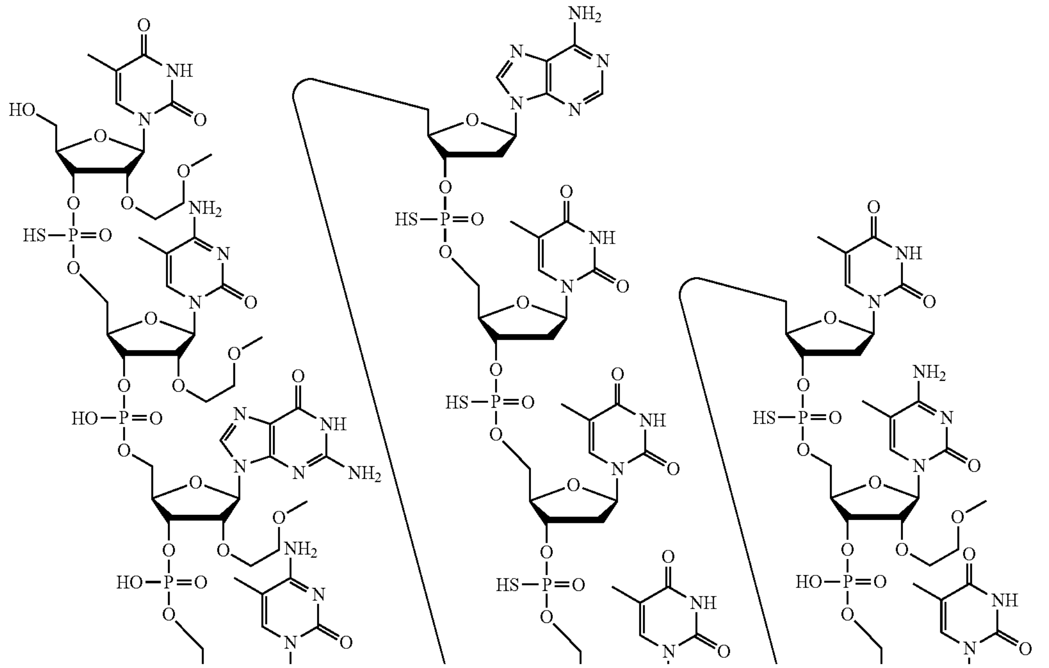

-continued
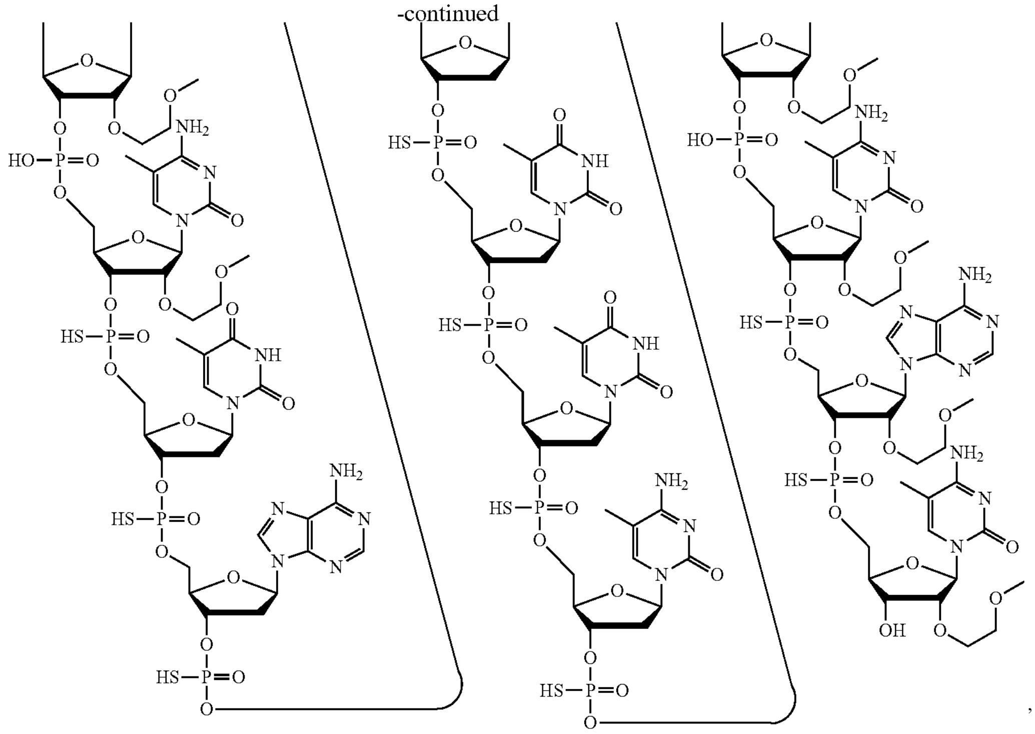
,
or a salt thereof.
Embodiment 2. The modified oligonucleotide of embodiment 1, which is the sodium salt or the potassium salt.
Embodiment 3. A modified oligonucleotide according to the following chemical structure:
(SEQ ID NO 10)
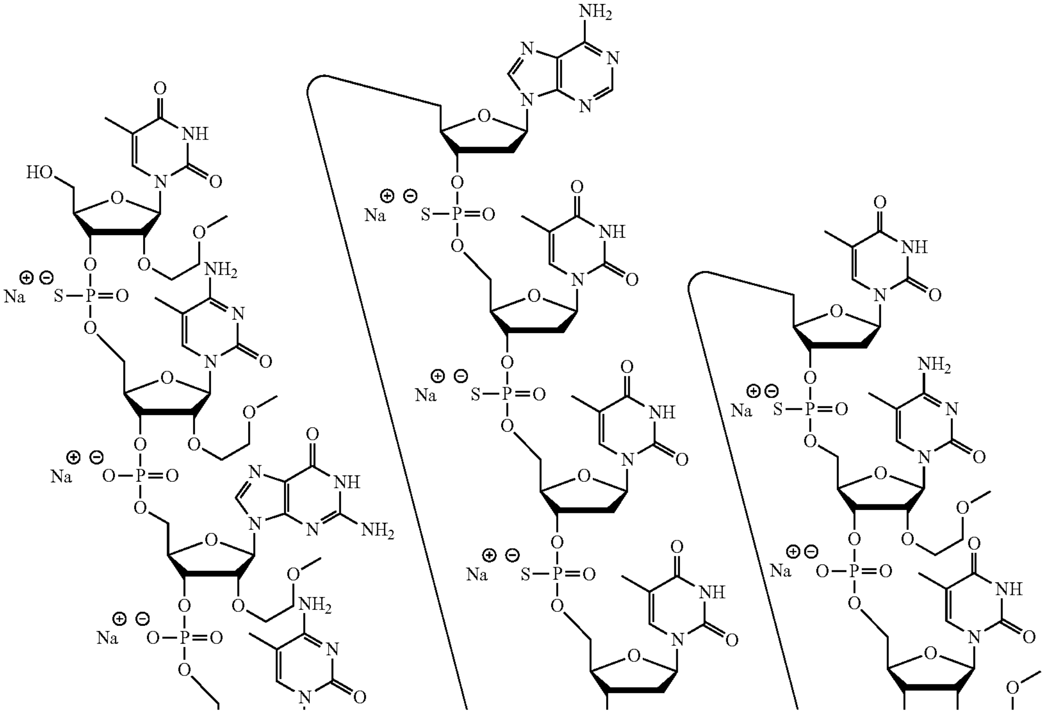

-continued
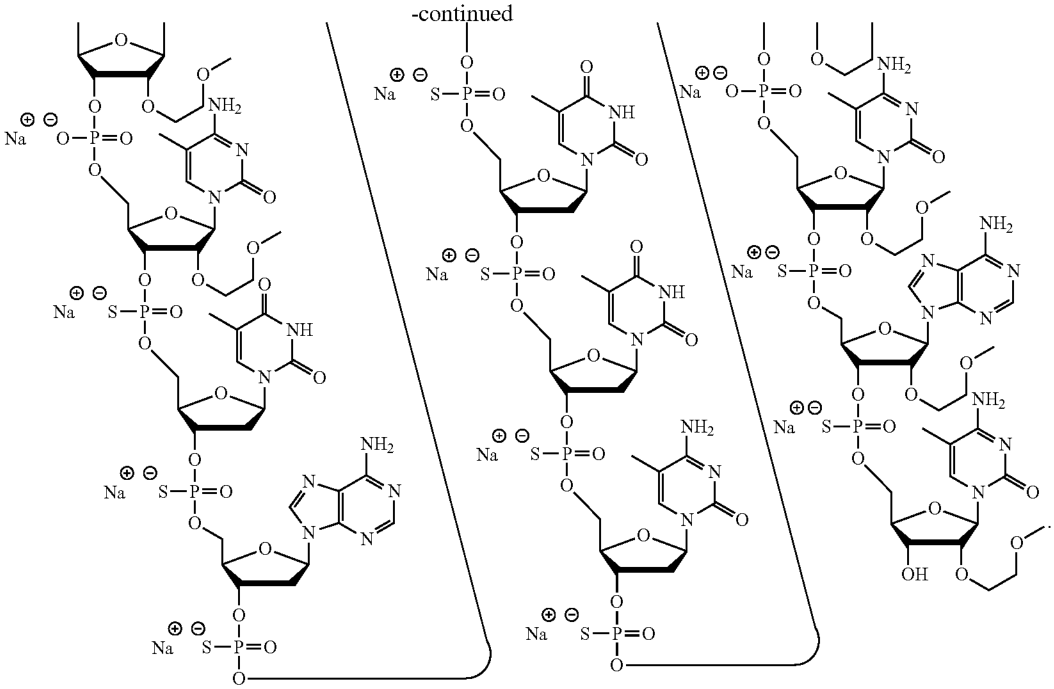
Embodiment 4. A modified oligonucleotide according to the following chemical structure:
(SEQ ID NO 11)
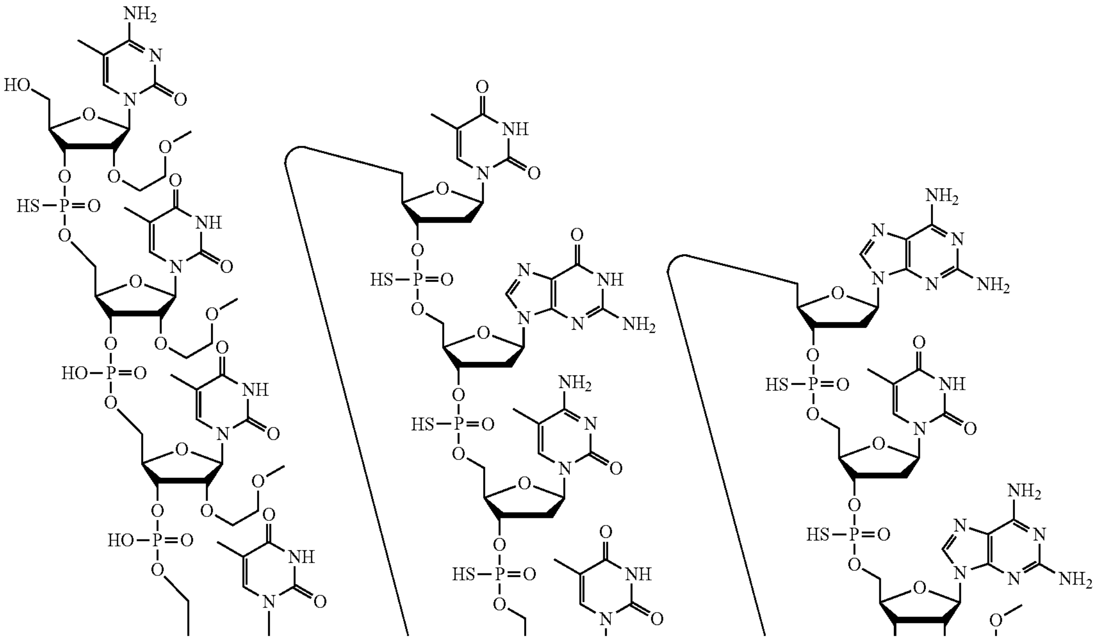

-continued
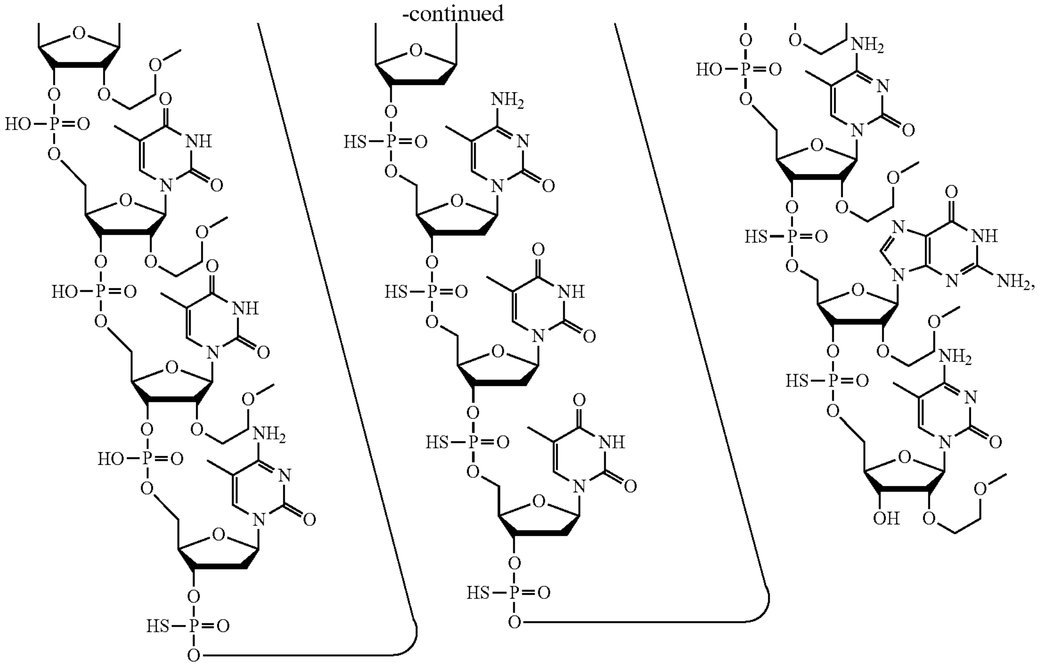
or a salt thereof.
Embodiment 5. The modified oligonucleotide of embodiment 4, which is the sodium salt or the potassium salt.
Embodiment 6. A modified oligonucleotide according to the following chemical structure:
(SEQ ID NO 11)
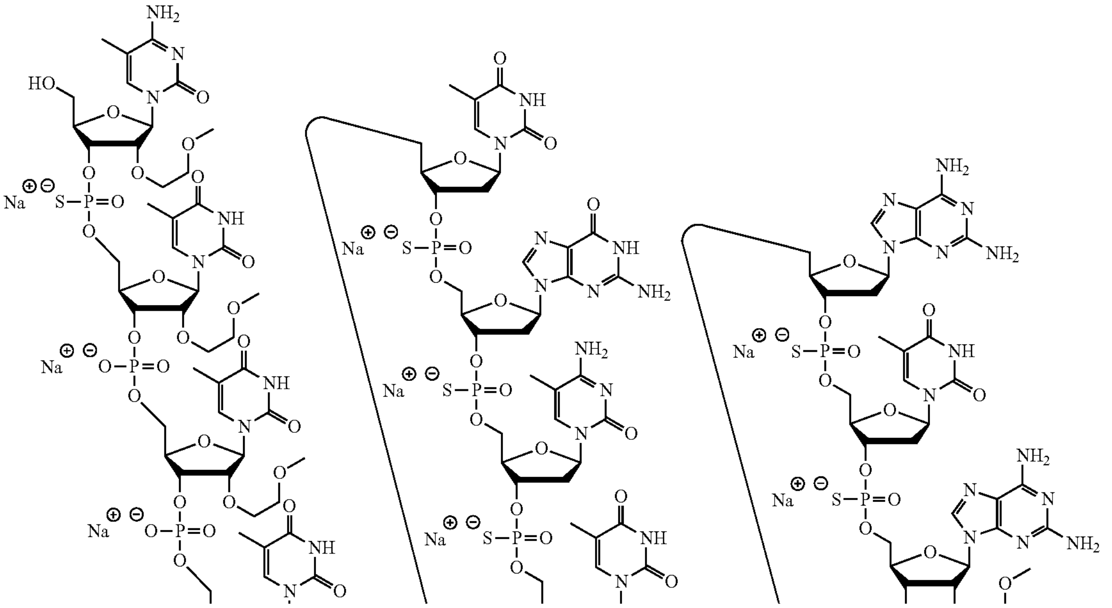

-continued
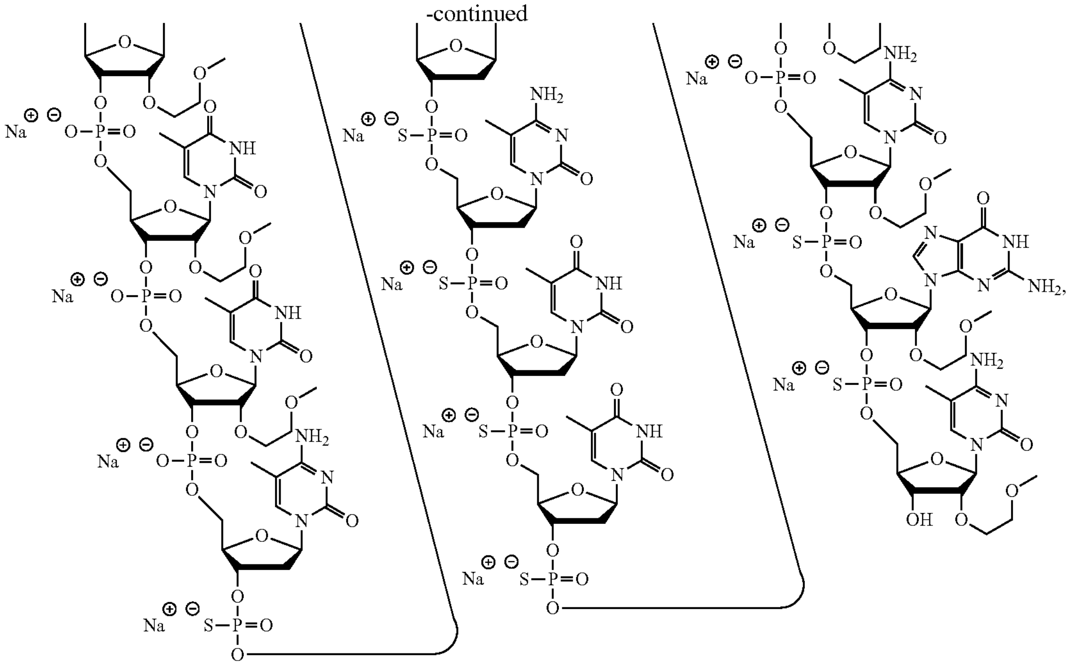
Embodiment 7. A modified oligonucleotide according to the following chemical structure:
(SEQ ID NO 12)
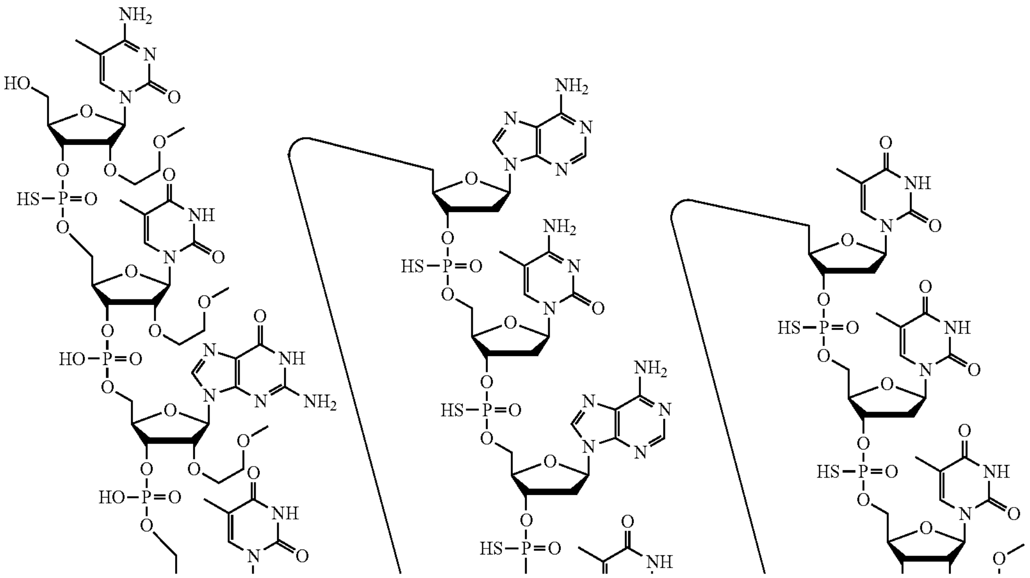

-continued
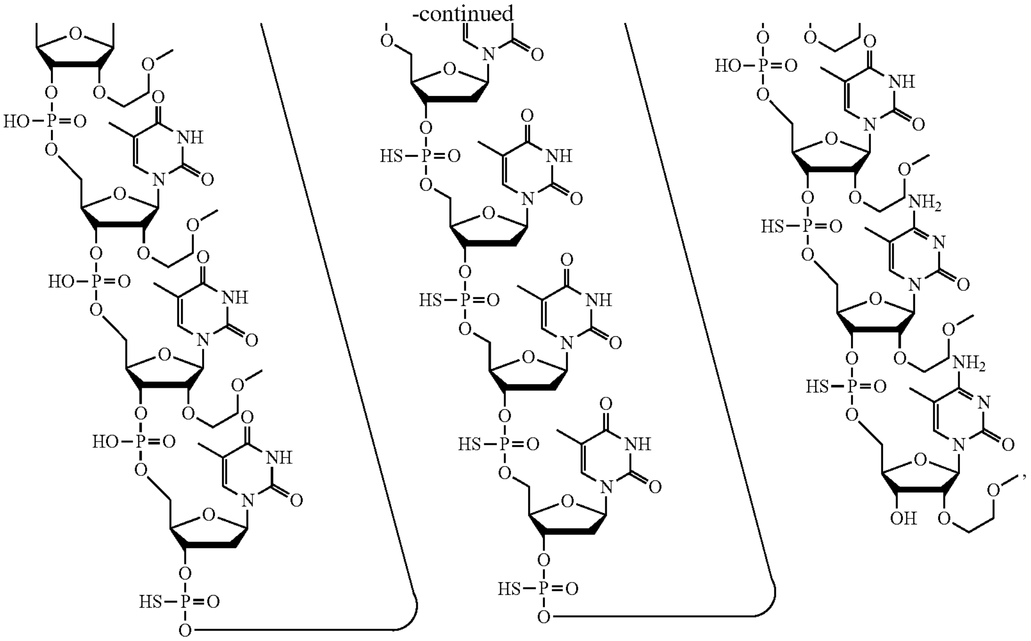
or a salt thereof.
Embodiment 8. The modified oligonucleotide of embodiment 7, which is the sodium salt or the potassium salt.
Embodiment 9. A modified oligonucleotide according to the following chemical structure:
(SEQ ID NO 12)
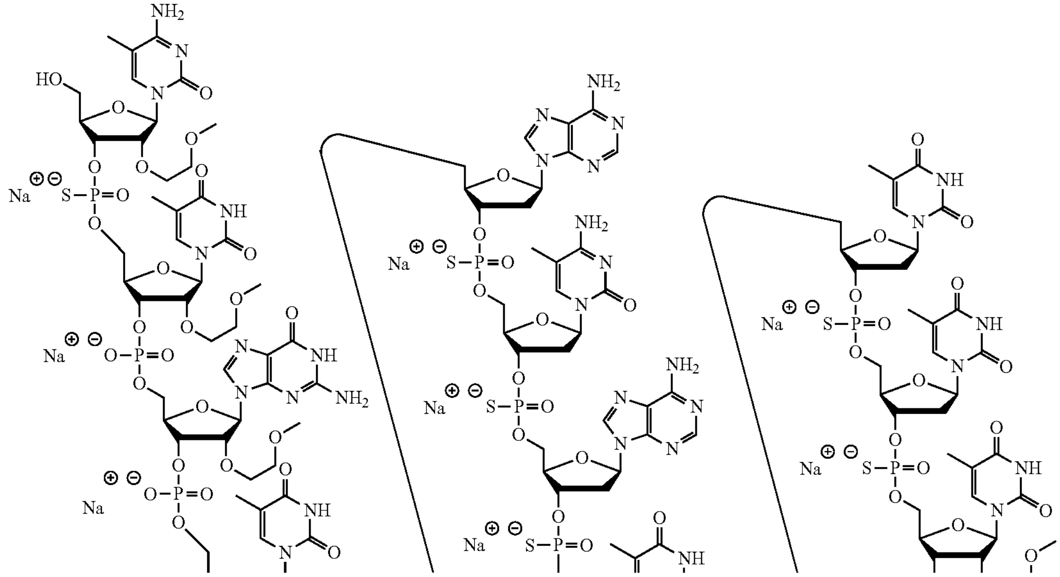

-continued
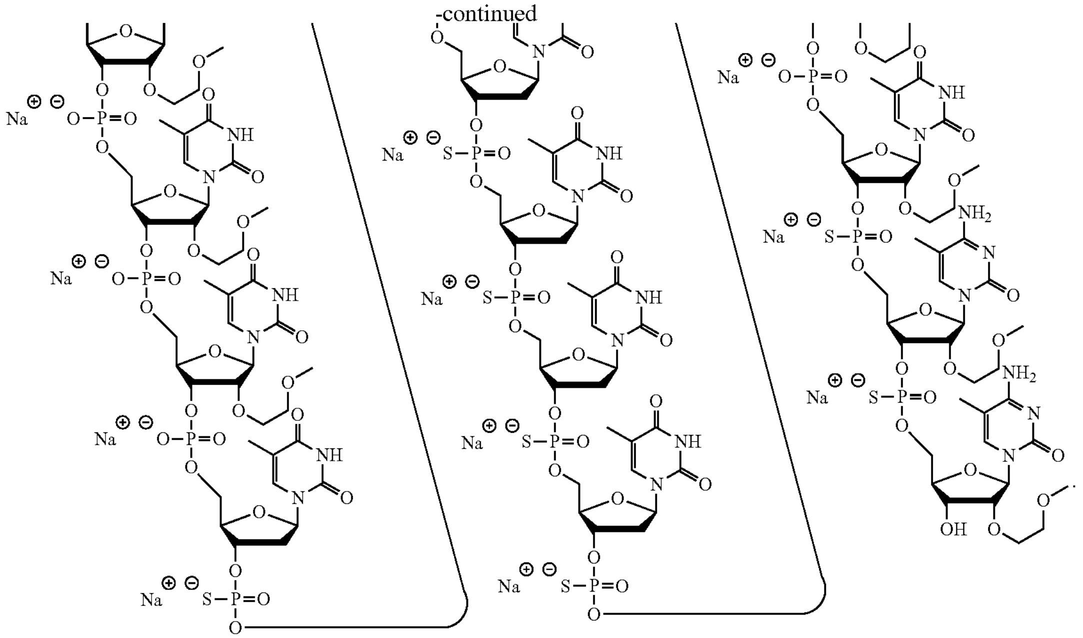
Embodiment 10. A modified oligonucleotide according to the following chemical structure:
(SEQ ID NO 9)
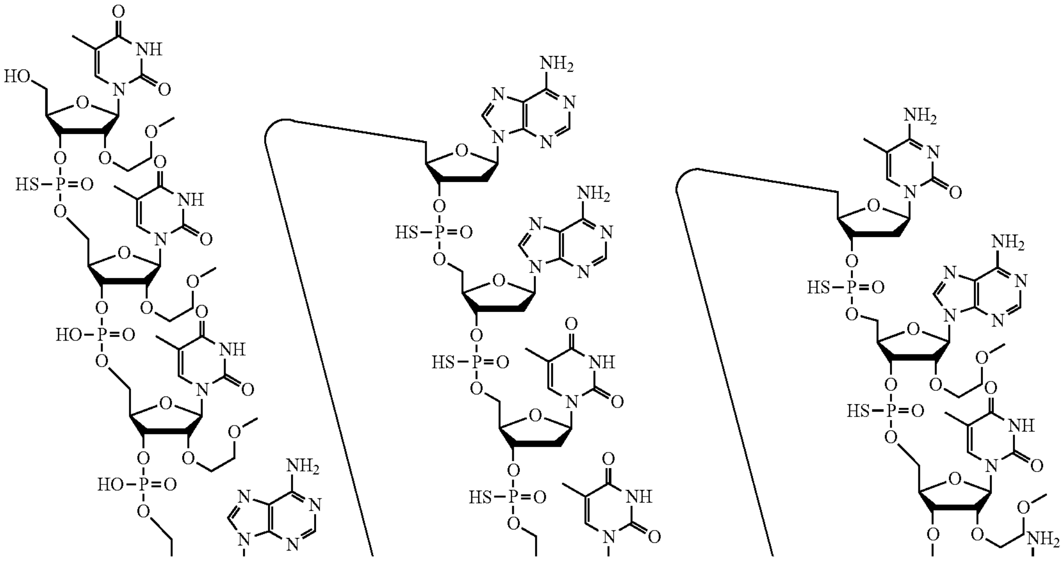

-continued
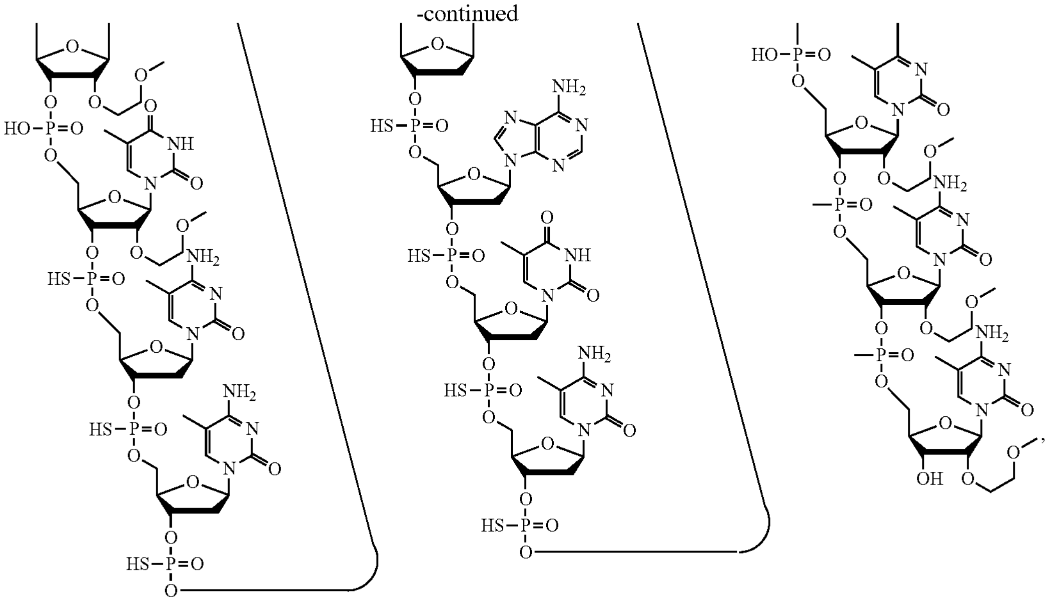
or a salt thereof.
Embodiment 11. The modified oligonucleotide of embodiment 10, which is the sodium salt or the potassium salt.
Embodiment 12. A modified oligonucleotide according to the following chemical structure:
(SEQ ID NO 9)
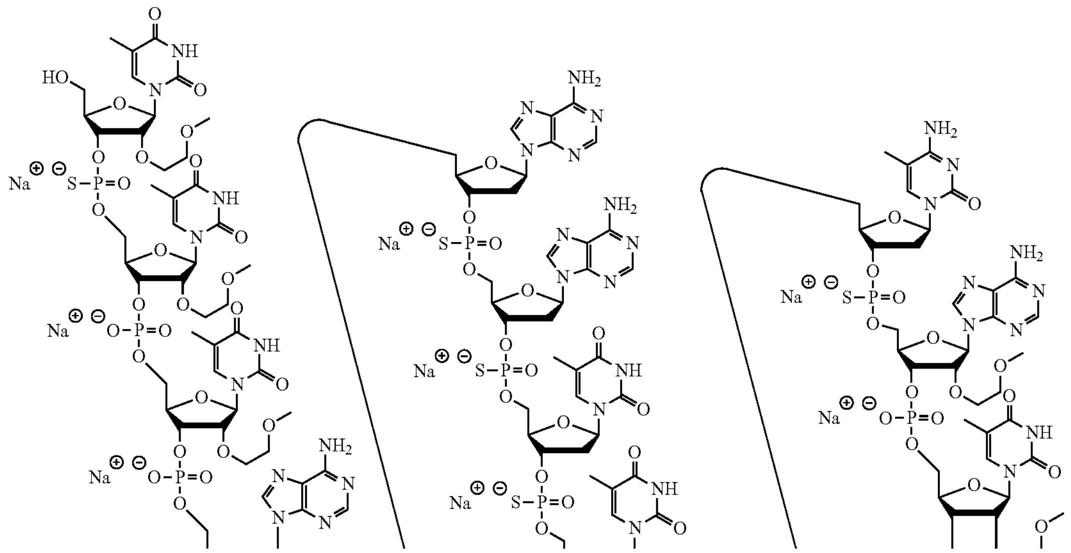

-continued
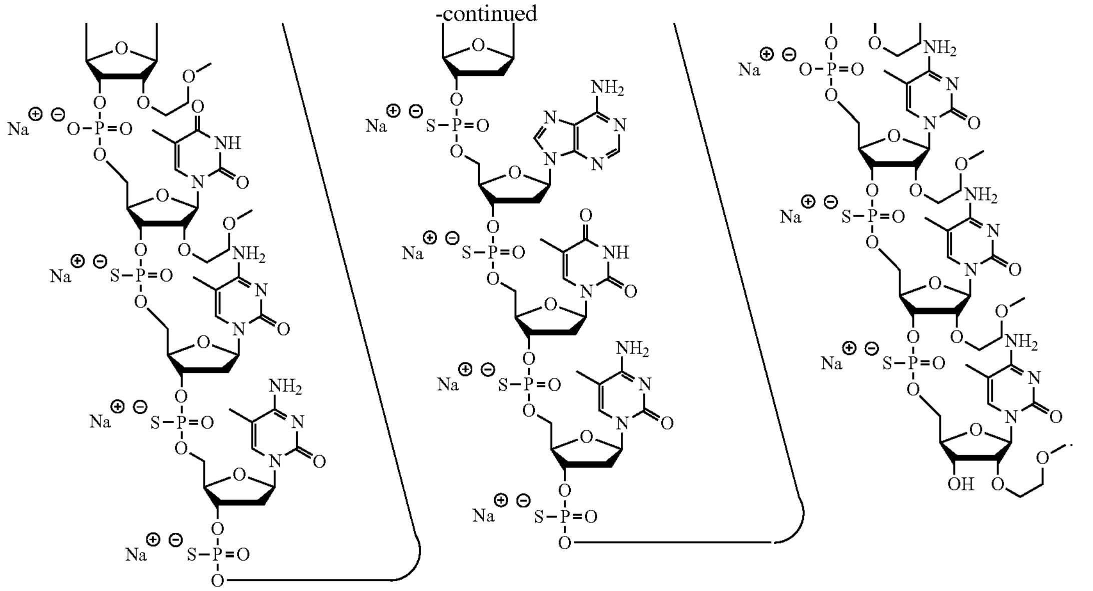
Embodiment 13. A modified oligonucleotide according to the following chemical structure:
(SEQ ID NO 13)
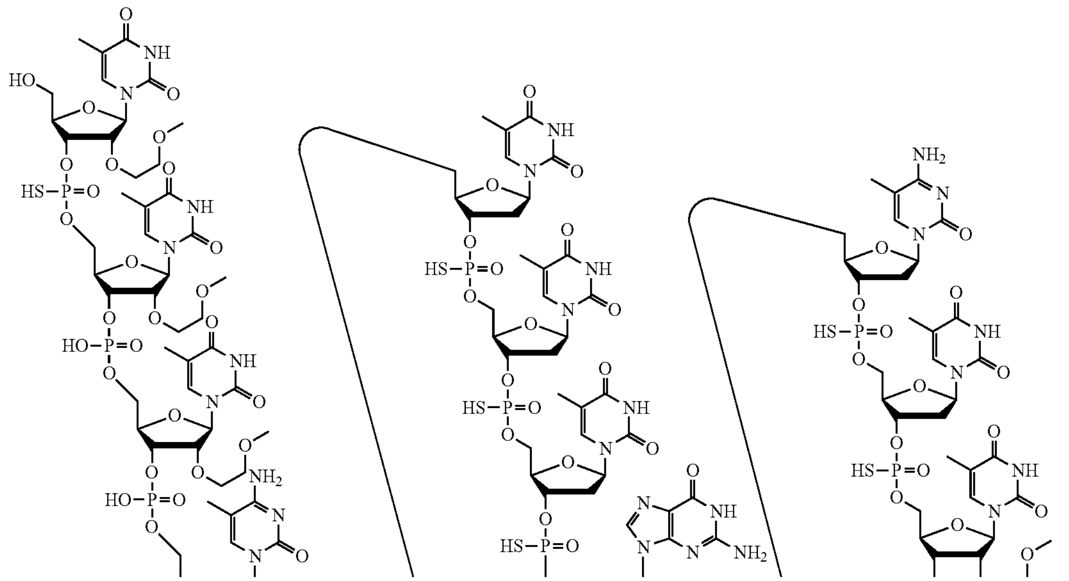

-continued
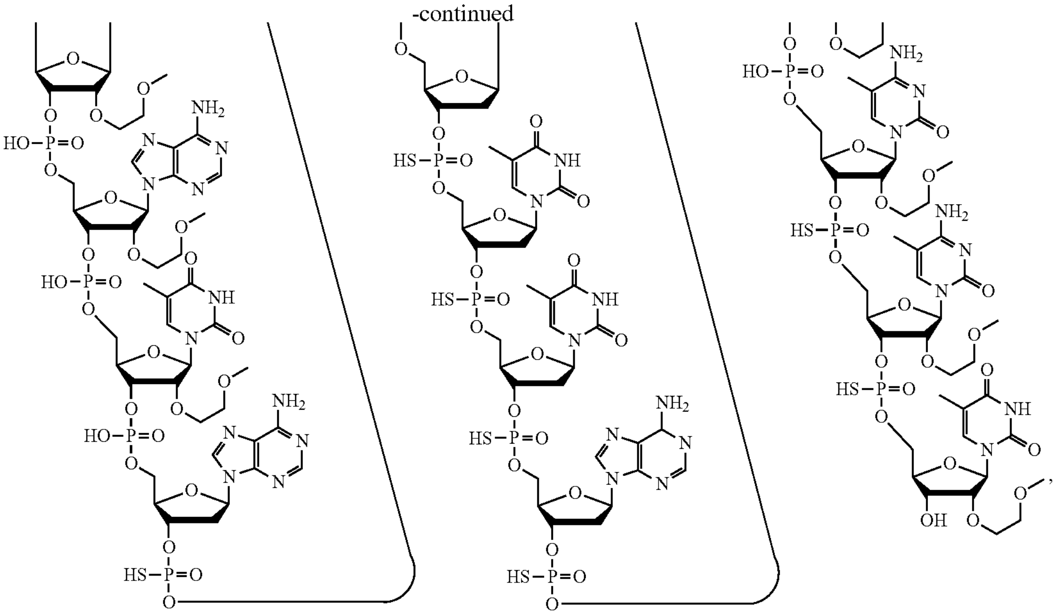
,
or a salt thereof.
Embodiment 14. The modified oligonucleotide of embodiment 13, which is the sodium salt or the potassium salt.
Embodiment 15. A modified oligonucleotide according to the following chemical structure:
(SEQ ID NO 13)
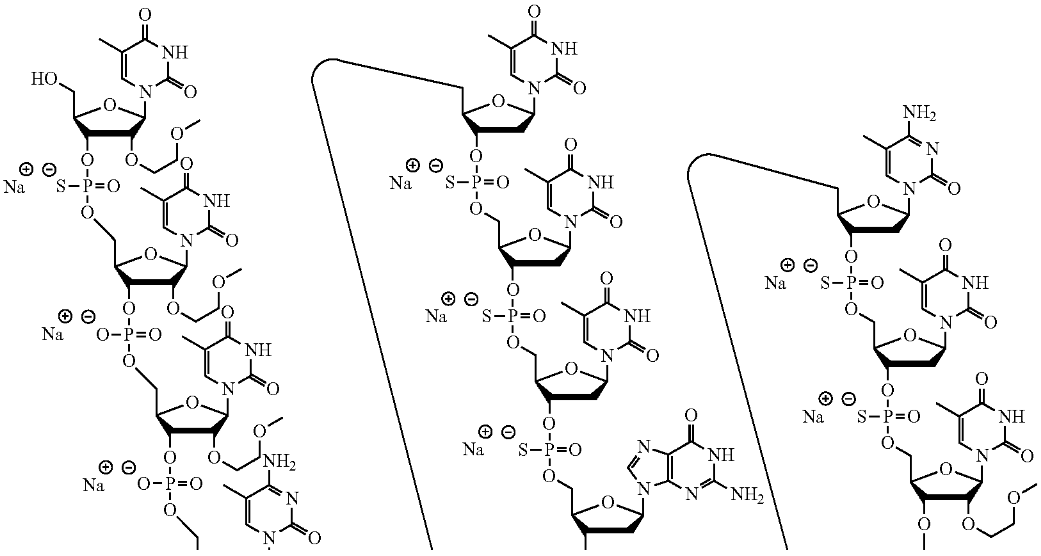

-continued
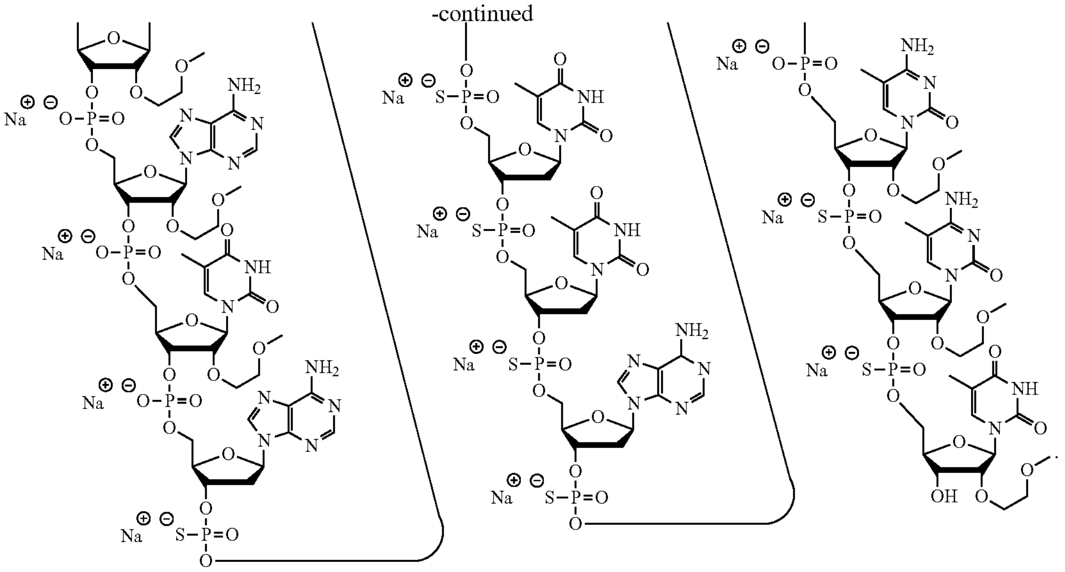
Embodiment 16. A modified oligonucleotide according to the following chemical structure:
(SEQ ID NO 14)
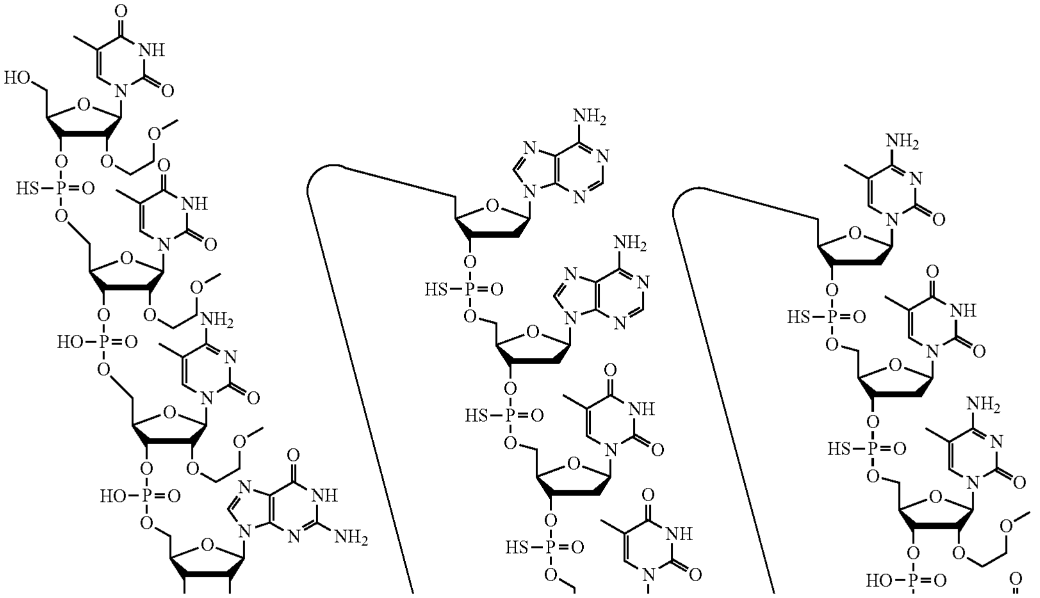

-continued
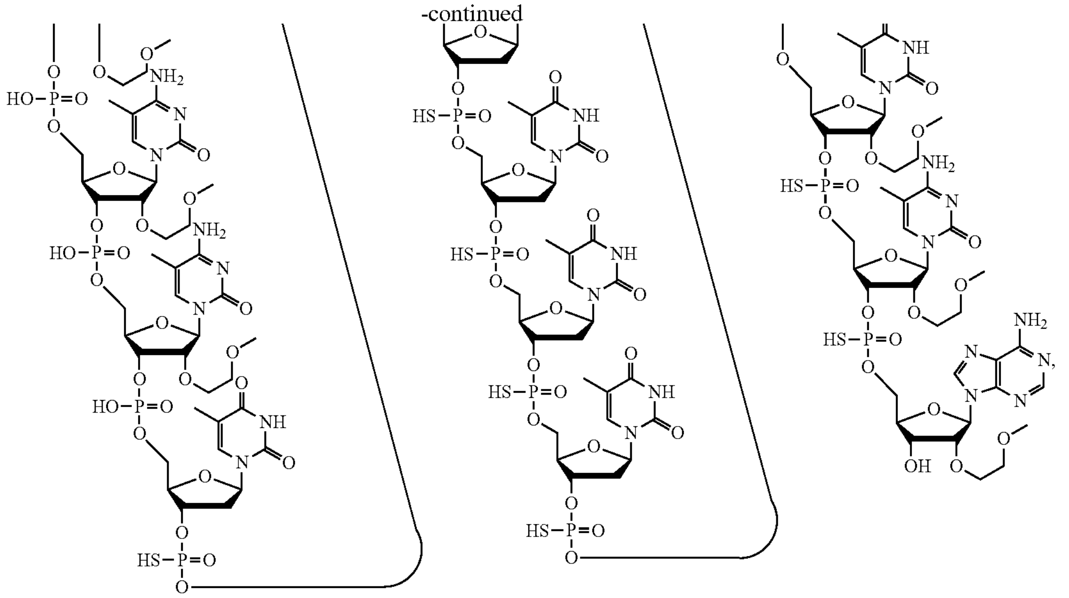
or a salt thereof.
Embodiment 17. The modified oligonucleotide of embodiment 16, which is the sodium salt or the potassium salt.
Embodiment 18. A modified oligonucleotide according to the following chemical structure:
(SEQ ID NO 14)
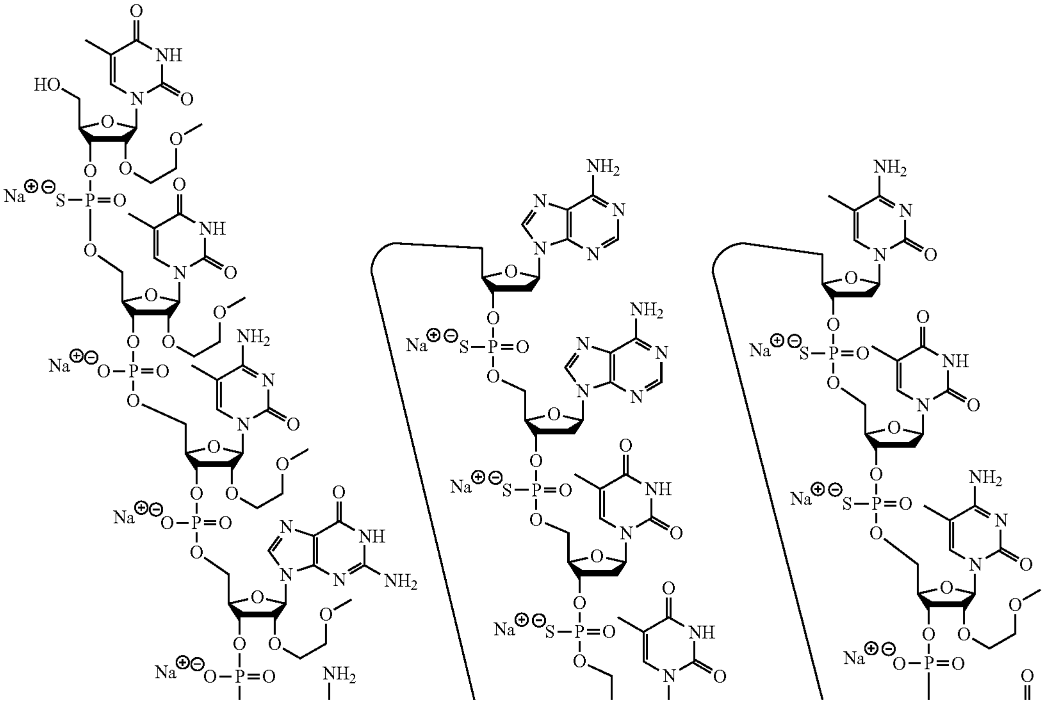

-continued

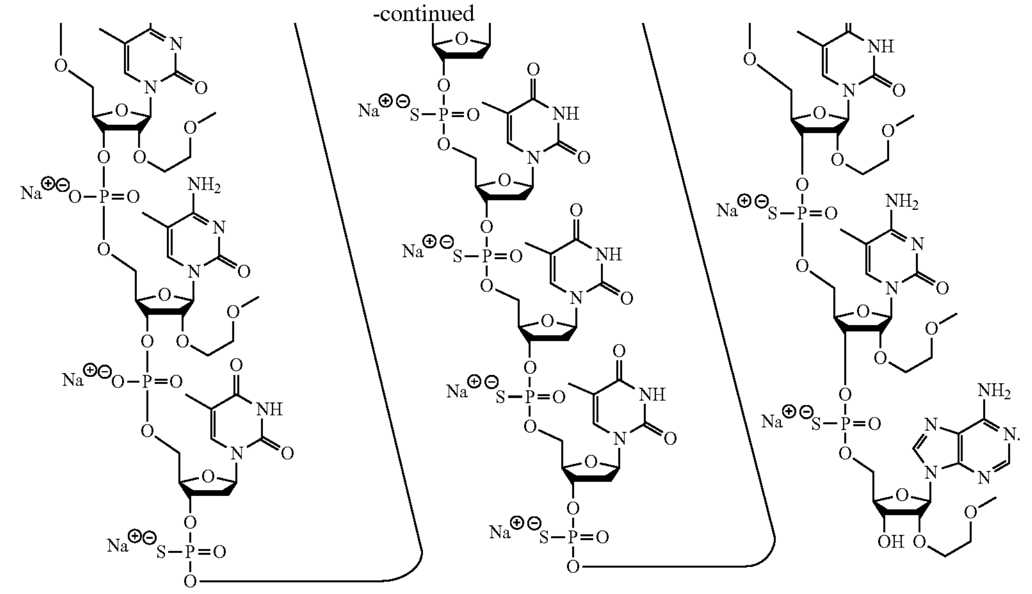

Embodiment 19. An oligomeric compound comprising a modified oligonucleotide according to the following chemical notation: $T_{es}{}^{m}C_{eo}G_{eo}{}^{m}C_{eo}{}^{m}C_{es}T_{ds}A_{ds}A_{ds}T_{ds}T_{ds}T_{ds}T_{ds}T_{ds}{}^{m}C_{ds}T_{ds}{}^{m}C_{eo}T_{eo}{}^{m}C_{es}A_{es}{}^{m}C_{e}$ (SEQ ID NO 10), wherein:

A=an adenine nucleobase, $^{m}$C=a 5-methyl cytosine nucleobase,

G=a guanine nucleobase,

T=a thymine nucleobase, e=a 2'-MOE sugar moiety, d=a 2'-β-D-deoxyribosyl sugar moiety, s=a phosphorothioate internucleoside linkage, and o=a phosphodiester internucleoside linkage.

Embodiment 20. An oligomeric compound comprising a modified oligonucleotide according to the following chemical notation: $^{m}C_{es}T_{eo}T_{eo}T_{eo}T_{eo}{}^{m}C_{ds}T_{ds}G_{ds}{}^{m}C_{ds}T_{ds}{}^{m}C_{ds}T_{ds}T_{ds}A_{ds}T_{ds}A_{eo}{}^{m}C_{es}G_{es}{}^{m}C_{e}$ (SEQ ID NO 11), wherein:

A=an adenine nucleobase, $^{m}$C=a 5-methyl cytosine nucleobase,

G=a guanine nucleobase,

T=a thymine nucleobase, e=a 2'-MOE sugar moiety, d=a 2'-β-D-deoxyribosyl sugar moiety, s=a phosphorothioate internucleoside linkage, and o=a phosphodiester internucleoside linkage.

Embodiment 21. An oligomeric compound comprising a modified oligonucleotide according to the following chemical notation: $^{m}C_{es}T_{eo}G_{eo}T_{eo}T_{eo}T_{ds}A_{ds}{}^{m}C_{ds}A_{ds}T_{ds}T_{ds}T_{ds}T_{ds}T_{ds}T_{ds}T_{eo}T_{es}{}^{m}C_{es}{}^{m}C_{e}$ (SEQ ID NO 12), wherein:

A=an adenine nucleobase, $^{m}$C=a 5-methyl cytosine nucleobase,

G=a guanine nucleobase,

T=a thymine nucleobase, e=a 2'-MOE sugar moiety, d=a 2'-β-D-deoxyribosyl sugar moiety, s=a phosphorothioate internucleoside linkage, and o=a phosphodiester internucleoside linkage.

Embodiment 22. An oligomeric compound comprising a modified oligonucleotide according to the following chemical notation: $T_{es}T_{eo}T_{eo}A_{eo}T_{es}{}^{m}C_{ds}{}^{m}C_{ds}A_{ds}A_{ds}T_{ds}T_{ds}A_{ds}T_{ds}{}^{m}C_{ds}{}^{m}C_{ds}A_{eo}T_{eo}{}^{m}C_{es}{}^{m}C_{es}{}^{m}C_{e}$ (SEQ ID NO 9), wherein:

A=an adenine nucleobase, $^{m}$C=a 5-methyl cytosine nucleobase,

G=a guanine nucleobase,

T=a thymine nucleobase, e=a 2'-MOE sugar moiety, d=a 2'-β-D-deoxyribosyl sugar moiety, s=a phosphorothioate internucleoside linkage, and o=a phosphodiester internucleoside linkage.

Embodiment 23. An oligomeric compound comprising a modified oligonucleotide according to the following chemical notation: $T_{es}T_{eo}T_{eo}{}^{m}C_{eo}A_{eo}T_{eo}A_{ds}T_{ds}T_{ds}T_{ds}G_{ds}T_{ds}T_{ds}A_{ds}{}^{m}C_{ds}T_{ds}T_{eo}{}^{m}C_{es}{}^{m}C_{es}T_{e}$ (SEQ ID NO 13), wherein:

A=an adenine nucleobase, $^{m}$C=a 5-methyl cytosine nucleobase,

G=a guanine nucleobase,

T=a thymine nucleobase, e=a 2'-MOE sugar moiety, d=a 2'-β-D-deoxyribosyl sugar moiety, s=a phosphorothioate internucleoside linkage, and o=a phosphodiester internucleoside linkage.

Embodiment 24. An oligomeric compound comprising a modified oligonucleotide according to the following chemical notation: $T_{es}T_{eo}{}^{m}C_{eo}G_{eo}{}^{m}C_{eo}{}^{m}C_{eo}T_{ds}A_{ds}A_{ds}T_{ds}T_{ds}T_{ds}T_{ds}T_{ds}{}^{m}C_{ds}T_{ds}{}^{m}C_{eo}T_{es}{}^{m}C_{es}A^{e}$ (SEQ ID NO 14), wherein:

A=an adenine nucleobase, $^{m}$C=a 5-methyl cytosine nucleobase,

G=a guanine nucleobase,

T=a thymine nucleobase, e=a 2'-MOE sugar moiety,
d=a 2'-β-D-deoxyribosyl sugar moiety,
s=a phosphorothioate internucleoside linkage, and
o=a phosphodiester internucleoside linkage.

Embodiment 25. A population of modified oligonucleotides of any of embodiments 1-18 or a population of oligomeric compounds of any of embodiments 19-24, wherein all of the phosphorothioate internucleoside linkages of the modified oligonucleotide are stereorandom.

Embodiment 26. A pharmaceutical composition comprising a modified oligonucleotide of any of embodiments 1-18, an oligomeric compound of any of embodiments 19-24, or a population of modified oligonucleotides or population of oligomeric compounds of embodiment 25, and a pharmaceutically acceptable diluent.

Embodiment 27. The pharmaceutical composition of embodiment 26, wherein the pharmaceutically acceptable diluent is artificial cerebrospinal fluid or phosphate-buffered saline.

Embodiment 28. The pharmaceutical composition of embodiment 27, wherein the pharmaceutical composition consists essentially of the modified oligonucleotide, the oligomeric compound, or the population, and artificial cerebrospinal fluid or phosphate-buffered saline.

Embodiment 29. A method comprising administering to a subject a modified oligonucleotide of any of embodiments 1-18, an oligomeric compound of any of embodiments 19-24, a population of modified oligonucleotides or population of oligomeric compounds of embodiment 25, or a pharmaceutical composition of any of embodiments 26-28.

Embodiment 30. A method of treating a disease associated with type I interferon signaling, comprising administering to a subject having a disease associated with type I interferon signaling a therapeutically effective amount of a modified oligonucleotide of any of embodiments 1-18, an oligomeric compound of any of embodiments 19-24, a population of modified oligonucleotides or population of oligomeric compounds of embodiment 25, or a pharmaceutical composition of any of embodiments 26-28; thereby treating the disease associated with type I interferon signaling.

Embodiment 31. The method of embodiment 30, wherein the disease associated with type I interferon signaling is Aicardi-Goutières Syndrome, stroke, Neuropsychiatric Systemic Lupus Erythematosus, neuroinflammation following traumatic brain injury, neuro-autoimmune disorders, Alzheimer's disease, post-operative delirium and cognitive decline, cranial radiation-induced cognitive decline, viral infection-induced cognitive decline, neuromyelitis optica, or ataxia telangiectasia.

Embodiment 32. The method of embodiment 30 or embodiment 31, wherein the disease is associated with an elevated level of interferon-alpha.

Embodiment 33. The method of any of embodiments 30-32, wherein administering the modified oligonucleotide, the oligomeric compound, the population of modified oligonucleotides or population of oligomeric compounds, or the pharmaceutical composition of reduces seizures, dystonia, spasticity, white matter abnormalities, T cell infiltration, B cell infiltration, striatal necrosis, brain atrophy, basal ganglia calcification, or microencephaly in the subject; improves feeding, motor development, language development, or social skill development in the subject; or reduces interferon alpha or lymphocytosis in the cerebrospinal fluid of the subject.

Embodiment 34. A method of reducing expression of IFNAR1 in a cell, comprising contacting the cell with a modified oligonucleotide of any of embodiments 1-18, an oligomeric compound of any of embodiments 19-24, a population of modified oligonucleotides or population of oligomeric compounds of embodiment 25, or a pharmaceutical composition of any of embodiments 26-28.

Embodiment 35. The method of embodiment 34, wherein the cell is a neuron or a glial cell, optionally wherein the cell is an astrocyte or microglial cell.

Embodiment 36. The method of any of embodiments 29-33, wherein the subject is human.

Embodiment 37. The method of embodiment 34 or embodiment 35, wherein the cell is a human cell.

Embodiment 38. Use of a modified oligonucleotide of any of embodiments 1-18, an oligomeric compound of any of embodiments 19-24, a population of modified oligonucleotides or population of oligomeric compounds of embodiment 25, or a pharmaceutical composition of any of embodiments 26-28 for treating a disease associated with type I interferon signaling.

Embodiment 39. Use of a modified oligonucleotide of any of embodiments 1-18, an oligomeric compound of any of embodiments 19-24, a population of modified oligonucleotides or population of oligomeric compounds of embodiment 25, or a pharmaceutical composition of any of embodiments 26-28 in the manufacture of a medicament for treating a disease associated with type I interferon signaling.

Embodiment 40. The use of embodiment 38 or embodiment 39, wherein the disease is associated with an elevated level of interferon alpha.

Embodiment 41. The use of any of embodiments 38-40, wherein the disease associated with type I interferon signaling is Aicardi-Goutières Syndrome, stroke, neuropsychiatric systemic lupus erythematosus, neuroinflammation following traumatic brain injury, neuro-autoimmune disorders, Alzheimer's disease, post-operative delirium and cognitive decline, cranial radiation-induced cognitive decline, viral infection-induced cognitive decline, neuromyelitis optica, or ataxia telangiectasia.

1. Compound No. 1489477

In certain embodiments, Compound No. 1489477 is characterized as a 6-10-4 MOE gapmer having a sequence (from 5' to 3') of CTTTTTCTGCTCTTATACGC (SEQ ID NO 11), wherein each of nucleosides 1-6 and 17-20 (from 5' to 3') are 2'-MOE nucleosides and each of nucleosides 7-16 are 2'-β-D-deoxynucleosides, wherein the internucleoside linkages between nucleosides 2 to 3, 3 to 4, 4 to 5, 5 to 6, 6 to 7, and 17 to 18 are phosphodiester internucleoside linkages, the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

In certain embodiments, Compound No. 1489477 is represented by the following chemical notation: $^{m}C_{es}T_{eo}T_{eo}T_{eo}T_{eo}T_{eo}{^{m}}C_{ds}T_{ds}G_{ds}{^{m}}C_{ds}T_{ds}{^{m}}C_{ds}T_{ds}T_{ds}A_{ds}T_{ds}A_{eo}{^{m}}C_{es}G_{es}{^{m}}C_{e}$ (SEQ ID NO 11), wherein:
A=an adenine nucleobase,
$^{m}$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

In certain embodiments Compound No. 1489477 is represented by the following chemical structure:
Structure 1. Compound No. 1489477
(SEQ ID NO 11)
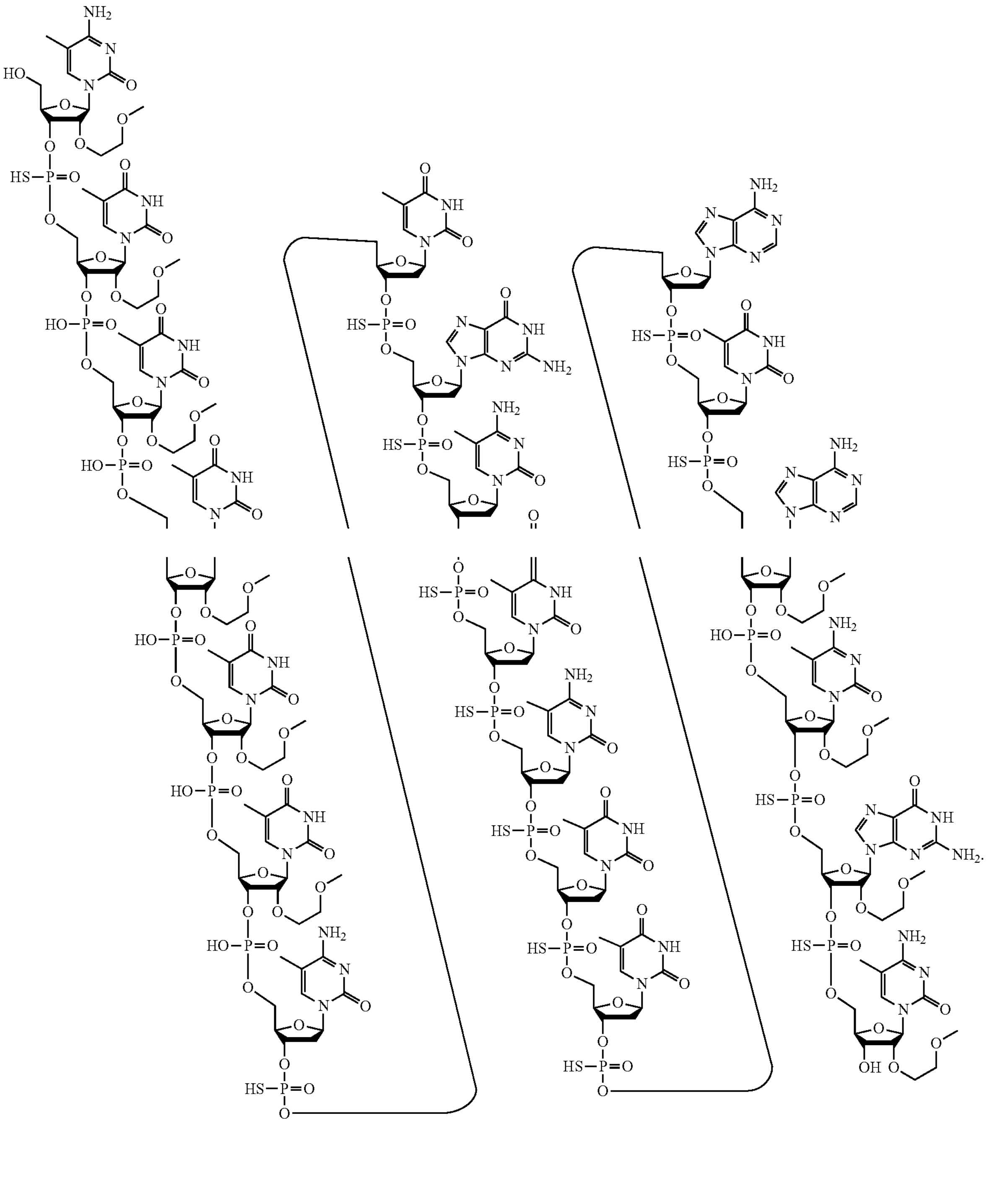
In certain embodiments, an oligomeric compound comprises the sodium salt or the potassium salt of the modified oligonucleotide represented by Structure 1.

In certain embodiments the sodium salt of Compound No. 1489477 is represented by the following chemical structure:

Structure 2. The sodium salt of Compound No. 1489477

(SEQ ID NO 11)

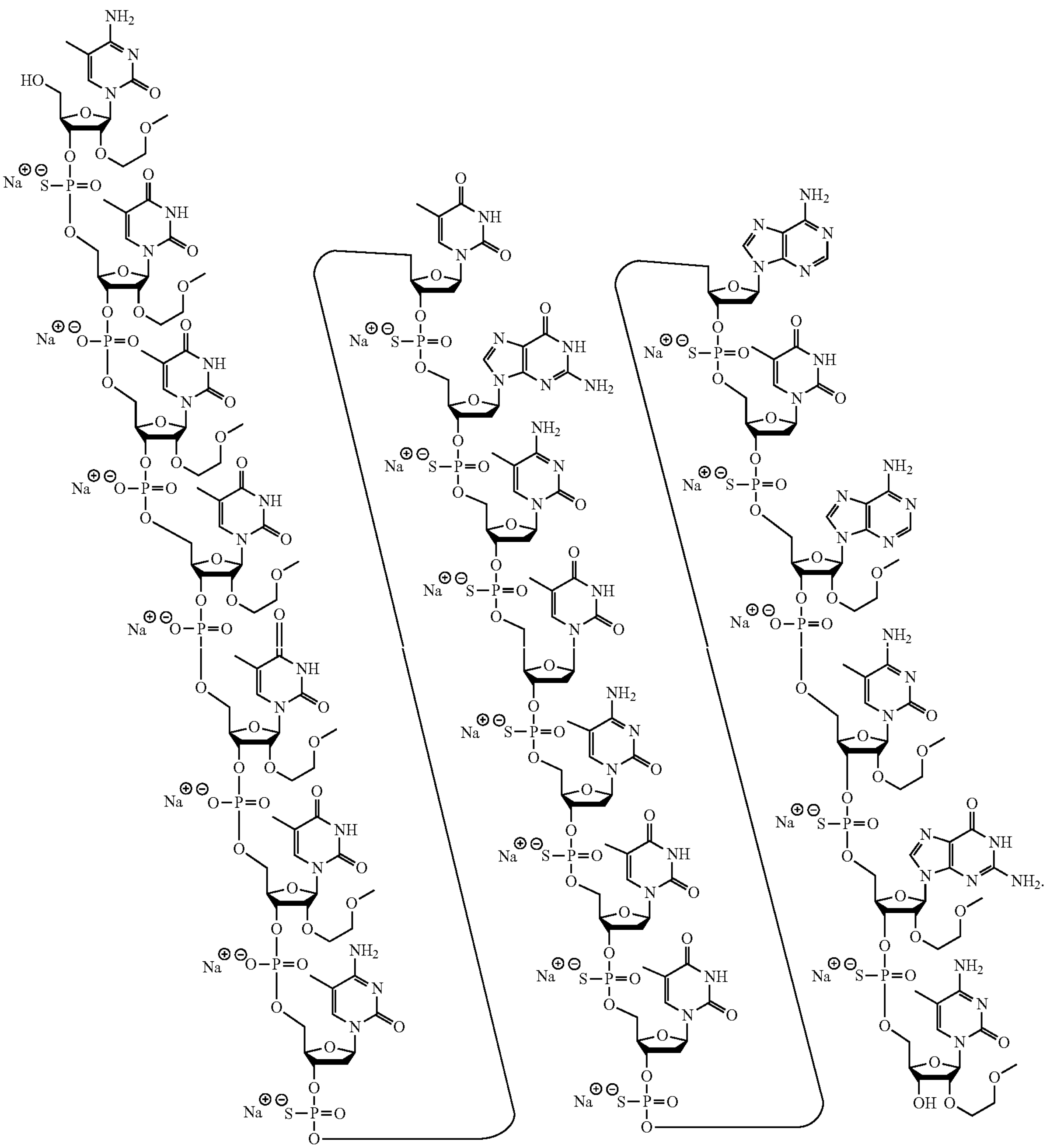

2. Compound No. 1489494

In certain embodiments, Compound No. 1489494 is characterized as a 6-10-4 MOE gapmer having a sequence (from 5' to 3') of CTGTTTTACATTTTTTTTCC (SEQ ID NO 12), wherein each of nucleosides 1-6 and 17-20 (from 5' to 3') are 2'-MOE nucleosides and each of nucleosides 7-16 are 2'-β-D-deoxynucleosides, wherein the internucleoside linkages between nucleosides 2 to 3, 3 to 4, 4 to 5, 5 to 6, 6 to 7, and 17 to 18 are phosphodiester internucleoside linkages, the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

In certain embodiments, Compound No. 1489494 is represented by the following chemical notation: $^{m}C_{es}T_{eo}G_{eo}T_{eo}T_{eo}T_{eo}T_{ds}A_{ds}{}^{m}C_{ds}A_{ds}T_{ds}T_{ds}T_{ds}T_{ds}T_{ds}T_{ds}T_{eo}T_{es}{}^{m}C_{es}{}^{m}C_{e}$ (SEQ ID NO 12), wherein:

A=an adenine nucleobase,
$^{m}$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

In certain embodiments Compound No. 1489494 is represented by the following chemical structure:

Structure 3. Compound No. 1489494

(SEQ ID NO 12)

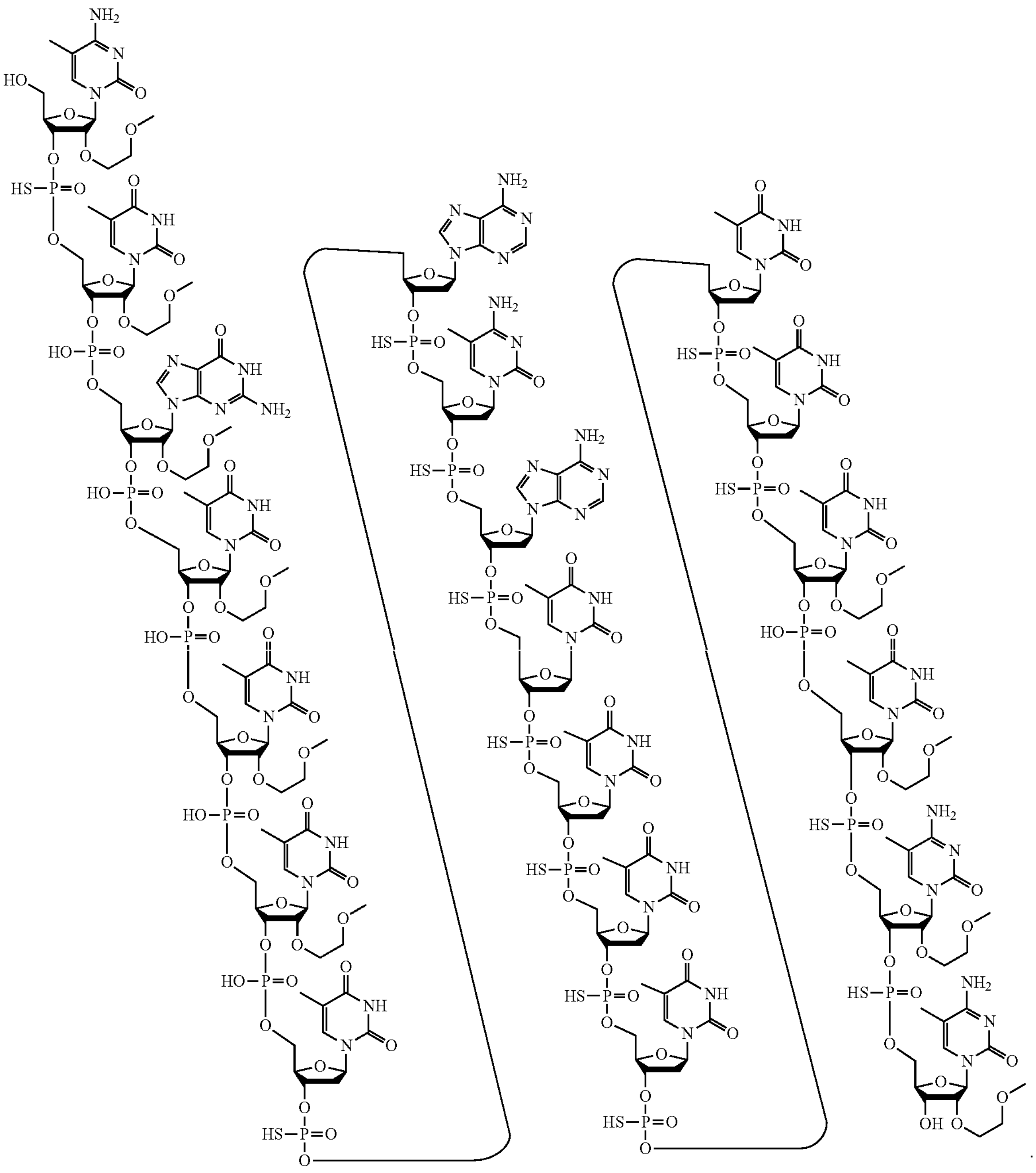

In certain embodiments, an oligomeric compound comprises the sodium salt or the potassium salt of the modified oligonucleotide represented by Structure 3.

In certain embodiments the sodium salt of Compound No. 1489494 is represented by the following chemical structure:

Structure 2. The sodium salt of Compound No. 1489494

(SEQ ID NO 12)

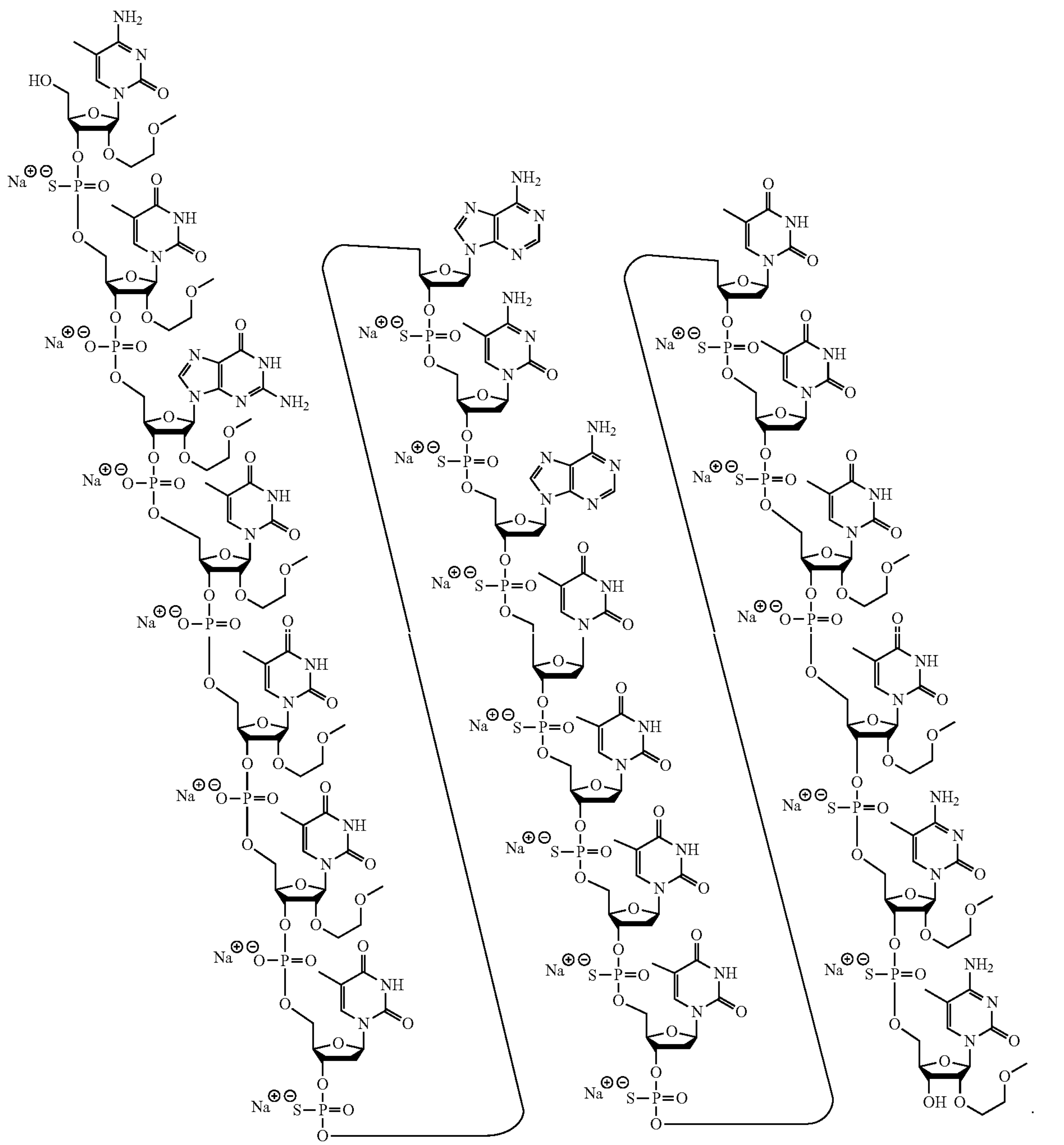

3. Compound No. 1489525

In certain embodiments, Compound No. 1489525 is characterized as a 5-10-5 MOE gapmer having a sequence (from 5' to 3') of TTTATCCAATTATCCATCCC (SEQ ID NO 9), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 16 to 17, and 17 to 18 are phosphodiester internucleoside linkages, the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1489525 is represented by the following chemical notation: $T_{es}T_{eo}T_{eo}A_{eo}T_{es}{}^{m}C_{ds}{}^{m}C_{ds}A_{ds}A_{ds}T_{ds}T_{ds}A_{ds}T_{ds}{}^{m}C_{ds}{}^{m}C_{ds}A_{eo}$-$T_{eo}{}^{m}C_{es}{}^{m}C_{es}{}^{m}C_{e}$ (SEQ ID NO 9), wherein:

A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

In certain embodiments Compound No. 1489525 is represented by the following chemical structure:

Structure 5. Compound No. 1489525

(SEQ ID NO 9)

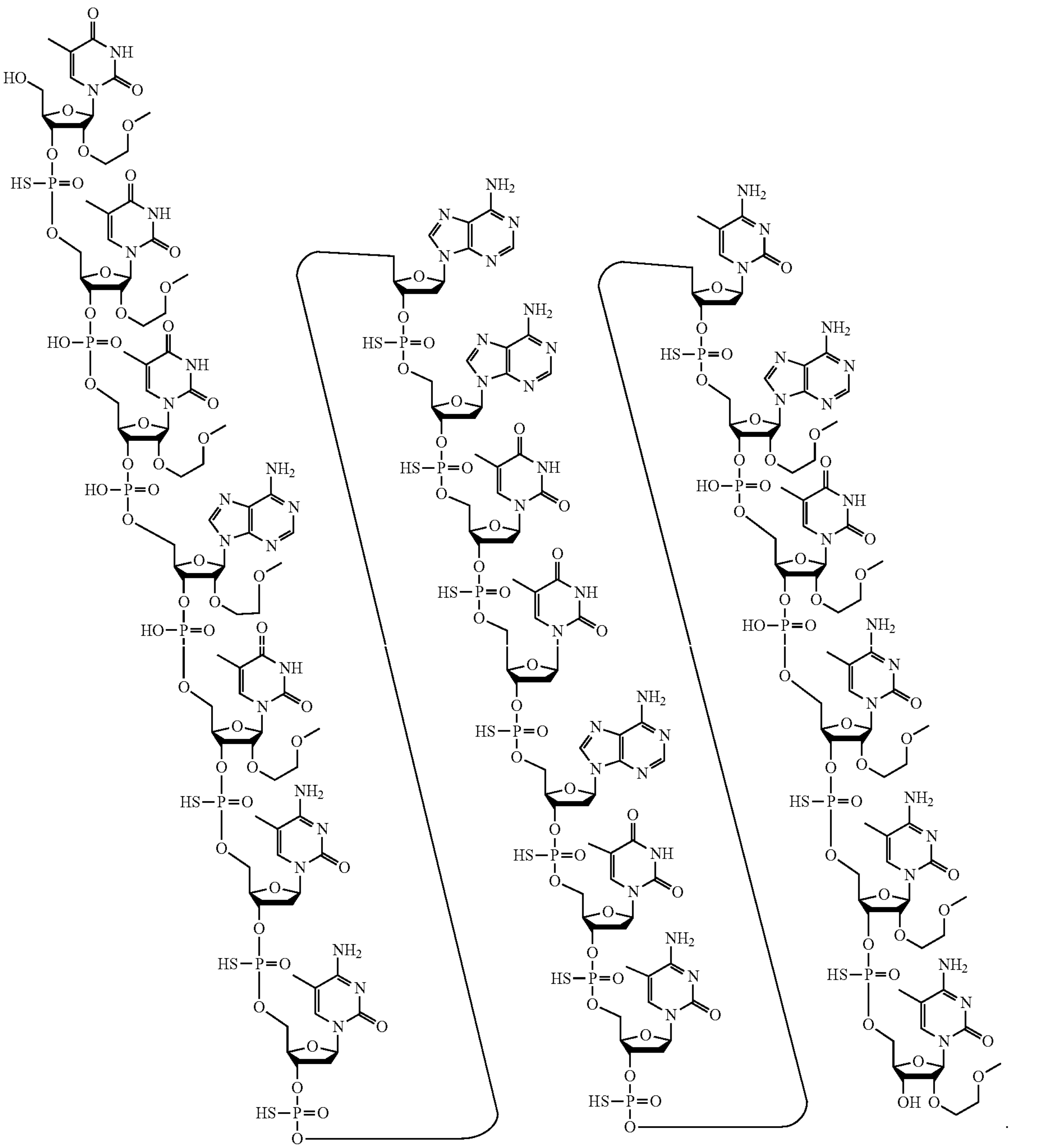

In certain embodiments, an oligomeric compound comprises the sodium salt or the potassium salt of the modified oligonucleotide represented by Structure 5.

In certain embodiments the sodium salt of Compound No. 1489525 is represented by the following chemical structure:

Structure 6. The sodium salt of Compound No. 1489525

(SEQ ID NO 9)

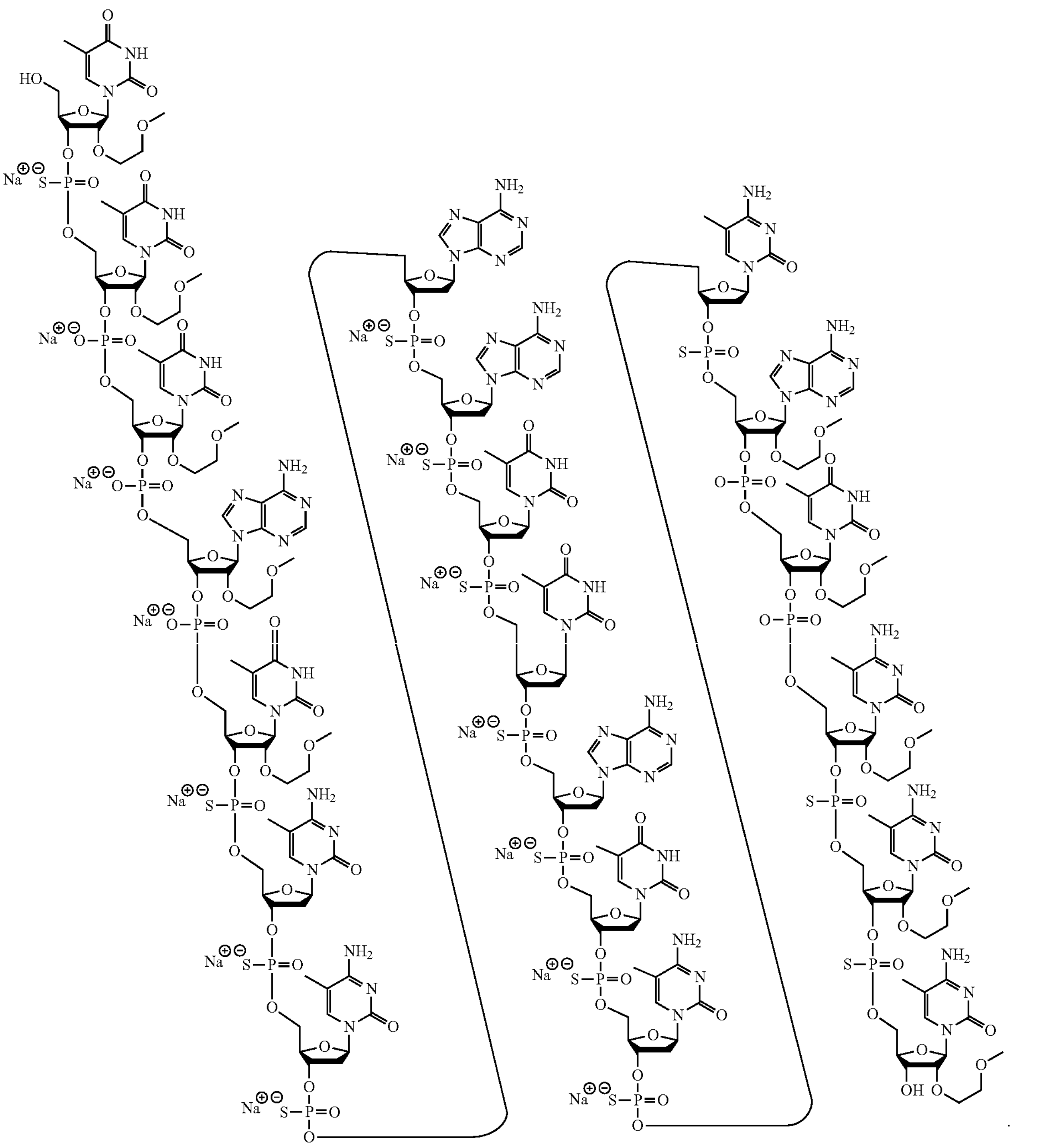

4. Compound No. 1492069

In certain embodiments, Compound No. 1492069 is characterized as a 5-10-5 MOE gapmer having a sequence (from 5' to 3') of TCGCCTAATTTTTCTCTCAC (SEQ ID NO 10), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 16 to 17, and 17 to 18 are phosphodiester internucleoside linkages, the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1492069 is represented by the following chemical notation: $T_{es}{}^{m}C_{eo}G_{eo}{}^{m}C_{eo}{}^{m}C_{es}T_{ds}A_{ds}A_{ds}T_{ds}T_{ds}T_{ds}T_{ds}T_{ds}{}^{m}C_{ds}T_{ds}{}^{m}$-$C_{eo}T_{eo}{}^{m}C_{es}A_{es}{}^{m}C_{e}$ (SEQ ID NO 10), wherein:

A=an adenine nucleobase,
$^{m}C$=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

In certain embodiments Compound No. 1492069 is represented by the following chemical structure:

Structure 7. Compound No. 1492069

(SEQ ID NO 10)

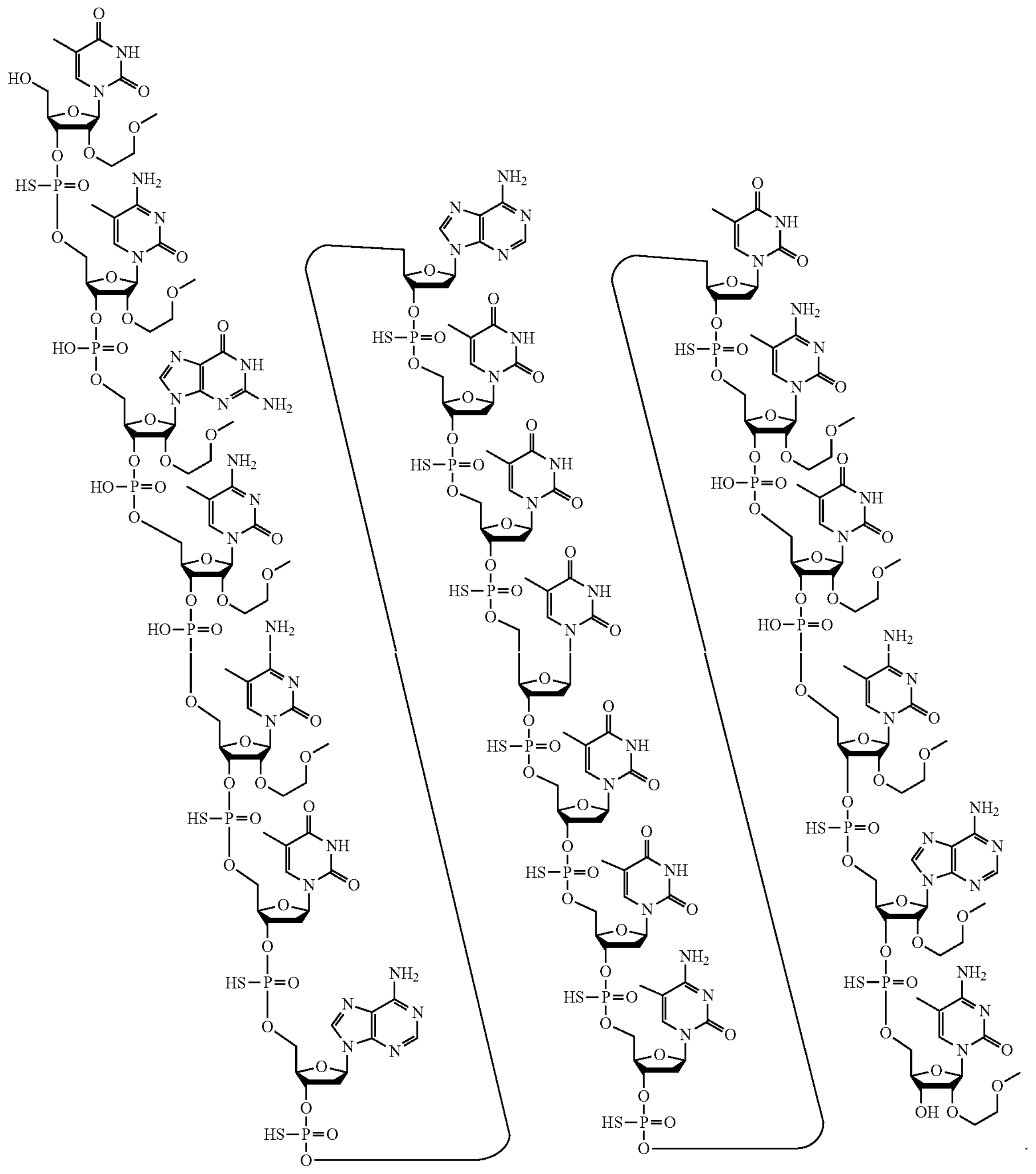

In certain embodiments, an oligomeric compound comprises the sodium salt or the potassium salt of the modified oligonucleotide represented by Structure 7.

In certain embodiments the sodium salt of Compound No. 1492069 is represented by the following chemical structure:

Structure 8. The sodium salt of Compound No. 1492069

(SEQ ID NO 10)

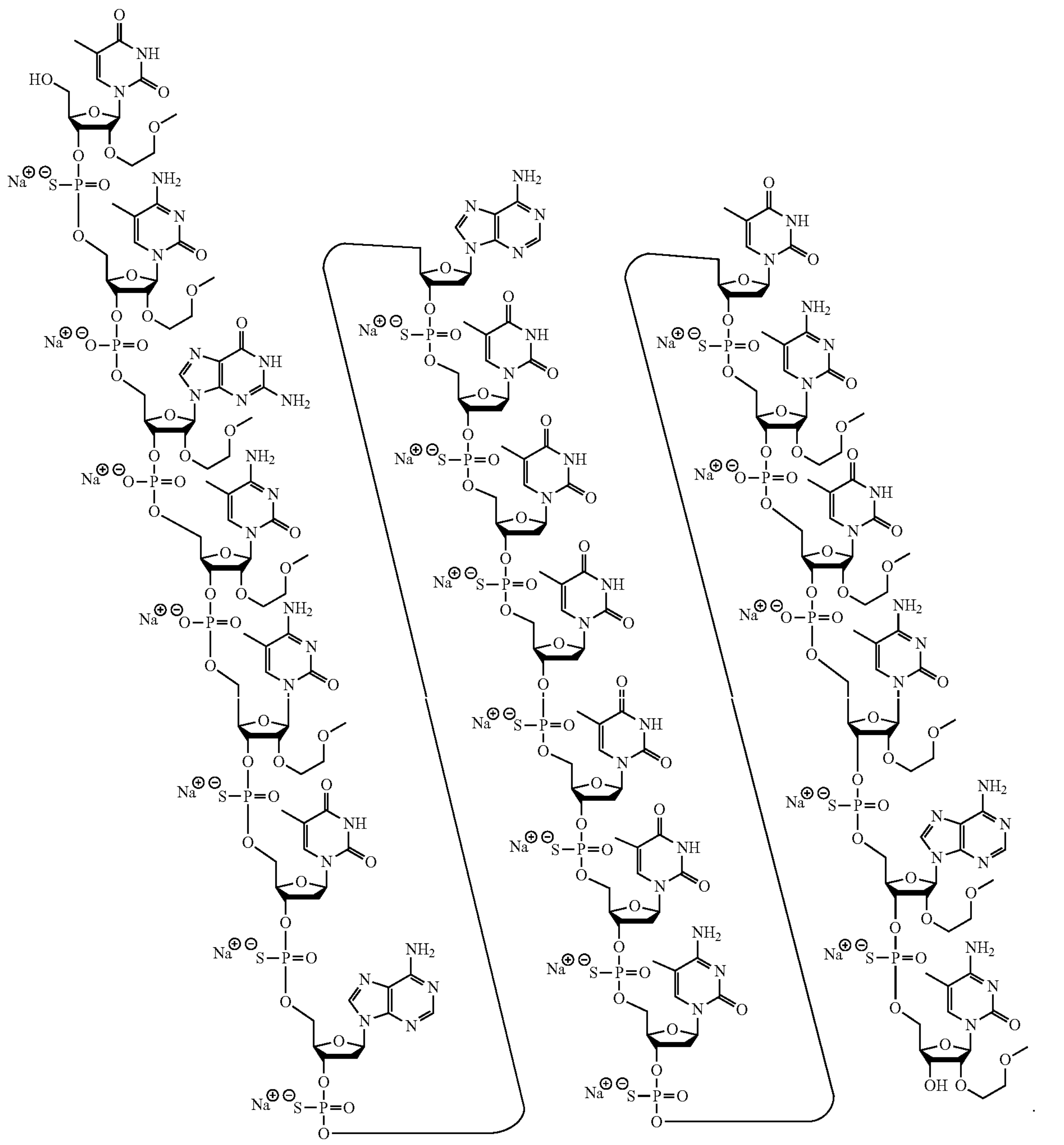

5. Compound No. 1492082

In certain embodiments, Compound No. 1492082 is characterized as a 6-10-4 MOE gapmer having a sequence (from 5' to 3') of TTTCATATTTGTTACTTCCT (SEQ ID NO 13), wherein each of nucleosides 1-6 and 17-20 (from 5' to 3') are 2'-MOE nucleosides and each of nucleosides 7-16 are 2'-β-D-deoxynucleosides, wherein the internucleoside linkages between nucleosides 2 to 3, 3 to 4, 4 to 5, 5 to 6, 6 to 7, and 17 to 18 are phosphodiester internucleoside linkages, the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

In certain embodiments, Compound No. 1492082 is represented by the following chemical notation: $T_{es}T_{eo}T_{eo}{}^{m}C_{eo}A_{eo}T_{eo}A_{ds}T_{ds}T_{ds}T_{ds}G_{ds}T_{ds}T_{ds}A_{ds}{}^{m}C_{ds}T_{ds}T_{eo}{}^{m}C_{es}{}^{m}C_{es}T_{e}$ (SEQ ID NO 13), wherein:

A=an adenine nucleobase,
$^{m}$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

In certain embodiments Compound No. 1492082 is represented by the following chemical structure:

Structure 9. Compound No. 1492082

(SEQ ID NO 13)

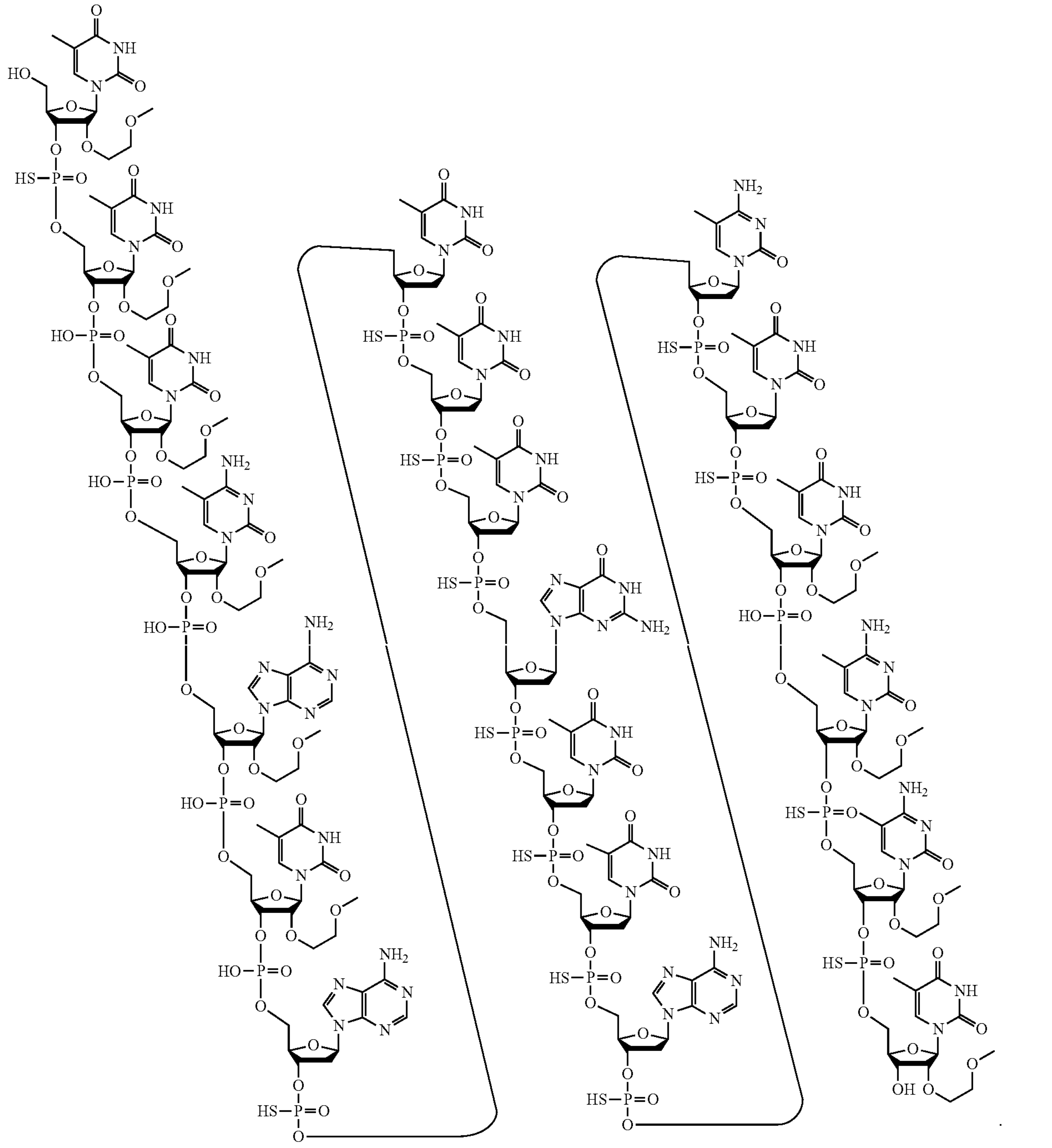

In certain embodiments, an oligomeric compound comprises the sodium salt or the potassium salt of the modified oligonucleotide represented by Structure 9.

In certain embodiments the sodium salt of Compound No. 1492082 is represented by the following chemical structure:

Structure 10. The sodium salt of Compound No. 1492082

(SEQ ID NO 13)

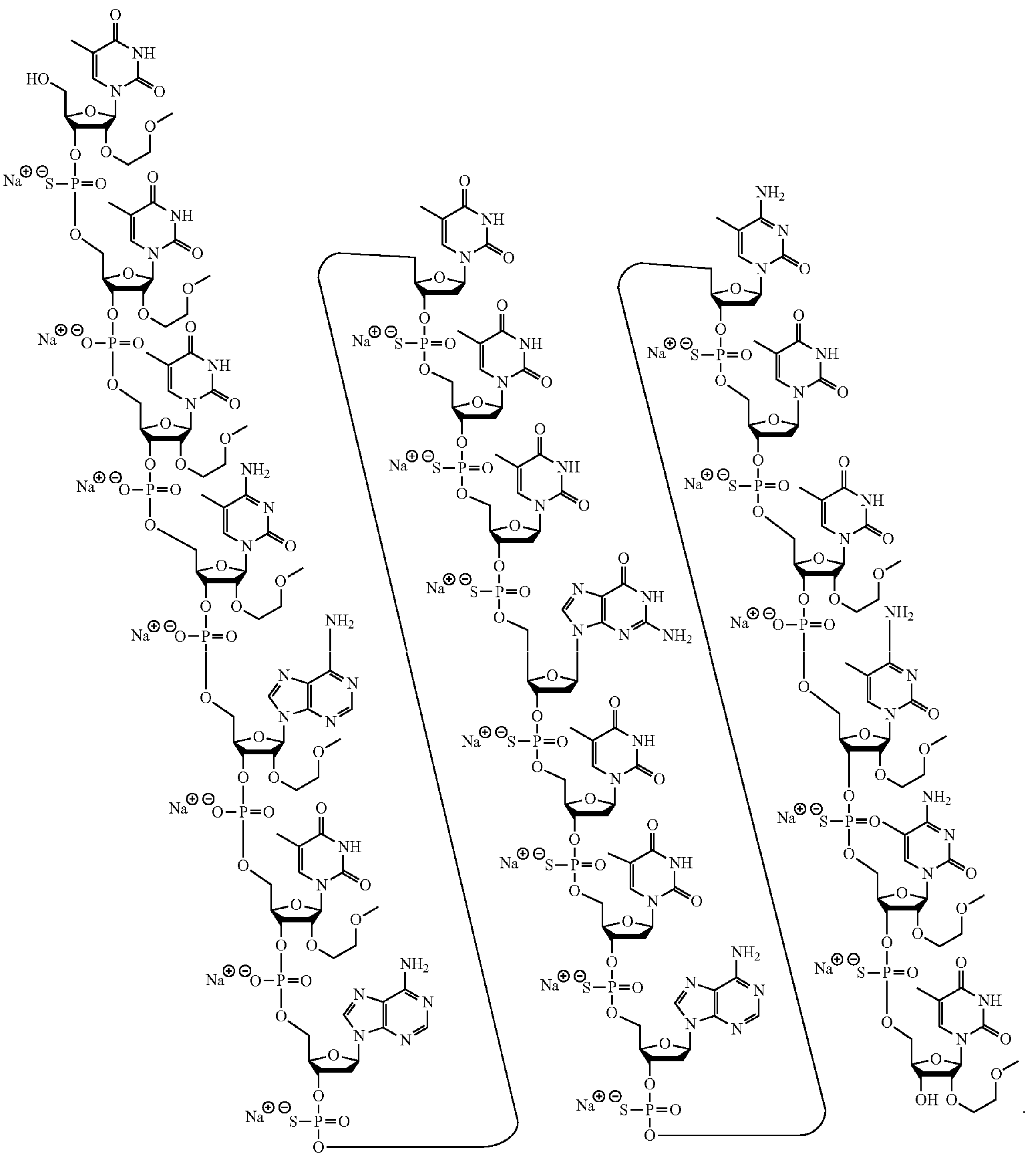

6. Compound No. 1492131

In certain embodiments, Compound No. 1492131 is characterized as a 6-10-4 MOE gapmer having a sequence (from 5' to 3') of TTCGCCTAATTTTTCTCTCA (SEQ ID NO 14), wherein each of nucleosides 1-6 and 17-20 (from 5' to 3') are 2'-MOE nucleosides and each of nucleosides 7-16 are 2'-β-D-deoxynucleosides, wherein the internucleoside linkages between nucleosides 2 to 3, 3 to 4, 4 to 5, 5 to 6, 6 to 7, and 17 to 18 are phosphodiester internucleoside linkages, the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

In certain embodiments, Compound No. 1492131 is represented by the following chemical notation: $T_{es}T_{eo}{}^{m}C_{eo}G_{eo}{}^{m}C_{eo}{}^{m}C_{eo}T_{ds}A_{ds}A_{ds}T_{ds}T_{ds}T_{ds}T_{ds}T_{ds}{}^{m}C_{ds}T_{ds}{}^{m}C_{eo}T_{es}{}^{m}C_{es}A_{e}$ (SEQ ID NO 14), wherein:

A=an adenine nucleobase,
$^m$C=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

In certain embodiments Compound No. 1492131 is represented by the following chemical structure:

Structure 11. Compound No. 1492131

(SEQ ID NO 14)

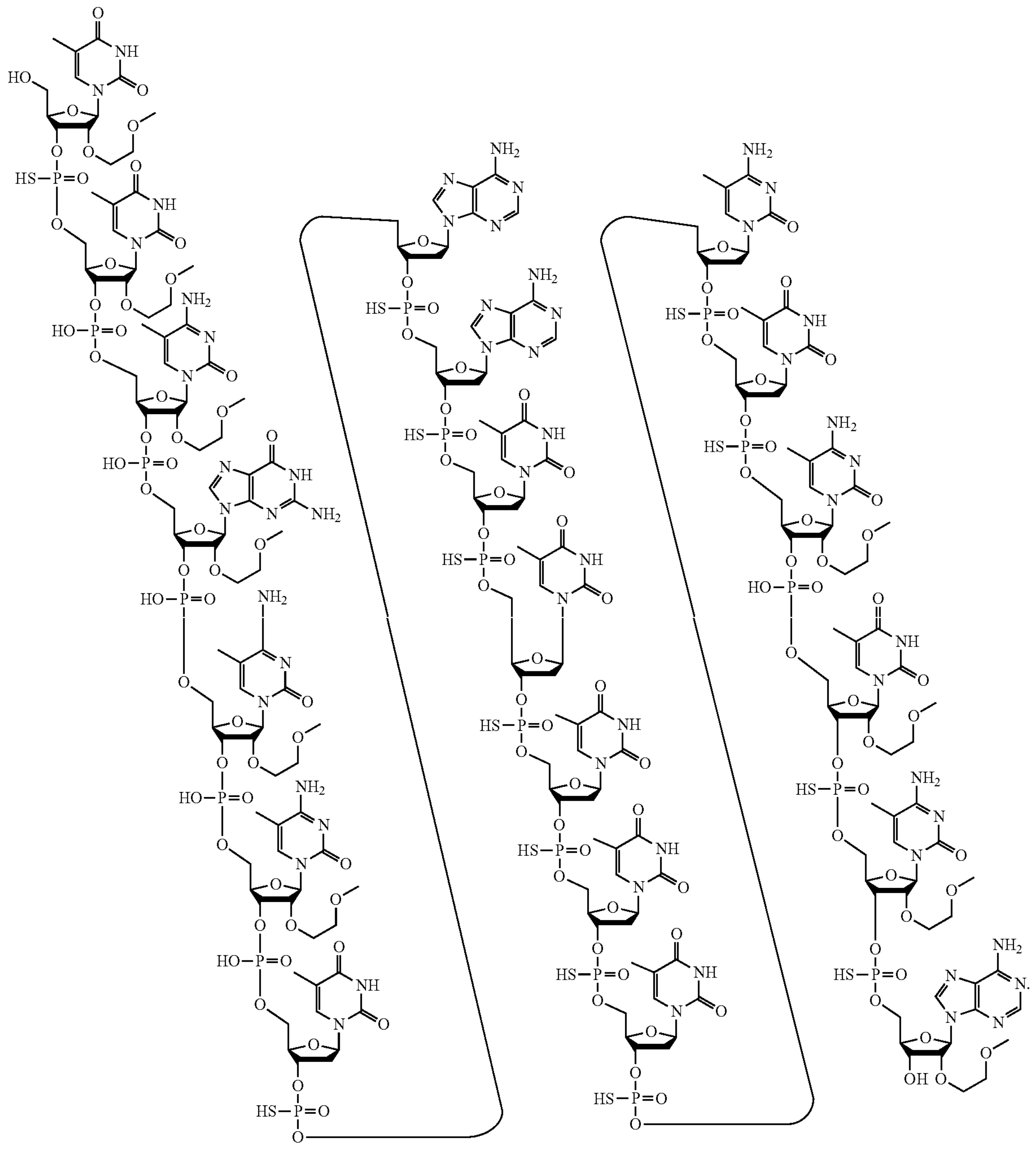

In certain embodiments, an oligomeric compound comprises the sodium salt or the potassium salt of the modified oligonucleotide represented by Structure 11.

In certain embodiments the sodium salt of Compound No. 1492131 is represented by the following chemical structure:

Structure 12. The sodium salt of Compound No. 1492131.

(SEQ ID NO 14)

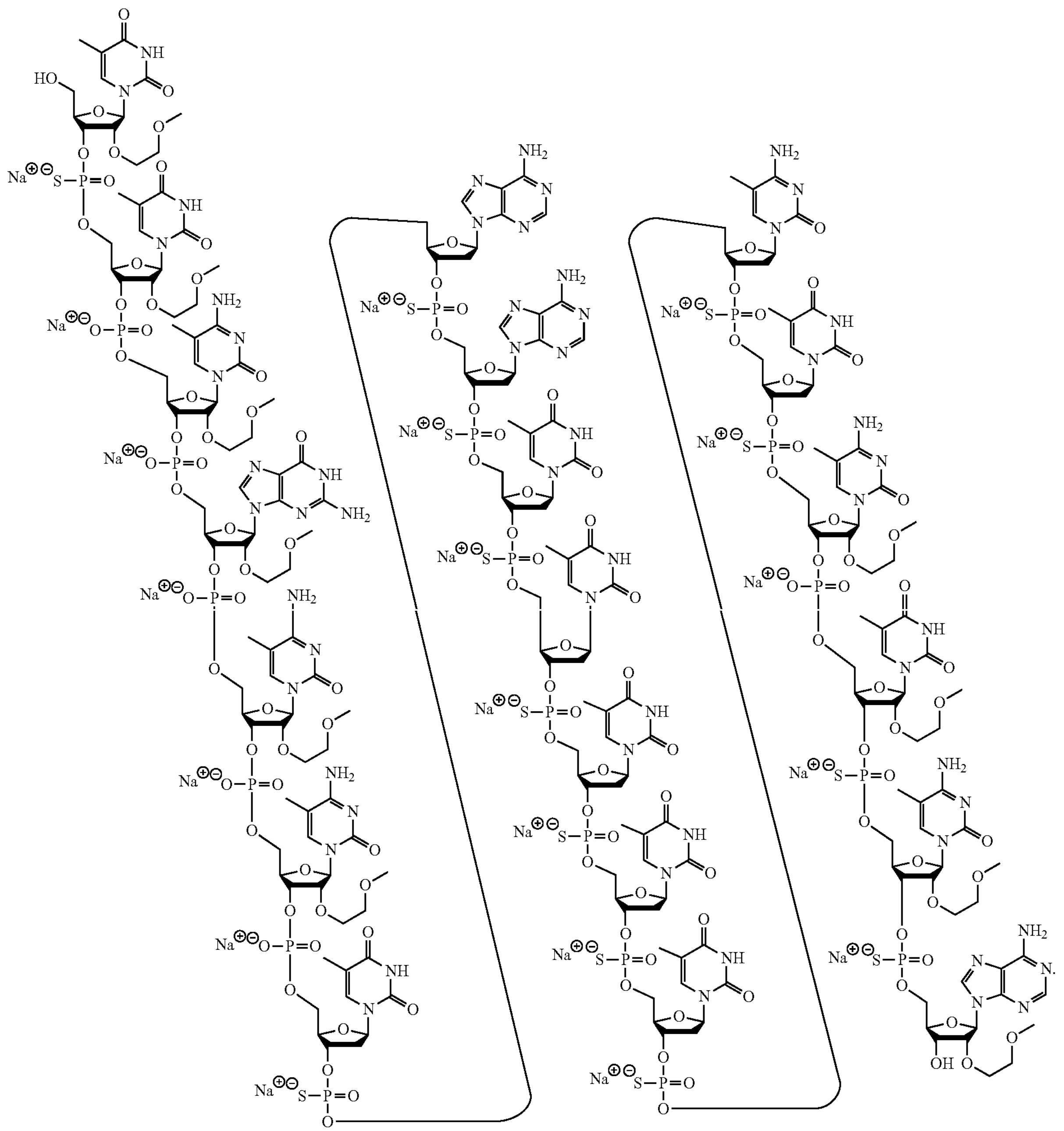

I. Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 3', 4', and/or 5' positions. Examples of 2'-substituent groups suitable for non-bicyclic modified sugar moieties include but are not limited to 2'-O($CH_2$)$_2$ $OCH_3$ ("MOE" or "O-methoxyethyl").

In certain embodiments, modified furanosyl sugar moieties and nucleosides incorporating such modified furanosyl sugar moieties are further defined by isomeric configuration. For example, a 2'-deoxyfuranosyl sugar moiety may be in seven isomeric configurations other than the naturally occurring β-D-deoxyribosyl configuration. Such modified sugar moieties are described in, e.g., WO 2019/157531, incorporated by reference herein. A 2'-modified sugar moiety has an additional stereocenter at the 2'-position relative to a 2'-deoxyfuranosyl sugar moiety; therefore, such sugar moieties have a total of sixteen possible isomeric configurations. 2'-modified sugar moieties described herein are in the β-D-ribosyl isomeric configuration unless otherwise specified.

2. Certain Modified Nucleobases

In certain embodiments, modified oligonucleotides comprise one or more nucleosides comprising an unmodified nucleobase. In certain embodiments, modified oligonucleotides comprise one or more nucleosides comprising a modified nucleobase. Examples of modified nucleobases include 5-methylcytosine.

Publications that teach the preparation of certain modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

3. Certain Modified Internucleoside Linkages

The naturally occurring internucleoside linkage of RNA and DNA is a 3' to 5' phosphodiester linkage. In certain embodiments, nucleosides of modified oligonucleotides may be linked together using one or more modified internucleoside linkages. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate or other linkages containing chiral centers in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

($R_p$)

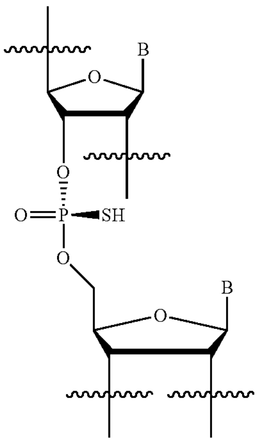

-continued ($S_p$)

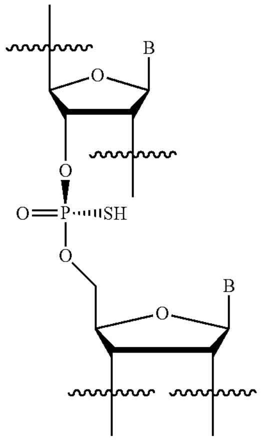

Unless otherwise indicated, chiral internucleoside linkages of modified oligonucleotides described herein can be stereorandom or in a particular stereochemical configuration.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

Gapmer Oligonucleotides

In certain embodiments, modified oligonucleotides comprise or consist of a region having a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-6 nucleosides. In certain embodiments, each nucleoside of each wing of a gapmer comprises a modified sugar moiety. In certain embodiments, at least one nucleoside of each wing of a gapmer comprises a modified sugar moiety. In certain embodiments, at least two nucleosides of each wing of a gapmer comprises a modified sugar moiety. In certain embodiments, at least three nucleosides of each wing of a gapmer comprises a modified sugar moiety. In certain embodiments, at least four nucleosides of each wing of a gapmer comprises a modified sugar moiety.

In certain embodiments, the gap of a gapmer comprises 7-12 nucleosides. In certain embodiments, each nucleoside of the gap of a gapmer comprises a 2'-β-D-deoxyribosyl sugar moiety. In certain embodiments, at least one nucleoside of the gap of a gapmer comprises a modified sugar moiety.

In certain embodiments, the gapmer is a deoxy gapmer. In certain embodiments, the nucleosides on the gap side of each wing/gap junction comprise 2'-deoxyribosyl sugar moieties and the nucleosides on the wing sides of each wing/gap junction comprise modified sugar moieties. In certain embodiments, each nucleoside of the gap comprises a 2'-β-D-deoxyribosyl sugar moiety. In certain embodiments, each nucleoside of each wing of a gapmer comprises a modified sugar moiety. In certain embodiments, at least one nucleoside of the gap of a gapmer comprises a modified sugar moiety. In certain embodiments, one nucleoside of the gap comprises a modified sugar moiety and each remaining nucleoside of the gap comprises a 2'-deoxyribosyl sugar moiety. In certain embodiments, at least one nucleoside of the gap of a gapmer comprises a 2'-OMe sugar moiety.

Herein, the lengths (number of nucleosides) of the three regions of a gapmer may be provided using the notation [#of nucleosides in the 5'-wing]-[#of nucleosides in the gap]-[#of nucleosides in the 3'-wing]. Thus, a 3-10-3 gapmer consists of 3 linked nucleosides in each wing and 10 linked nucleosides in the gap. Where such nomenclature is followed by a specific modification, that modification is the modification in each sugar moiety of each wing and the gap nucleosides comprise 2'-β-D-deoxyribosyl sugar moieties. Thus, a 5-10-5 MOE gapmer consists of 5 linked 2'-MOE nucleosides in the 5'-wing, 10 linked 2'-β-D-deoxynucleosides in the gap, and 5 linked 2'-MOE nucleosides in the 3'-wing. A 6-10-4 MOE gapmer consists of 6 linked 2'-MOE nucleosides in the 5'-wing, 10 linked 2'-β-D-deoxynucleosides in the gap, and 4 linked 2'-MOE nucleosides in the 3'-wing. A 3-10-3 cEt gapmer consists of 3 linked cEt nucleosides in the 5'-wing, 10 linked 2'-β-D-deoxynucleosides in the gap, and 3 linked cEt nucleosides in the 3'-wing.

In certain embodiments, modified oligonucleotides are 5-10-5 MOE gapmers. In certain embodiments, modified oligonucleotides are 6-10-4 MOE gapmers.

In certain embodiments, modified oligonucleotides have a sugar motif selected from 5' to 3': eeeeeddddddddddeeeee; wherein each "d" represents a 2'-β-D-deoxyribosyl sugar moiety, and each "e" represents a 2'-MOE sugar moiety.

In certain embodiments, modified oligonucleotides have a sugar motif selected from 5' to 3': eeeeeeddddddddddeeee; wherein each "d" represents a 2'-β-D-deoxyribosyl sugar moiety, and each "e" represents a 2'-MOE sugar moiety.

In certain embodiments, modified oligonucleotides have the sugar motif from 5' to 3' kkkddddddddddkkk; wherein each "d" represents a 2'-β-D-deoxyribosyl sugar moiety, and each "k" represents a cEt modified sugar moiety.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each cytosine is modified. In certain embodiments, some or all of the cytosine nucleobases in a modified oligonucleotide are 5-methyl cytosines. In certain embodiments, all of the cytosine nucleobases are 5-methyl cytosines and all of the other nucleobases of the modified oligonucleotide are unmodified nucleobases.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl sugar moiety.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphodiester internucleoside linkage (P=O). In certain embodiments, each internucleoside linking group of a modified oligonucleotide is a phosphorothioate internucleoside linkage (P=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate.

In certain embodiments, the sugar motif of a modified oligonucleotide is a gapmer and the internucleoside linkages within the gap are all modified. In certain such embodiments, some, or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

In certain embodiments, modified oligonucleotides have an internucleoside linkage motif of (5' to 3'): sooossssssssss-sooss phosphorothioate internucleoside linkage, wherein each "s" represents a phosphorothioate internucleoside linkage and each "o" represents a phosphodiester internucleoside linkage. In certain embodiments, modified oligonucleotides have an internucleoside linkage motif of (5' to 3'): sooooosssssssssssoss, wherein each "s" represents a phosphorothioate internucleoside linkage and each "o" represents a phosphodiester internucleoside linkage.

II. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance.

In certain embodiments, conjugation of one or more carbohydrate moieties to a modified oligonucleotide can optimize one or more properties of the modified oligonucleotide. In certain embodiments, the carbohydrate moiety is attached to a modified subunit of the modified oligonucleotide. For example, the ribose sugar of one or more ribonucleotide subunits of a modified oligonucleotide can be replaced with another moiety, e.g. a non-carbohydrate (preferably cyclic) carrier to which is attached a carbohydrate ligand A ribonucleotide subunit in which the ribose sugar of the subunit has been so replaced is referred to herein as a ribose replacement modification subunit (RRMS), which is a modified sugar moiety. A cyclic carrier may be a carbocyclic ring system, i.e., one or more ring atoms may be a heteroatom, e.g., nitrogen, oxygen, sulphur. The cyclic carrier may be a monocyclic ring system, or may contain two or more rings, e.g. fused rings. The cyclic carrier may be a fully saturated ring system, or it may contain one or more double bonds. In certain embodiments, the modified oligonucleotide is a gapmer.

In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., *Proc. Natl. Acad. Sci. USA*, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

In certain embodiments, the conjugate group may comprise a conjugate moiety selected from any of a C22 alkyl, C20 alkyl, C16 alkyl, C10 alkyl, C21 alkyl, C19 alkyl, C18 alkyl, C17 alkyl, C15 alkyl, C14 alkyl, C13 alkyl, C12 alkyl, C11 alkyl, C9 alkyl, C8 alkyl, C7 alkyl, C6 alkyl, C5 alkyl, C22 alkenyl, C20 alkenyl, C16 alkenyl, C10 alkenyl, C21 alkenyl, C19 alkenyl, C18 alkenyl, 17 alkenyl, C15 alkenyl, C14 alkenyl, C13 alkenyl, C12 alkenyl, C11 alkenyl, C9 alkenyl, C8 alkenyl, C7 alkenyl, C6 alkenyl, or C5 alkenyl.

In certain embodiments, the conjugate group may comprise a conjugate moiety selected from any of a C22 alkyl, C20 alkyl, C16 alkyl, C10 alkyl, C21 alkyl, C19 alkyl, C18 alkyl, C17 alkyl, C15 alkyl, C14 alkyl, C13 alkyl, C12 alkyl, C11 alkyl, C9 alkyl, C8 alkyl, C7 alkyl, C6 alkyl, or C5 alkyl, where the alkyl chain has one or more unsaturated bonds.

In certain embodiments, a conjugate group is a lipid having the following structure:

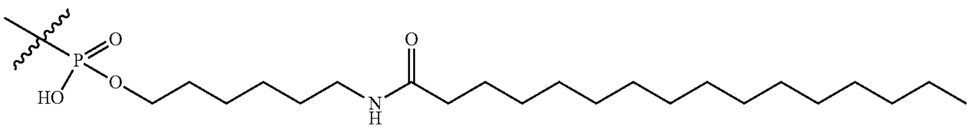 [SMILES: *P(=O)(O)OCCCCCCNC(=O)CCCCCCCCCCCCCCC]

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises pyrrolidine.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises one or more groups selected from alkyl, amino, oxo, amide, and ether groups. In certain embodiments, the conjugate linker comprises one or more groups selected from alkyl and amide groups. In certain embodiments, the conjugate linker comprises one or more groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate moieties to compounds, such as the oligonucleotides provided herein. In general, a bifunctional linking moiety comprises at least two functional groups. One of the functional groups is selected to react with a particular site on a compound and the other is selected to react with a conjugate moiety. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to a substituted or unsubstituted $C_1$-$C_{10}$ alkyl, a substituted or unsubstituted $C_2$-$C_{10}$ alkenyl or a substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl, and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxynucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

3. Cell-Targeting Moieties

In certain embodiments, a conjugate group comprises a cell-targeting moiety. In certain embodiments, a conjugate group has the general formula:

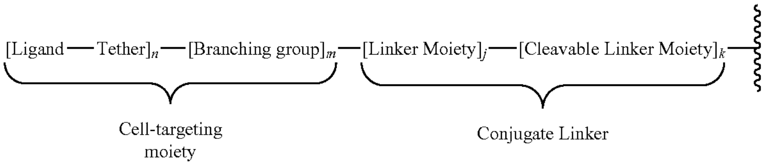

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group.

In certain embodiments, each ligand of a cell-targeting moiety has an affinity for at least one type of receptor on a target cell. In certain embodiments, each ligand has an affinity for at least one type of receptor on the surface of a mammalian liver cell. In certain embodiments, each ligand has an affinity for the hepatic asialoglycoprotein receptor (ASGP-R). In certain embodiments, each ligand is a carbohydrate.

In certain embodiments, a conjugate group comprises a cell-targeting conjugate moiety. In certain embodiments, a conjugate group has the general formula:

[Ligand—Tether]$_n$—[Branching group]$_m$—[Conjugate Linker Moiety]$_j$—[Cleavable Conj.Linker Moiety]$_k$—

Cell-targeting conjugate moiety

Conjugate Linker wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

III. Certain Terminal Groups

In certain embodiments, oligomeric compounds comprise one or more terminal groups. In certain such embodiments, oligomeric compounds comprise a stabilized 5'-phosphate. Stabilized 5'-phosphates include, but are not limited to 5'-phosphonates, including, but not limited to 5'-vinylphosphonates. In certain embodiments, terminal groups comprise one or more abasic sugar moieties and/or inverted nucleosides. In certain embodiments, terminal groups comprise one or more 2'-linked nucleosides or sugar moieties. In certain such embodiments, the 2'-linked group is an abasic sugar moiety.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce or inhibit the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently “DNA-like” to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute Antisense compounds that are loaded into RISC are RNAi compounds. RNAi compounds may be double-stranded (siRNA or dsRNAi) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or animal.

V. Certain Target Nucleic Acids

In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target RNA is a mature mRNA. In certain embodiments, the target nucleic acid is a pre-mRNA. In certain embodiments, the target region is entirely within an intron. In certain embodiments, the target region spans an intron/exon junction. In certain embodiments, the target region is at least 50% within an intron.

A. IFNAR1

In certain embodiments, oligomeric compounds comprise or consist of an oligonucleotide comprising a region that is complementary to a target nucleic acid, wherein the target nucleic acid is an IFNAR1 nucleic acid. In certain embodiments, an IFNAR1 nucleic acid has the sequence set forth in SEQ ID NO: 1 (GENBANK Accession No. NC_000021.9, truncated from 33321001 to 33363000) or SEQ ID NO: 2 (GENBANK Accession No. NM_000629.2). In certain embodiments, contacting a cell with an oligomeric compound complementary to SEQ ID NO: 1 or SEQ ID NO: 2 reduces the amount of IFNAR1 RNA, and in certain embodiments reduces the amount of IFNAR1 protein. In certain embodiments, the oligomeric compound consists of a modified oligonucleotide. In certain embodiments, the oligomeric compound consists of a modified oligonucleotide and a conjugate group.

B. Certain Target Nucleic Acids in Certain Tissues

In certain embodiments, oligomeric compounds comprise or consist of an oligonucleotide comprising a region that is complementary to a target nucleic acid, wherein the target nucleic acid is expressed in a pharmacologically relevant tissue. In certain embodiments, the pharmacologically relevant tissues are the brain and spinal cord. In certain embodiments, the target nucleic acid is expressed in a pharmacologically relevant cell. In certain embodiments the pharmacologically relevant cell is a neuron or a glial cell. In certain embodiments, the pharmacologically relevant cell is an astrocyte or a microglial cell. In certain embodiments, the pharmacologically relevant cell is a vascular smooth muscle cell a vascular endothelial cell, or a pericyte.

VI. Certain Methods and Uses

Certain embodiments provided herein relate to methods of inhibiting IFNAR1 expression, which can be useful for treating a disease associated with neuroinflammation, for example, a disease associated with elevated type I interferon signaling, or with over-expression of a type I interferons in a subject, by administration of an oligomeric compound, modified oligonucleotide, or oligomeric duplex, any of which comprising a modified oligonucleotide having a nucleobase sequence complementary to an IFNAR1 nucleic acid.

Examples of diseases treatable with the oligomeric compounds, modified oligonucleotides, oligomeric duplexes, and methods provided herein include neurological diseases or conditions associated with neuroinflammation, for example, a disease associated with elevated type I interferon signaling, or with over-expression of type I interferons, selected from Aicardi-Goutières Syndrome, stroke, neuropsychiatric systemic lupus erythematosus, neuroinflammation following traumatic brain injury, neuro-autoimmune disorders, Alzheimer's disease, post-operative delirium and cognitive decline, cranial radiation-induced cognitive decline, viral infection-induced cognitive decline, neuromyelitis optica, and ataxia telangiectasia. In certain embodiments, a method comprises administering to a subject an oligomeric compound, a modified oligonucleotide, or an oligomeric duplex, any of which having a nucleobase sequence complementary to an IFNAR1 nucleic acid. In certain embodiments, the subject has a neurological disease or condition associated with neuroinflammation selected from Aicardi-Goutières Syndrome, stroke, neuropsychiatric systemic lupus erythematosus, neuroinflammation following traumatic brain injury, neuro-autoimmune disorders, Alzheimer's disease, post-operative delirium and cognitive decline, cranial radiation-induced cognitive decline, viral infection-induced cognitive decline, neuromyelitis optica, and ataxia telangiectasia. In certain embodiments, a method of treating neurological diseases or conditions associated with neuroinflammation selected from Aicardi-Goutières Syndrome, stroke, neuropsychiatric systemic lupus erythematosus, neuroinflammation following traumatic brain injury, neuro-autoimmune disorders, Alzheimer's disease, post-operative delirium and cognitive decline, cranial radiation-induced cognitive decline, viral infection-induced cognitive decline, neuromyelitis optica, and ataxia telangiectasia in a subject comprises administering to the subject a therapeutically effective amount of an oligomeric compound, a modified oligonucleotide, or an oligomeric duplex, any of which having a nucleobase sequence complementary to an IFNAR1 nucleic acid, thereby treating the subject. In certain embodiments, administering the therapeutically effective amount of the oligomeric compound, or modified oligonucleotide improves a symptom or hallmark of a disease or condition associated with neuroinflammation. In certain embodiments, the symptom or hallmark is selected from seizures, difficulty feeding, dystonia, spasticity, delayed motor development, delayed language development, delayed social skill development, white matter abnormalities, T cell infiltration, B cell infiltration, striatal necrosis, brain atrophy, basal ganglia calcification, and microencephaly. In certain embodiments, administering the therapeutically effective amount of the oligomeric compound or the modified oligonucleotide reduces type I IFN signaling or lymphocytosis in cerebrospinal fluid in the subject.

In certain embodiments, a method of inhibiting expression of IFNAR1 nucleic acid, such as RNA, in a subject having a disease associated with neuroinflammation, for example, a disease associated with elevated type I interferon signaling, or with over-expression of type I interferons, comprises administering to the subject an oligomeric compound, a modified oligonucleotide, or an oligomeric duplex, any of which having a nucleobase sequence complementary to an IFNAR1 nucleic acid, thereby inhibiting expression of IFNAR1 nucleic acid in the subject. In certain embodiments, administering the oligomeric compound, modified oligonucleotide, or oligomeric duplex inhibits expression of IFNAR1 in the brain or spinal cord. In certain embodiments, the subject has a neurological disease or condition associated with neuroinflammation selected from Aicardi-Goutières Syndrome, stroke, neuropsychiatric systemic lupus erythematosus, neuroinflammation following traumatic brain injury, neuro-autoimmune disorders, Alzheimer's disease, post-operative delirium and cognitive decline, cranial radiation-induced cognitive decline, viral infection-induced cognitive decline, neuromyelitis optica, and ataxia telangiectasia. In certain embodiments, a method of inhibiting expression of IFNAR1 nucleic acid in a cell comprises contacting the cell with an oligomeric compound, a modified oligonucleotide, or an oligomeric duplex, any of which having a nucleobase sequence complementary to an IFNAR1 nucleic acid, thereby inhibiting expression of IFNAR1 nucleic acid in the cell. In certain embodiments, the cell is glial cell, for example, an astrocyte or a microglial cell. In certain embodiments, the cell is in a subject having a neurological disease or condition associated with neuroinflammation selected from Aicardi-Goutières Syndrome, stroke, neuropsychiatric systemic lupus erythematosus, neuroinflammation following traumatic brain injury, neuro-autoimmune disorders, Alzheimer's disease, post-operative delirium and cognitive decline, cranial radiation-induced cognitive decline, viral infection-induced cognitive decline, neuromyelitis optica, and ataxia telangiectasia.

Certain embodiments are drawn to an oligomeric compound, a modified oligonucleotide, or an oligomeric duplex, any of which having a nucleobase sequence complementary to an IFNAR1 nucleic acid, for use in treating a disease associated with neuroinflammation associated with neuroinflammation, for example, a disease associated with elevated type I interferon signaling, or with over-expression of IFNa. In certain embodiments, the disease is a neurological disease or condition associated with neuroinflammation selected from Aicardi-Goutières Syndrome, stroke, neuropsychiatric systemic lupus erythematosus, neuroinflammation following traumatic brain injury, neuro-autoimmune disorders, Alzheimer's disease, post-operative delirium and cognitive decline, cranial radiation-induced cognitive decline, viral infection-induced cognitive decline, neuromyelitis optica, and ataxia telangiectasia. In certain embodiments, an oligomeric compound, a modified oligonucleotide, or an oligomeric duplex is for use in improving a symptom or hallmark of a disease or condition associated with neuroinflammation selected from Aicardi-Goutières Syndrome, stroke, neuropsychiatric systemic lupus erythematosus, neuroinflammation following traumatic brain injury, neuro-autoimmune disorders, Alzheimer's disease, post-operative delirium and cognitive decline, cranial radiation-induced cognitive decline, viral infection-induced cognitive decline, neuromyelitis optica, and ataxia telangiectasia. In certain embodiments, the symptom or hallmark is selected from seizures, difficulty feeding, dystonia, spasticity, delayed motor development, delayed language development, delayed social skill development, white matter abnormalities, T cell infiltration, B cell infiltration, striatal necrosis, brain atrophy, basal ganglia calcification, and microencephaly. In certain embodiments, an oligomeric compound, a modified oligonucleotide, or an oligomeric duplex is for use in reducing type I IFN signaling or lymphocytosis in the cerebrospinal fluid in a subject.

Certain embodiments are drawn to an oligomeric compound, a modified oligonucleotide, or an oligomeric duplex, any of which comprising a modified oligonucleotide having a nucleobase sequence complementary to an IFNAR1 nucleic acid, for the manufacture or preparation of a medicament for treating a disease associated with neuroinflammation, for example, a disease associated with elevated type I interferon signaling, or with over-expression of IFNa. In certain embodiments, the disease is a neurological disease or condition associated with neuroinflammation selected from Aicardi-Goutières Syndrome, stroke, neuropsychiatric systemic lupus erythematosus, neuroinflammation following traumatic brain injury, neuro-autoimmune disorders, Alzheimer's disease, post-operative delirium and cognitive decline, cranial radiation-induced cognitive decline, viral infection-induced cognitive decline, neuromyelitis optica, and ataxia telangiectasia. In certain embodiments, an oligomeric compound, a modified oligonucleotide, or an oligomeric duplex is for the manufacture or preparation of a medicament for improving symptoms or hallmarks associated with Aicardi-Goutières Syndrome, stroke, neuropsychiatric systemic lupus erythematosus, neuroinflammation following traumatic brain injury, neuro-autoimmune disorders, Alzheimer's disease, post-operative delirium and cognitive decline, cranial radiation-induced cognitive decline, viral infection-induced cognitive decline, neuromyelitis optica, and ataxia telangiectasia. In certain embodiments, the symptom or hallmark is selected from seizures, difficulty feeding, dystonia, spasticity, delayed motor development, delayed language development, delayed social skill development, white matter abnormalities, T cell infiltration, B cell infiltration, striatal necrosis, brain atrophy, basal ganglia calcification, and microencephaly. In certain embodiments, an oligomeric compound, a modified oligonucleotide, or an oligomeric duplex is for the manufacture or preparation of a medicament for use in reducing type I IFN signaling or lymphocytosis in the cerebrospinal fluid in a subject.

In any of the methods or uses described herein, the oligomeric compound, modified oligonucleotide, or oligomeric duplex can be any described herein.

VII. Certain Pharmaceutical Compositions

In certain embodiments, described herein are pharmaceutical compositions comprising one or more oligomeric compounds. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a sterile saline solution and one or more oligomeric compound. In certain embodiments, the sterile saline is pharmaceutical grade saline. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, the sterile PBS is pharmaceutical grade PBS. In certain embodiments, a pharmaceutical composition comprises or consists of one or more oligomeric compound and artificial cerebrospinal fluid. In certain embodiments, the artificial cerebrospinal fluid is pharmaceutical grade artificial cerebrospinal fluid.

In certain embodiments, a pharmaceutical composition comprises a modified oligonucleotide and PBS. In certain embodiments, a pharmaceutical composition consists of a modified oligonucleotide and PBS. In certain embodiments, a pharmaceutical composition consists essentially of a modified oligonucleotide and PBS. In certain embodiments, the PBS is pharmaceutical grade.

In certain embodiments, a pharmaceutical composition comprises a modified oligonucleotide and artificial cerebrospinal fluid. In certain embodiments, a pharmaceutical composition consists of a modified oligonucleotide and artificial cerebrospinal fluid. In certain embodiments, a pharmaceutical composition consists essentially of a modified oligonucleotide and artificial cerebrospinal fluid. In certain embodiments, the artificial cerebrospinal fluid is pharmaceutical grade.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose, and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to an animal, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Under certain conditions, certain compounds disclosed herein act as acids. Although such compounds may be drawn or described in protonated (free acid) form, or ionized and in association with a cation (salt) form, aqueous solutions of such compounds exist in equilibrium among such forms. For example, a phosphate linkage of an oligonucleotide in aqueous solution exists in equilibrium among free acid, anion and salt forms. Unless otherwise indicated, compounds described herein are intended to include all such forms. Moreover, certain oligonucleotides have several such linkages, each of which is in equilibrium. Thus, oligonucleotides in solution exist in an ensemble of forms at multiple positions all at equilibrium. The term "oligonucleotide" is intended to include all such forms. Drawn structures necessarily depict a single form. Nevertheless, unless otherwise indicated, such drawings are likewise intended to include corresponding forms. Herein, a structure depicting the free acid of a compound followed by the term "or a salt thereof" expressly includes all such forms that may be fully or partially protonated/de-protonated/in association with a cation. In certain instances, one or more specific cation is identified.

In certain embodiments, modified oligonucleotides or oligomeric compounds are in aqueous solution with sodium. In certain embodiments, modified oligonucleotides or oligomeric compounds are in aqueous solution with potassium. In certain embodiments, modified oligonucleotides or oligomeric compounds are in PBS. In certain embodiments, modified oligonucleotides or oligomeric compounds are in water. In certain such embodiments, the pH of the solution is adjusted with NaOH and/or HCl to achieve a desired pH.

Herein, certain specific doses are described. A dose may be in the form of a dosage unit. For clarity, a dose (or dosage unit) of a modified oligonucleotide or an oligomeric compound in milligrams indicates the mass of the free acid form of the modified oligonucleotide or oligomeric compound. As described above, in aqueous solution, the free acid is in equilibrium with anionic and salt forms. However, for the purpose of calculating dose, it is assumed that the modified oligonucleotide or oligomeric compound exists as a solvent-free, sodium-acetate free, anhydrous, free acid. For example, where a modified oligonucleotide or an oligomeric compound is in solution comprising sodium (e.g., saline), the modified oligonucleotide or oligomeric compound may be partially or fully de-protonated and in association with Na+ ions. However, the mass of the protons are nevertheless counted toward the weight of the dose, and the mass of the Na+ ions are not counted toward the weight of the dose. Thus, for example, a dose, or dosage unit, of 10 mg of Compound No. 1492069, equals the number of fully protonated molecules that weighs 10 mg. This would be equivalent to 10.59 mg of solvent-free, sodium acetate-free, anhydrous sodiated Compound No. 1492069. When an oligomeric compound comprises a conjugate group, the mass of the conjugate group is included in calculating the dose of such oligomeric compound. If the conjugate group also has an acid, the conjugate group is likewise assumed to be fully protonated for the purpose of calculating dose.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, ENSEMBL identifiers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of an uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^{m}$CGAUCG," wherein $^{m}$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, tautomeric forms of the compounds herein are also included unless otherwise indicated. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^{1}$H hydrogen atoms. Isotopic substitutions encompassed by the compounds herein include but are not limited to: $^{2}$H or $^{3}$H in place of $^{1}$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Design of Modified Oligonucleotides Complementary to Human IFNAR1 Nucleic Acid Modified oligonucleotides complementary to a human IFNAR1 nucleic acid were designed, as described in the tables below. "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence. Each modified oligonucleotide listed in the tables below is 100% complementary to SEQ ID NO 1 (GENBANK Accession No. NC_000021.9, truncated from 33321001 to 33363000), to SEQ ID NO 2 (GENBANK Accession No. NM_000629.2), or to both. 'N/A' indicates that the modified oligonucleotide is not 100% complementary to that particular target nucleic acid sequence.

The modified oligonucleotides in the table below are 5-10-5 MOE gapmers. The gapmers are 20 nucleosides in length, wherein the sugar motif for the gapmers is (from 5' to 3'): eeeeeddddddddddeeeee; wherein each "d" represents a 2'-β-D-deoxyribosyl sugar moiety, and each "e" represents a 2'-MOE sugar moiety. The gapmers have an internucleoside linkage motif of (from 5' to 3'): sooosssssssssssooss; wherein each "s" represents a phosphorothioate internucleoside linkage, and each "o" represents a phosphodiester internucleoside linkage. Each cytosine residue is a 5-methyl cytosine.

TABLE 1

5-10-5 MOE gapmers with mixed PO/PS internucleoside linkages complementary to human IFNAR1

| Compound Number | Sequence (5' to 3') | SEQ ID NO 1 Start Site | SEQ ID NO 1 Stop Site | SEQ ID NO 2 Start Site | SEQ ID NO 2 Stop Site | SEQ ID NO |
|---|---|---|---|---|---|---|
| 1489525 | TTTATCCAATTATCCATCCC | 20003 | 20022 | 352 | 371 | 9 |
| 1492069 | TCGCCTAATTTTTCTCTCAC | 22455 | 22474 | N/A | N/A | 10 |
| 1492037 | TTTGCATATGTATAATCCCA | 24314 | 24333 | 889 | 908 | 15 |

The modified oligonucleotides in the table below are 6-10-4 MOE gapmers. The gapmers are 20 nucleosides in length, wherein the sugar motif for the gapmers is (from 5' to 3'): eeeeeedddddddddddeeee; wherein each "d" represents a 2'-β-D-deoxyribosyl sugar moiety, and each "e" represents a 2'-MOE sugar moiety. The gapmers have an internucleoside linkage motif of (from 5' to 3'): soooossssssssssssoss; wherein each "s" represents a phosphorothioate internucleoside linkage, and each "o" represents a phosphodiester internucleoside linkage. Each cytosine residue is a 5-methyl cytosine.

TABLE 2

6-10-4 MOE gapmers with mixed PO/PS internucleoside linkages complementary to human IFNAR1

| Compound Number | Sequence (5' to 3') | SEQ ID NO 1 Start Site | SEQ ID NO 1 Stop Site | SEQ ID NO 2 Start Site | SEQ ID NO 2 Stop Site | SEQ ID NO |
|---|---|---|---|---|---|---|
| 1489477 | CTTTTTCTGCTCTTATACGC | 2010420123 | | 453 | 472 | 11 |
| 1489494 | CTGTTTTACATTTTTTTTCC | 2059120610 | | N/A | N/A | 12 |
| 1492082 | TTTCATATTTGTTACTTCCT | 2998130000 | | N/A | N/A | 13 |
| 1492131 | TTCGCCTAATTTTTCTCTCA | 2245622475 | | N/A | N/A | 14 |

Example 2: Activity of Modified Oligonucleotides Complementary to Human IFNAR1 in Transgenic Mice Modified oligonucleotides described above were tested in a human IFNAR1 transgenic mouse model. Transgenic mice that express a human IFNAR1 transcript were generated.

Exons 1-6 and ~4.9 kB of upstream sequence of the human IFNAR1 gene from fosmid ABCS-41091_400N2 was subcloned into a BAC, CTD-2289N21, containing exons 7-11 of the human IFNAR1 genes and 56 kB of downstream sequence, to generate a complete IFNAR1 transgene. The engineered BAC was digested with Not1 to remove the BAC backbone. The purified BAC fragment, containing the complete human IFNAR1 gene, was introduced into fertilized eggs from C57BL/6 mice by pronuclear injection to produce three founder lines. Line 17505 was used in the experiments described herein.

Treatment

Transgenic mice were divided into groups of 2 mice each. Each mouse received a single ICV bolus of 300 μg of modified oligonucleotide. A group of 2-4 mice received PBS as a negative control.

RNA Analysis

Two weeks post treatment, mice were sacrificed, and RNA was extracted from cortical brain tissue and spinal cord for RTPCR analysis to measure amount of IFNAR1 RNA using human primer probe set RTS44352 (forward sequence CTTTCAAGTTCAGTGGCTCCA, designated herein as SEQ ID NO 6; reverse sequence CGTTTTGAGGAAAGACACACTG, designated herein as SEQ ID NO 7; probe sequence AGTTTTGACATTTTCACAGTCAGGTATTTGTTTCC, designated herein as SEQ ID NO 8). Results are presented as percent human IFNAR1 relative to PBS control, normalized to 18S ribosomal RNA. 18S ribosomal RNA was amplified using mouse 18S prime probe set PPS54360 (forward sequence GGAACTGAGGCCATGATTAAGA, designated herein as SEQ ID NO: 3; reverse sequence ACCTCCGACTTTCGTTCTTG, designated herein as SEQ ID NO: 4; probe sequence AAGACGGACCAGAGCGAAAGCAT, designated herein as SEQ ID NO: 5).

TABLE 3

Reduction of human IFNAR1 RNA in transgenic mice (n = 2) treated with 300 μg of modified oligonucleotide

| | IFNAR1 RNA (% control) | |
|---|---|---|
| Compound ID | Spinal Cord | Cortex |
| PBS | 100 | 100 |
| 1489494 | 18 | 8 |
| 1489525 | 32 | 25 |
| 1492069 | 23 | 24 |
| 1492131 | 20 | 28 |

‡ Indicates fewer than 2 samples available

TABLE 4

Reduction of human IFNAR1 RNA in transgenic mice (n = 2) treated with 300 μg of modified oligonucleotide

| | IFNAR1 RNA (% control) | |
|---|---|---|
| Compound ID | Spinal Cord | Cortex |
| PBS | 100 | 100 |
| 1489477 | 32 | 27 |
| 1492082 | 19 | 10 |
| 1492069 | 20 | 18 |

Example 3: Potency of Modified Oligonucleotides Complementary to Human IFNAR1 RNA in Transgenic Mice Modified oligonucleotides described above were tested in human IFNAR1 transgenic mice (described herein above).

Treatment

Human IFNAR1 transgenic mice were divided into groups of 4 mice each. Each mouse received a single ICV bolus of modified oligonucleotide at the doses indicated in tables below. A group of 4 mice received PBS as a negative control.

RNA Analysis

Two weeks post treatment, mice were sacrificed, and RNA was extracted from the spinal cord, cortex, and cerebellum for quantitative real-time RTPCR analysis of RNA expression of IFNAR1 using primer probe set RTS44352 (described herein above). Results are presented as percent human IFNAR1 RNA relative to PBS control, adjusted to 18S PCR (described herein above).

The half maximal effective dose (EDO of each modified oligonucleotide was calculated using GraphPad Prism 7 software (GraphPad Software, San Diego, Calif.). $ED_{50}$ values were calculated from dose and individual animal IFNAR1 RNA levels using custom equation: Agonist vs response—Variable slope (four parameters) Y=Bottom+(Top−Bottom)/(1+(10^log ED50/X)^HillSlope), with the following constraints: bottom>0, top=100.

As shown in the table below, treatment with modified oligonucleotides resulted in dose-responsive reduction of IFNAR1 RNA in comparison to the PBS control.

TABLE 5

Reduction of human IFNAR1 RNA in transgenic mice

| Compound ID | Dose (μg) | Spinal Cord IFNAR1 RNA (% control) | Spinal Cord $ED_{50}$ (μg) | Cortex IFNAR1 RNA (% control) | Cortex $ED_{50}$ (μg) | Cerebellum IFNAR1 RNA (% control) | Cerebellum $ED_{50}$ (μg) |
|---|---|---|---|---|---|---|---|
| PBS | N/A | 100 | N/A | 100 | N/A | 100 | N/A |
| 1489494 | 10 | 100 | 79 | 85 | 92 | 81 | 105 |
| | 30 | 73 | | 83 | | 75 | |
| | 100 | 49 | | 50 | | 51 | |
| | 300 | 22 | | 15 | | 31 | |
| | 700 | 13 | | 6 | | 19 | |
| 1489525 | 10 | 77 | 319 | 79 | 31 | 78 | 215 |
| | 30 | 60 | | 32 | | 51 | |
| | 100 | 75 | | 63 | | 71 | |
| | 300 | 50 | | 24 | | 46 | |
| | 700 | 43 | | 21 | | 37 | |
| 1492037 | 10 | 118 | 114 | 85 | 88 | 81 | 133 |
| | 30 | 73 | | 39 | | 64 | |
| | 100 | 60 | | 37 | | 61 | |
| | 300 | 37 | | 24 | | 43 | |
| | 700 | 26 | | 16 | | 29 | |
| 1492069 | 10 | 96 | 104 | 84 | 47 | 74 | 129 |
| | 30 | 80 | | 69 | | 75 | |
| | 100 | 60 | | 34 | | 48 | |
| | 300 | 28 | | 20 | | 43 | |
| | 700 | 23‡ | | 12 | | 29 | |
| 1492082 | 10 | 98 | 177 | 75 | 50 | 76 | 142 |
| | 30 | 53 | | 46 | | 55 | |
| | 100 | 71 | | 46 | | 66 | |
| | 300 | 41 | | 15 | | 39 | |
| | 700 | 29 | | 14 | | 33 | |
| 1492131 | 10 | 114 | 83 | 77 | 32 | 77 | 105 |
| | 30 | 92 | | 63 | | 68 | |
| | 100 | 57 | | 24 | | 48 | |
| | 300 | 39 | | 21 | | 40 | |
| | 700 | 27 | | 13 | | 23 | |

‡Indicates fewer than 4 samples available

TABLE 6

Reduction of human IFNAR1 RNA in transgenic mice

| Compound ID | Dose (μg) | Spinal Cord IFNAR1 RNA (% control) | Spinal Cord $ED_{50}$ (μg) | Cortex IFNAR1 RNA (% control) | Cortex $ED_{50}$ (μg) | Cerebellum IFNAR1 RNA (% control) | Cerebellum $ED_{50}$ (μg) |
|---|---|---|---|---|---|---|---|
| PBS | N/A | 100 | N/A | 100 | N/A | 100 | N/A |
| 1489477 | 10 | 86 | 91.9 | 100‡ | 245 | 98 | 480 |
| | 30 | 77 | | 96 | | 88 | |
| | 100 | 54 | | 72 | | 74 | |
| | 300 | 29 | | 51 | | 62 | |
| | 700 | 24 | | 28 | | 41 | |

‡Indicates fewer than 4 samples available

The invention claimed is:
1. A modified oligonucleotide according to the following chemical structure:
(SEQ ID NO 10)
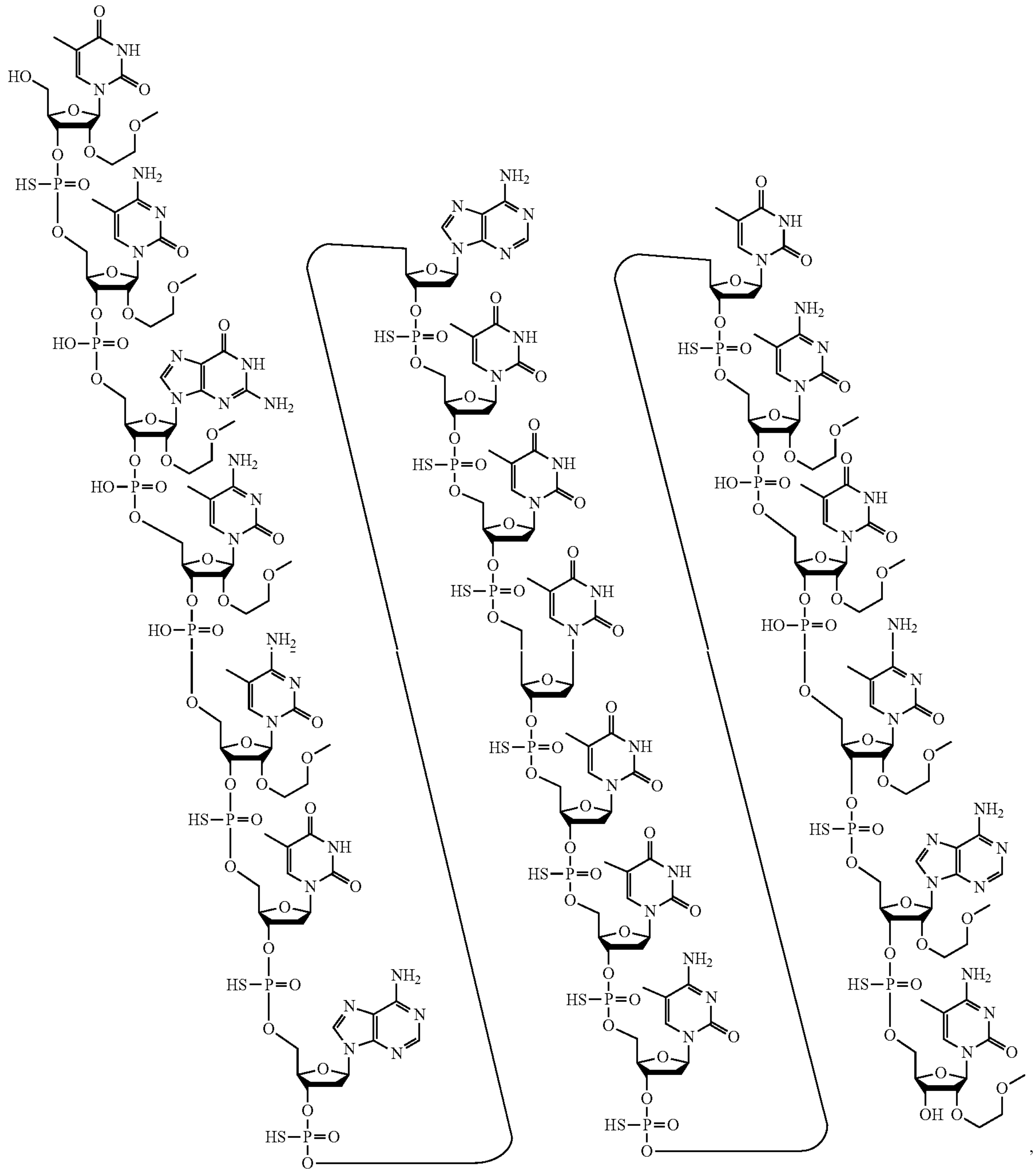
,
or a salt thereof.
2. The modified oligonucleotide of claim 1, which is the sodium salt or the potassium salt.

3. A modified oligonucleotide according to the following chemical structure:

(SEQ ID NO 10)

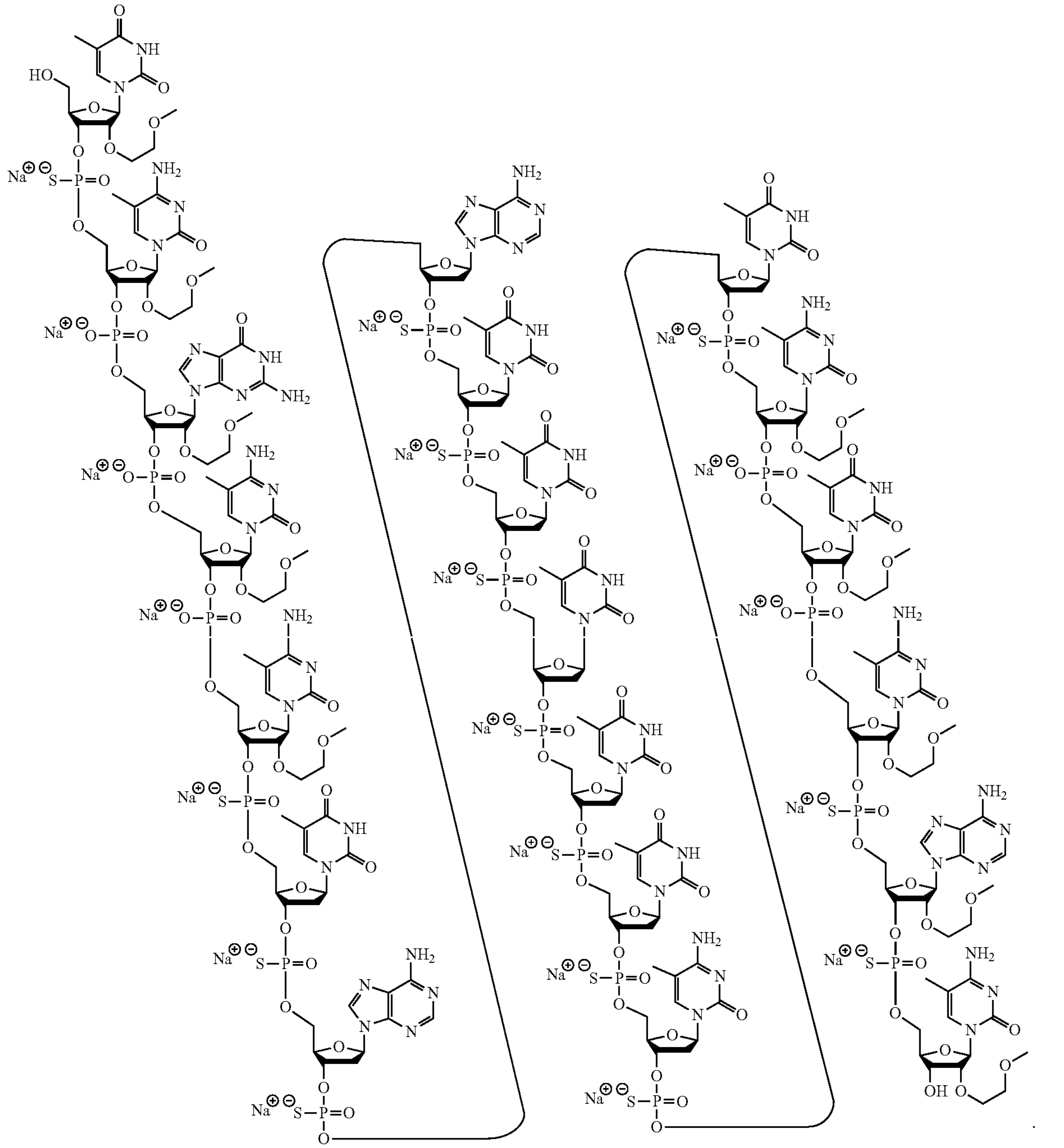

4. An oligomeric compound comprising a modified oligonucleotide according to the following chemical notation: $T_{es}{}^{m}C_{eo}G_{eo}{}^{m}C_{eo}{}^{m}C_{es}T_{ds}A_{ds}A_{ds}T_{ds}T_{ds}T_{ds}T_{ds}T_{ds}{}^{m}C_{ds}T_{ds}{}^{m}C_{eo}T_{eo}{}^{m}C_{es}A_{es}{}^{m}C_{e}$ (SEQ ID NO 10), wherein:

A=an adenine nucleobase, $^{m}$C=a 5-methyl cytosine nucleobase,

G=a guanine nucleobase,

T=a thymine nucleobase, e=a 2'-MOE sugar moiety, d=a 2'-ß-D-deoxyribosyl sugar moiety, s=a phosphorothioate internucleoside linkage, and o=a phosphodiester internucleoside linkage.

5. A population of modified oligonucleotides of claim 1, wherein all of the phosphorothioate internucleoside linkages of the modified oligonucleotide are stereorandom.

6. A pharmaceutical composition comprising a modified oligonucleotide of claim 1, and a pharmaceutically acceptable diluent.

7. The pharmaceutical composition of claim 6, wherein the pharmaceutically acceptable diluent is artificial cerebrospinal fluid, phosphate-buffered saline, or water.

8. The pharmaceutical composition of claim 7, wherein the pharmaceutical composition consists essentially of the modified oligonucleotide, and artificial cerebrospinal fluid, phosphate-buffered saline, or water.

9. A population of modified oligonucleotides of claim 3, wherein all of the phosphorothioate internucleoside linkages of the modified oligonucleotide are stereorandom.

10. A pharmaceutical composition comprising a modified oligonucleotide of claim 3, and a pharmaceutically acceptable diluent.

11. The pharmaceutical composition of claim 10, wherein the pharmaceutically acceptable diluent is artificial cerebrospinal fluid, phosphate-buffered saline, or water.

12. The pharmaceutical composition of claim 11, wherein the pharmaceutical composition consists essentially of the modified oligonucleotide, and artificial cerebrospinal fluid, phosphate-buffered saline, or water.

13. A population of oligomeric compounds of claim 4, wherein all of the phosphorothioate internucleoside linkages of the modified oligonucleotide are stereorandom.

14. A pharmaceutical composition comprising an oligomeric compound of claim 4, and a pharmaceutically acceptable diluent.

15. The pharmaceutical composition of claim 14, wherein the pharmaceutically acceptable diluent is artificial cerebrospinal fluid, phosphate-buffered saline, or water.

16. The pharmaceutical composition of claim 15, wherein the pharmaceutical composition consists essentially of the oligomeric compound, and artificial cerebrospinal fluid, phosphate-buffered saline, or water.

17. A pharmaceutical composition comprising a population of modified oligonucleotides of claim 5, and a pharmaceutically acceptable diluent.

18. The pharmaceutical composition of claim 17, wherein the pharmaceutically acceptable diluent is artificial cerebrospinal fluid, phosphate-buffered saline, or water.

19. A pharmaceutical composition comprising a population of modified oligonucleotides of claim 9, and a pharmaceutically acceptable diluent.

20. The pharmaceutical composition of claim 19, wherein the pharmaceutically acceptable diluent is artificial cerebrospinal fluid, phosphate-buffered saline, or water.

21. A pharmaceutical composition comprising a population of oligomeric compounds of claim 13 and a pharmaceutically acceptable diluent.

22. The pharmaceutical composition of claim 21, wherein the pharmaceutically acceptable diluent is artificial cerebrospinal fluid, phosphate-buffered saline, or water.

* * * * *

UNITED STATES PATENT AND TRADEMARK OFFICE

CERTIFICATE OF CORRECTION

PATENT NO. : 11,753,644 B2
APPLICATION NO. : 17/842960
DATED : September 12, 2023
INVENTOR(S) : Fredrik Carl Kamme It is certified that error appears in the above-identified patent and that said Letters Patent is hereby corrected as shown below:

In the Specification

Columns 35-36, change:

"

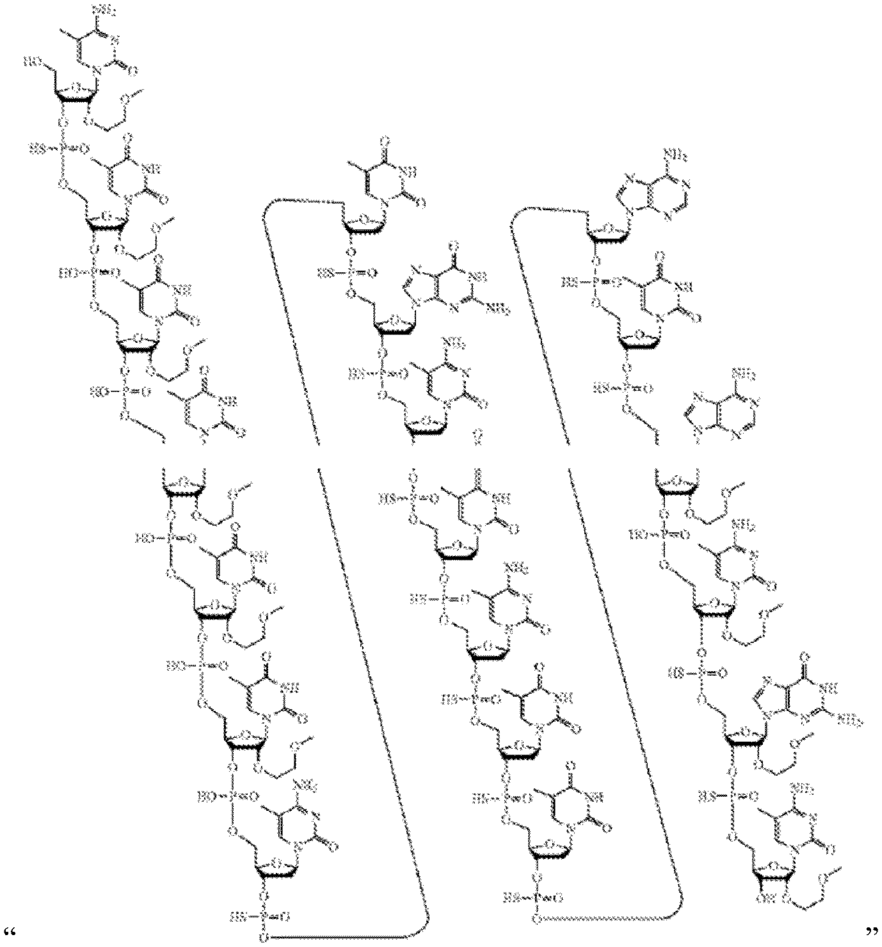

"

Signed and Sealed this
Twenty-eighth Day of November, 2023

Katherine Kelly Vidal

Katherine Kelly Vidal
*Director of the United States Patent and Trademark Office*

To:
-- 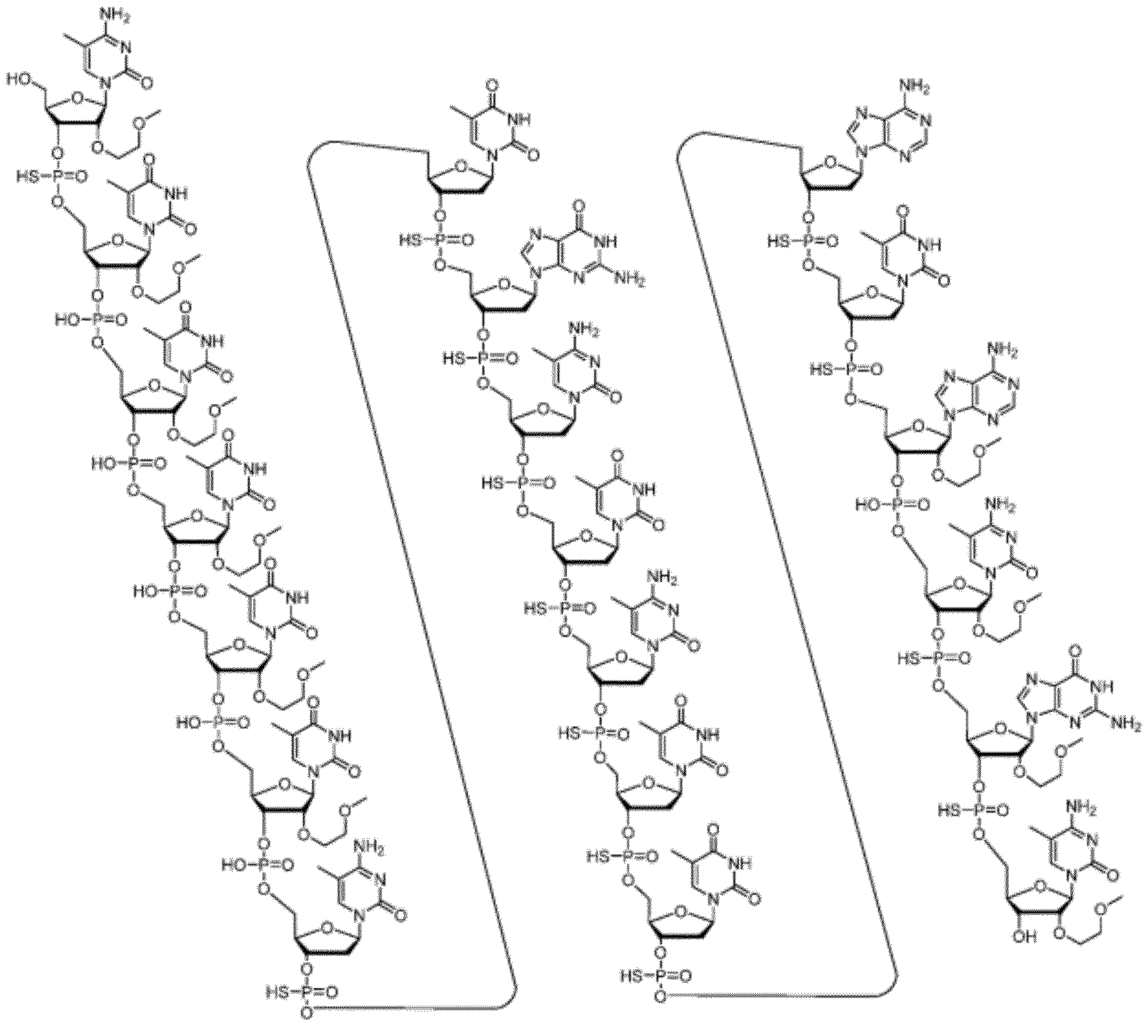 --.

Columns 37-38, change:
“ 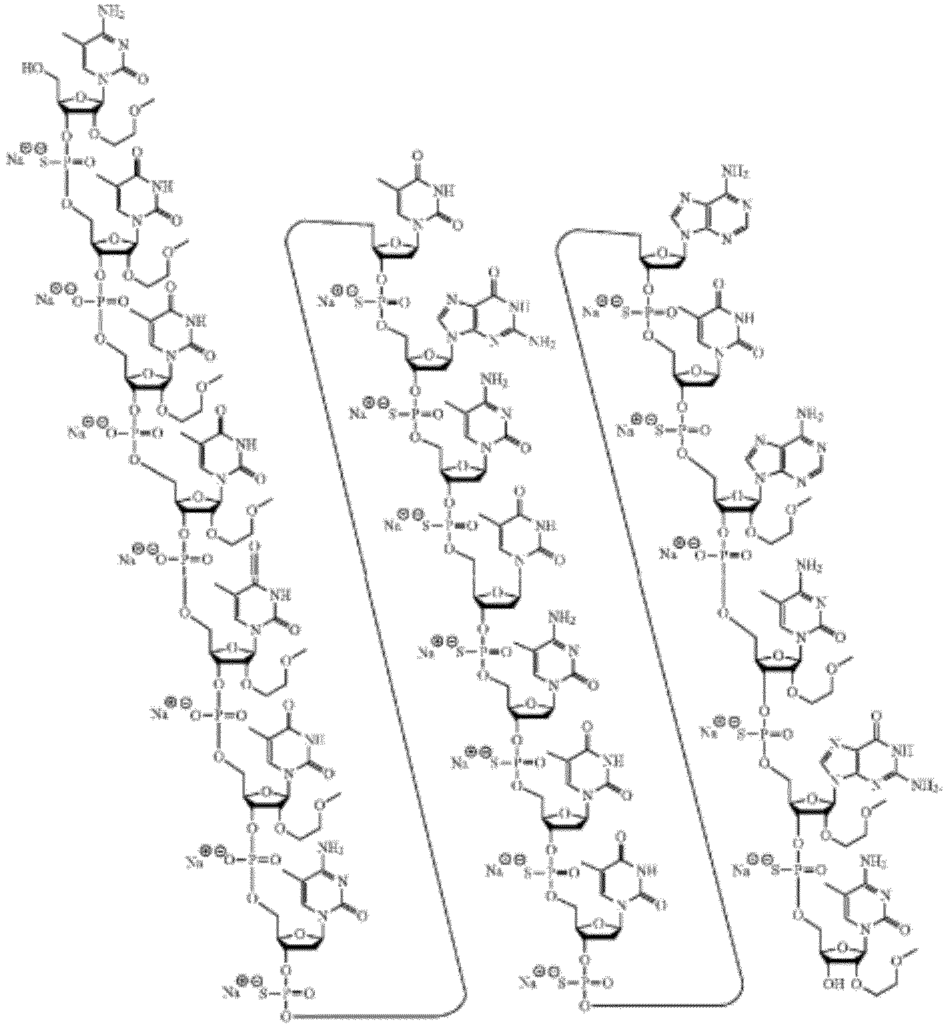 ”

To:
--
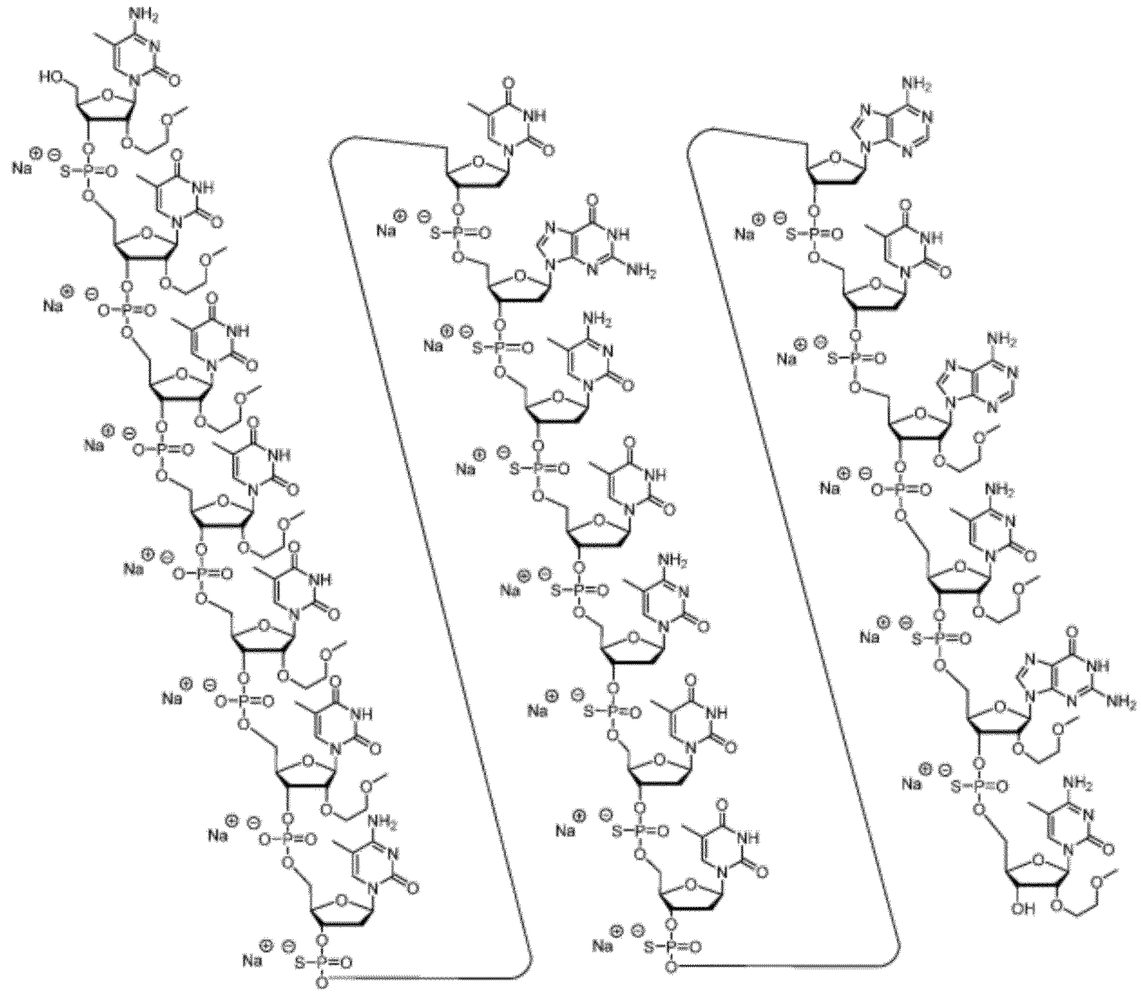
--.
Columns 39-40, change:

“ 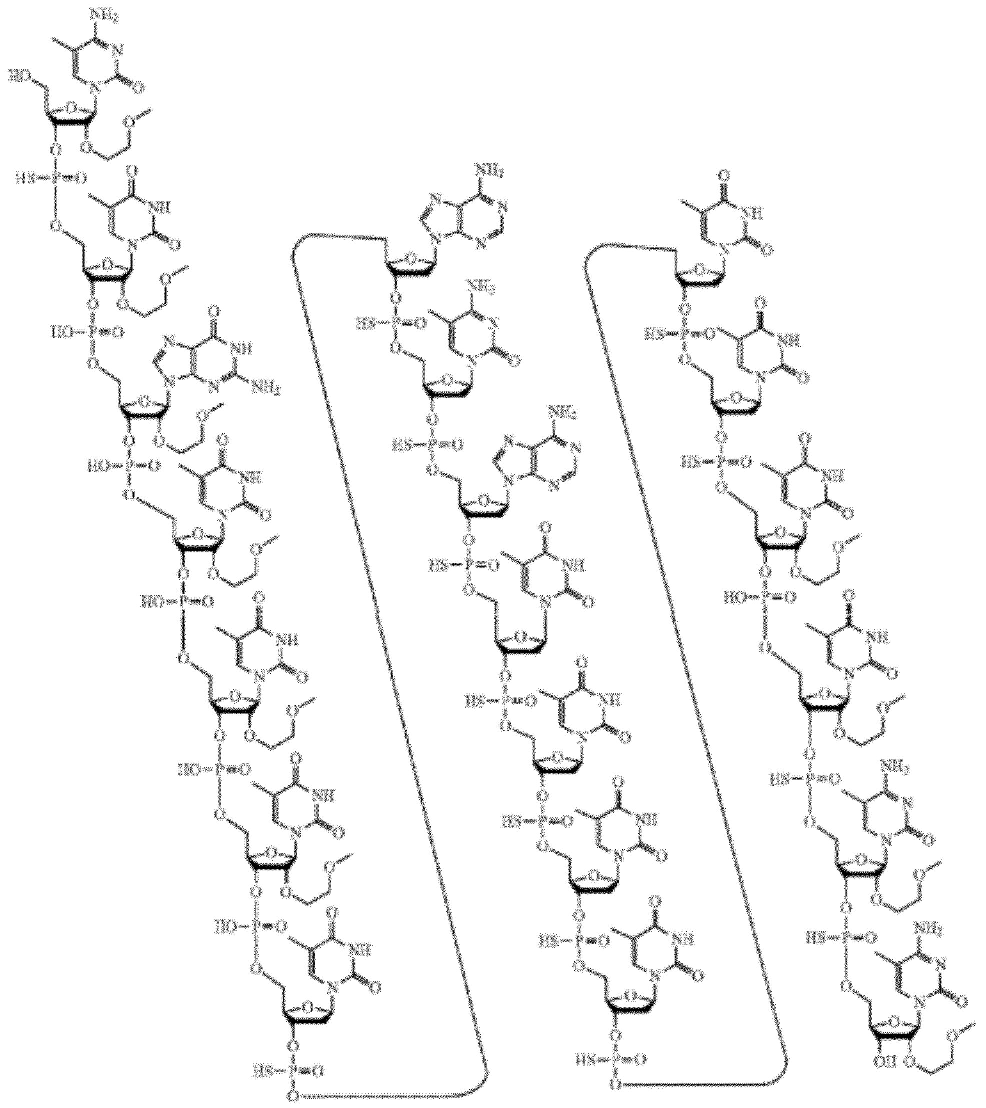 ”
To:

--
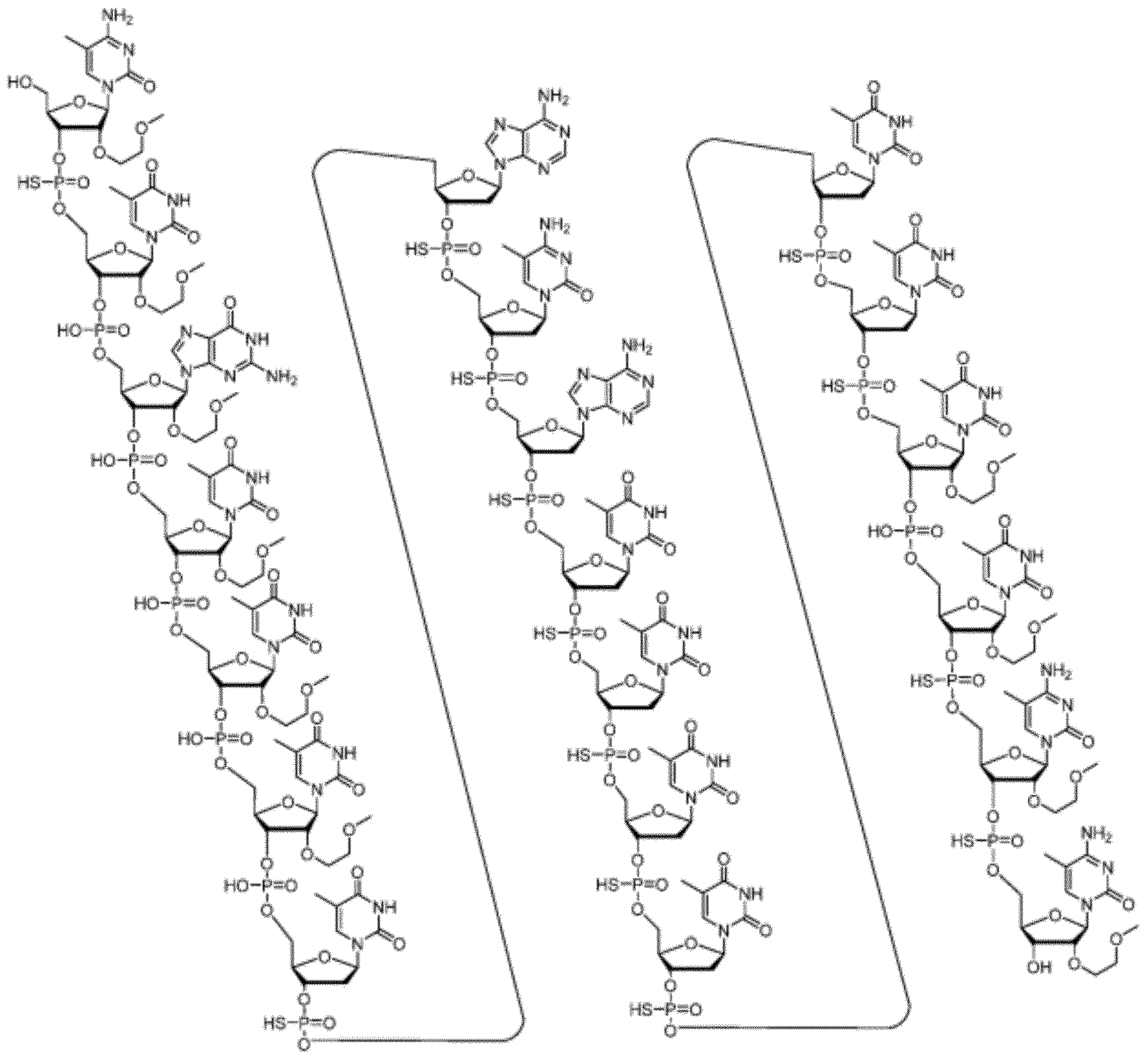
--.
Columns 41-42, change:

"
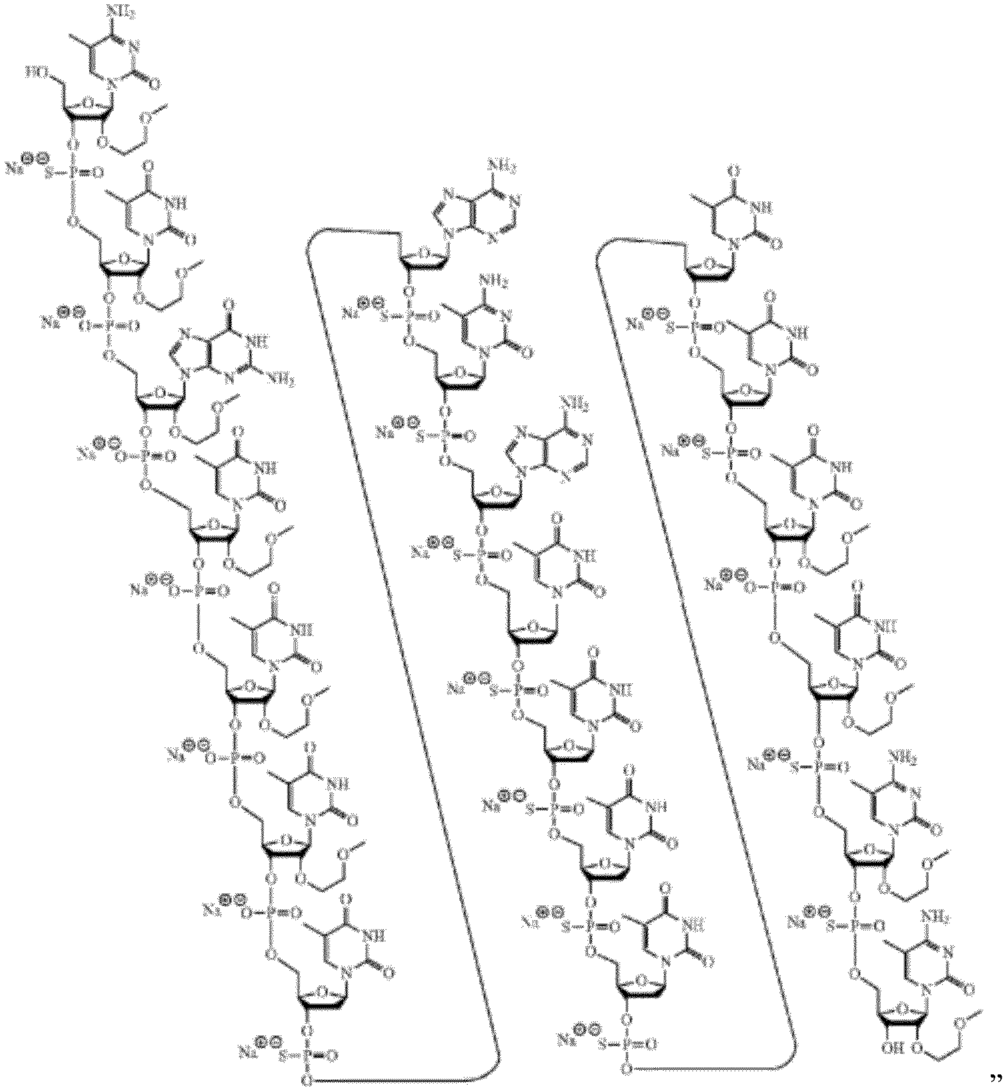
"
To:

--
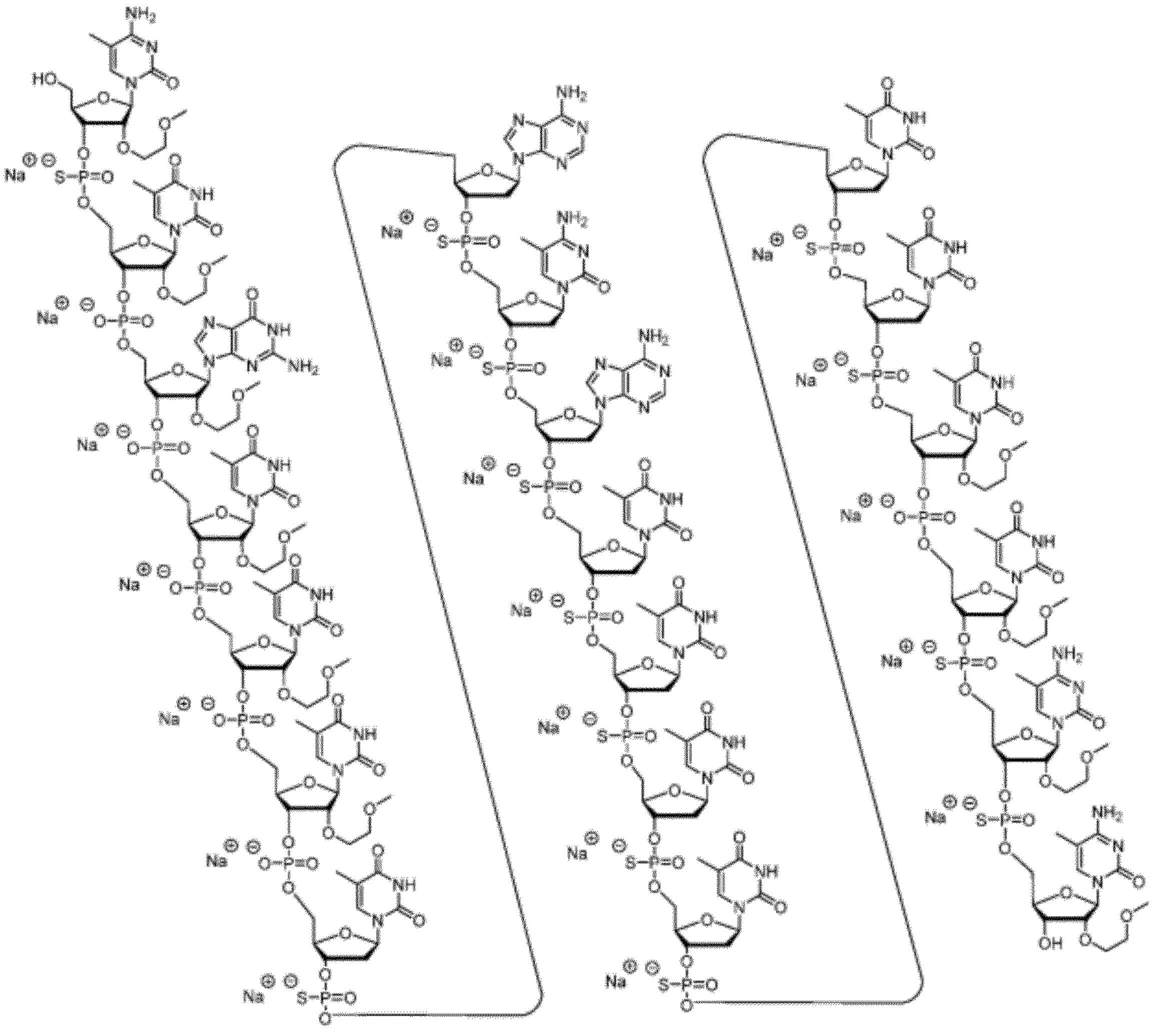
--.
Columns 43-44, change:

“ 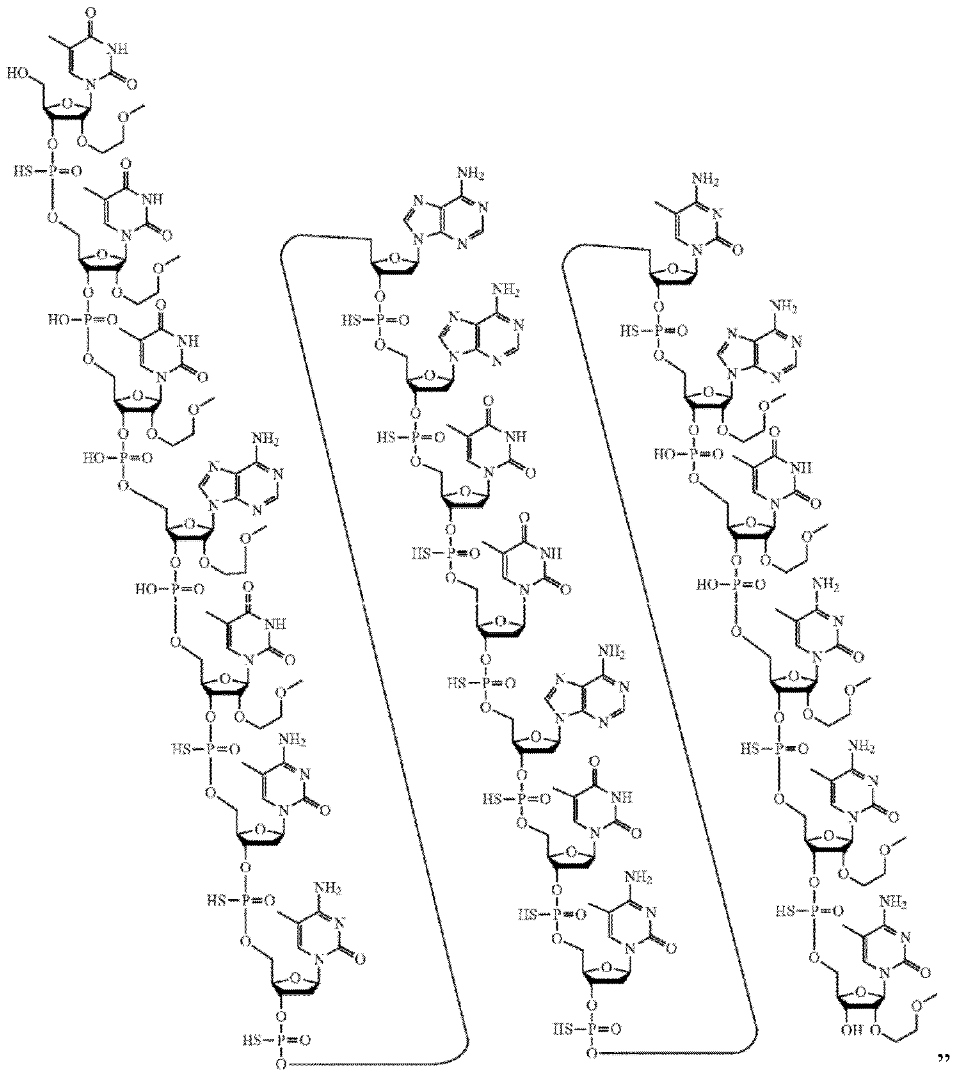 ”
To:

--
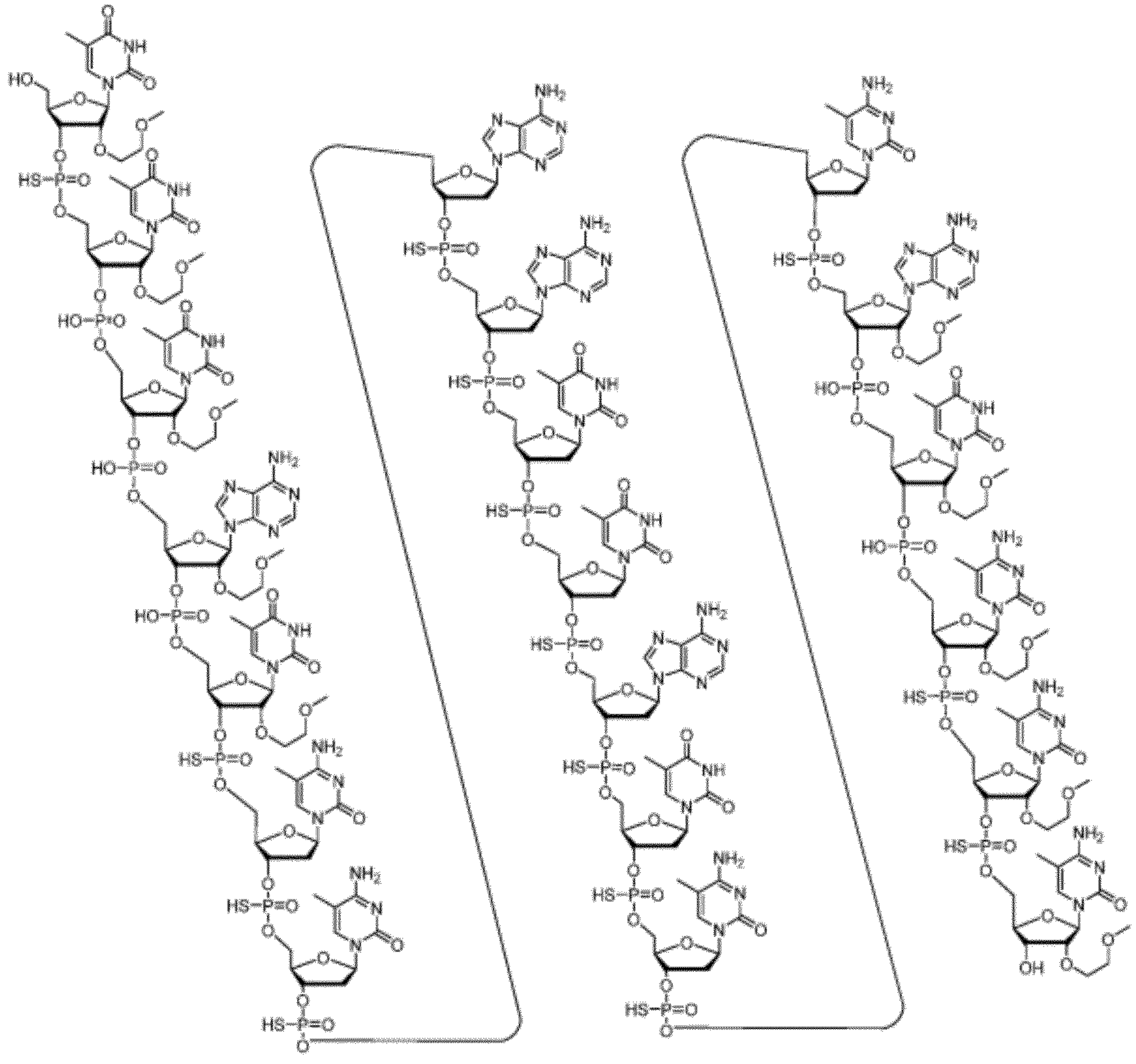
--.
Columns 45-46, change:

"
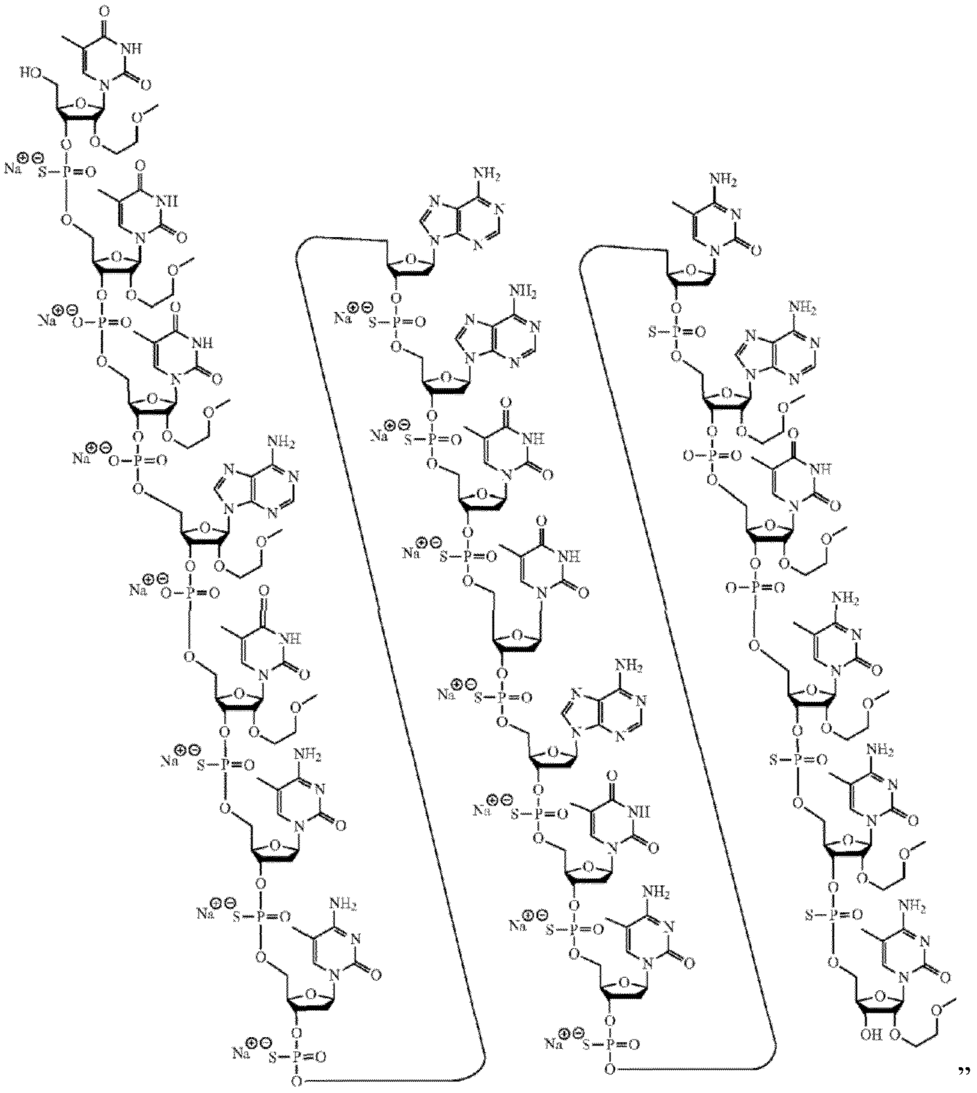
"
To:

--
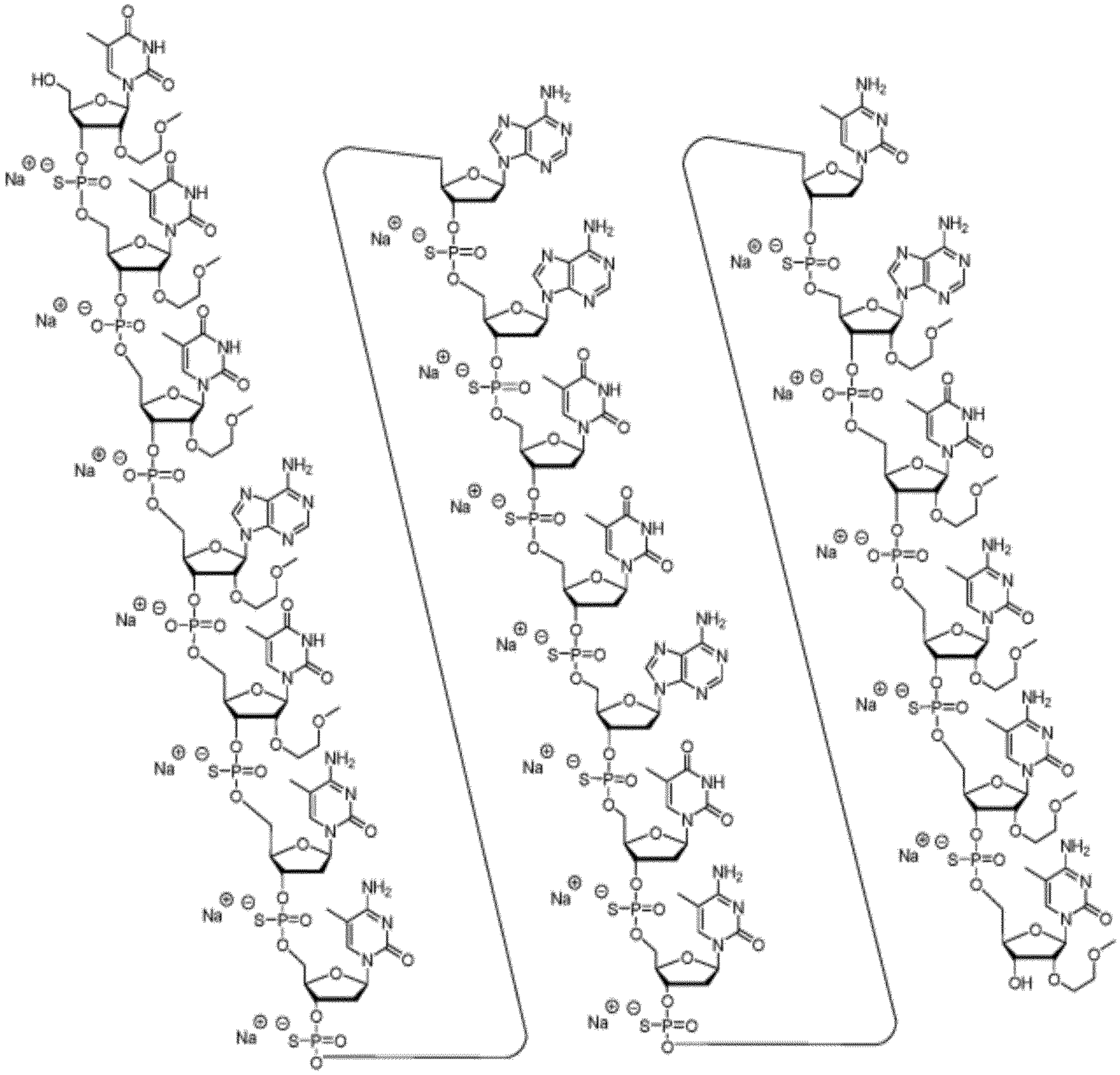
--.
Columns 47-48, change:

“ 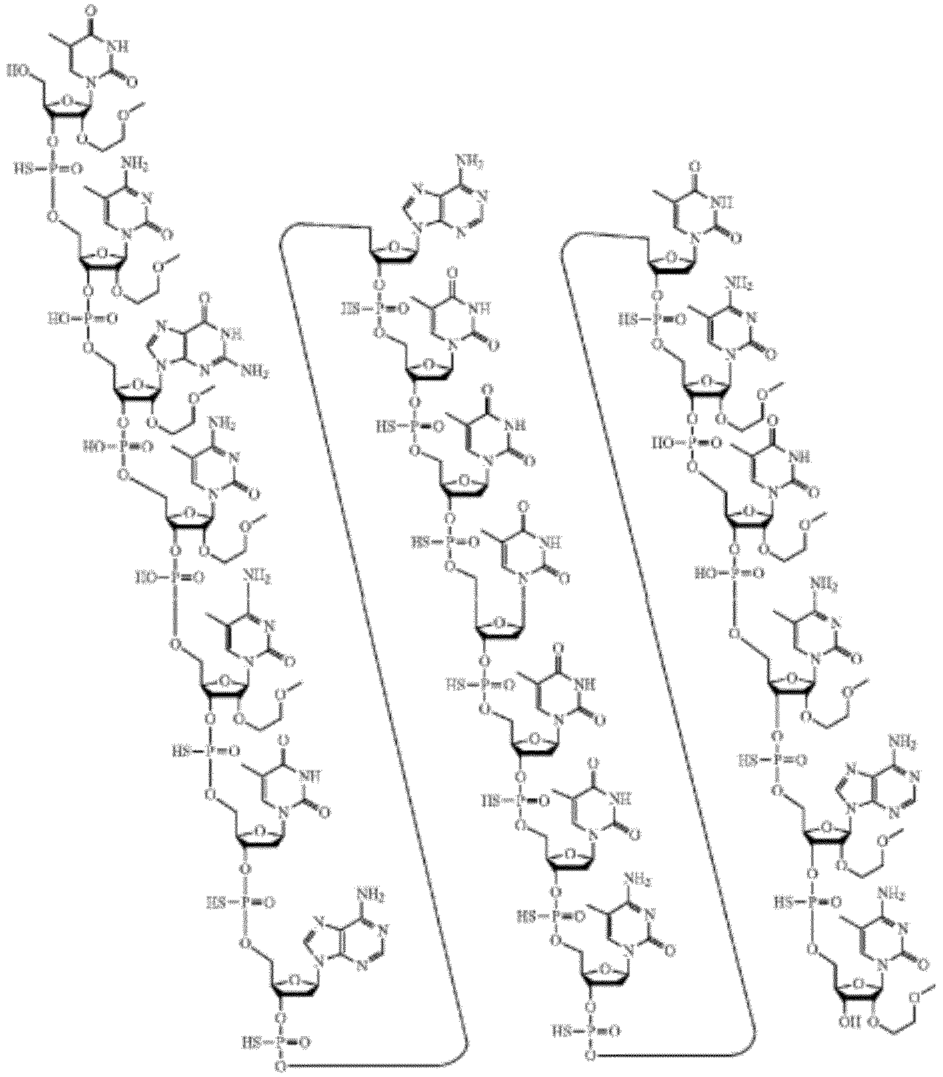 ”
To:

-- 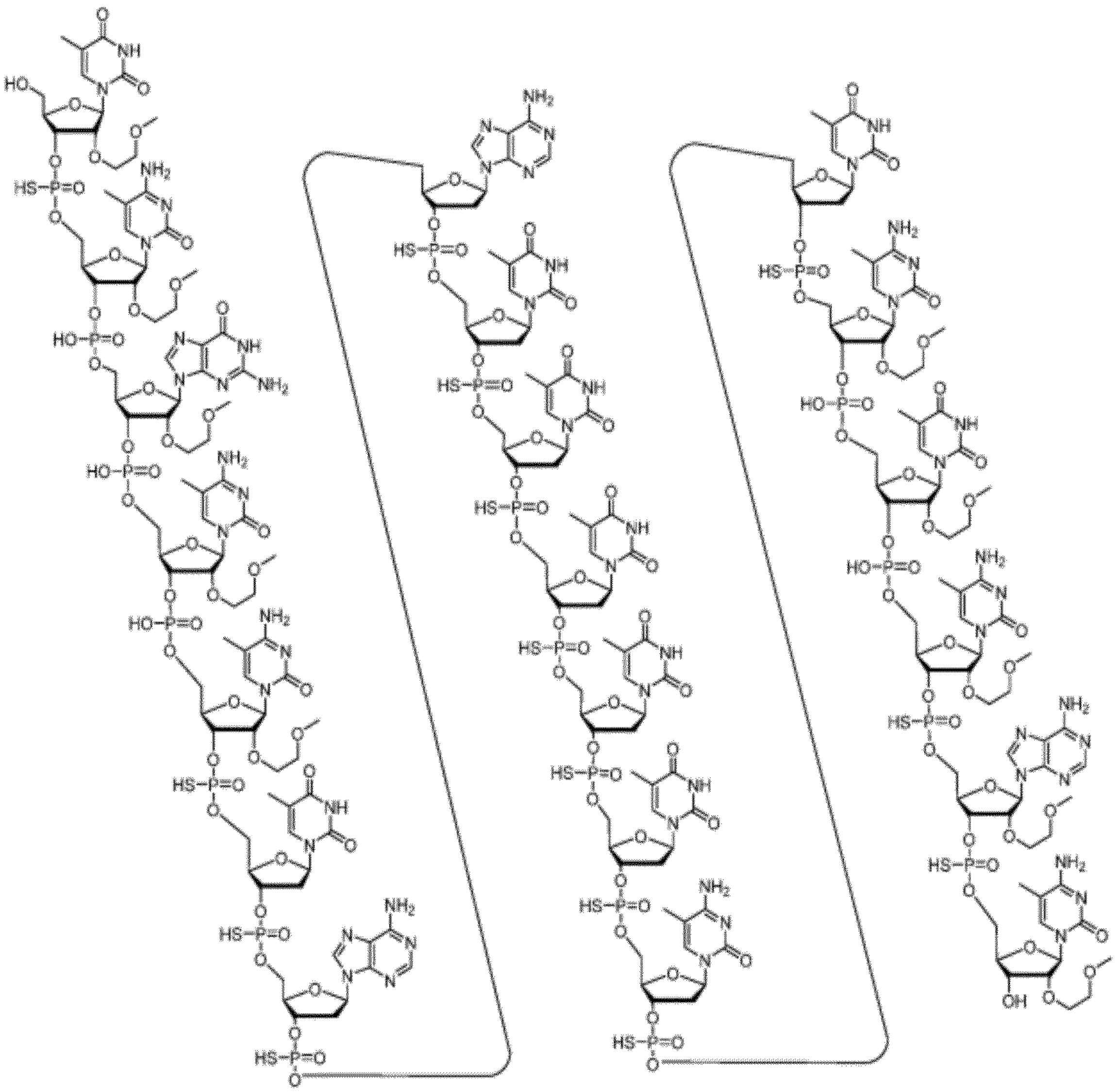 --.
Columns 49-50, change:

"
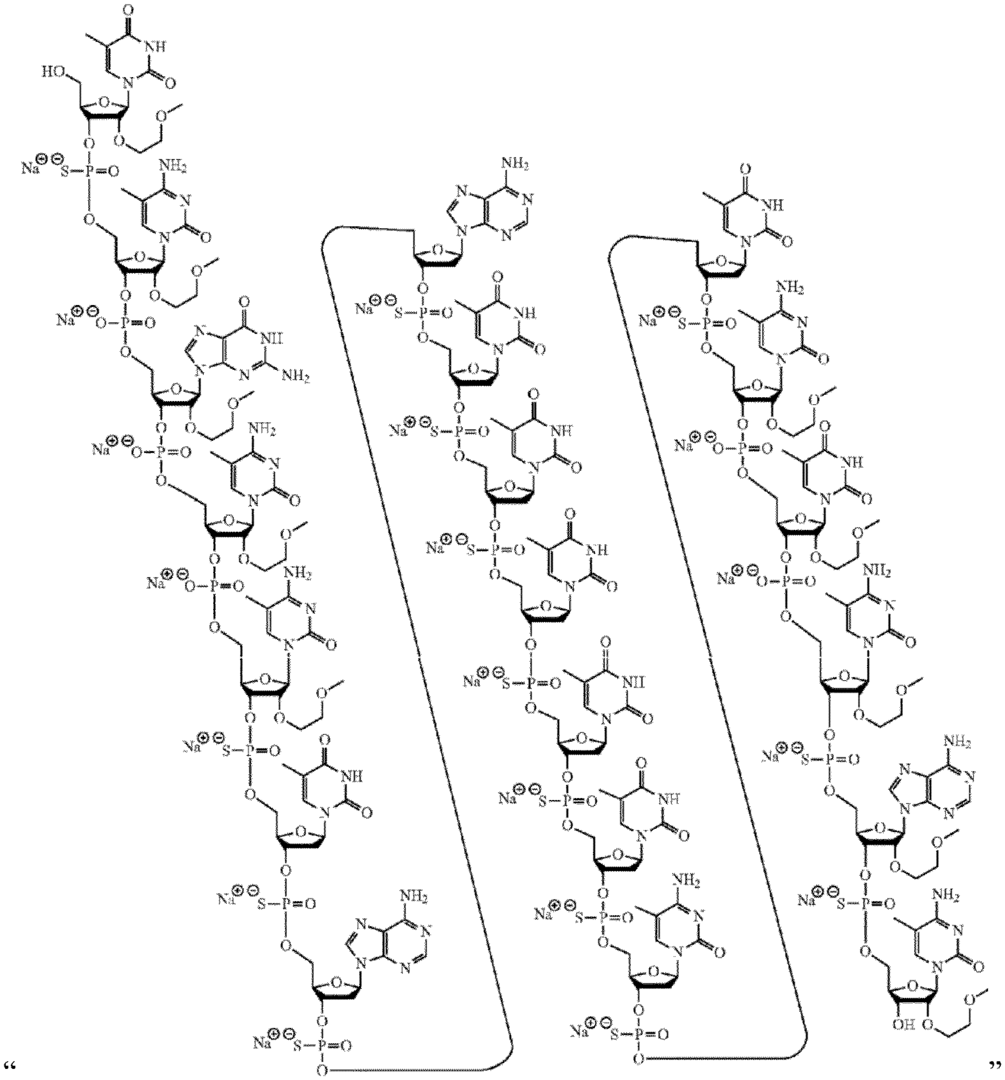
"
To:

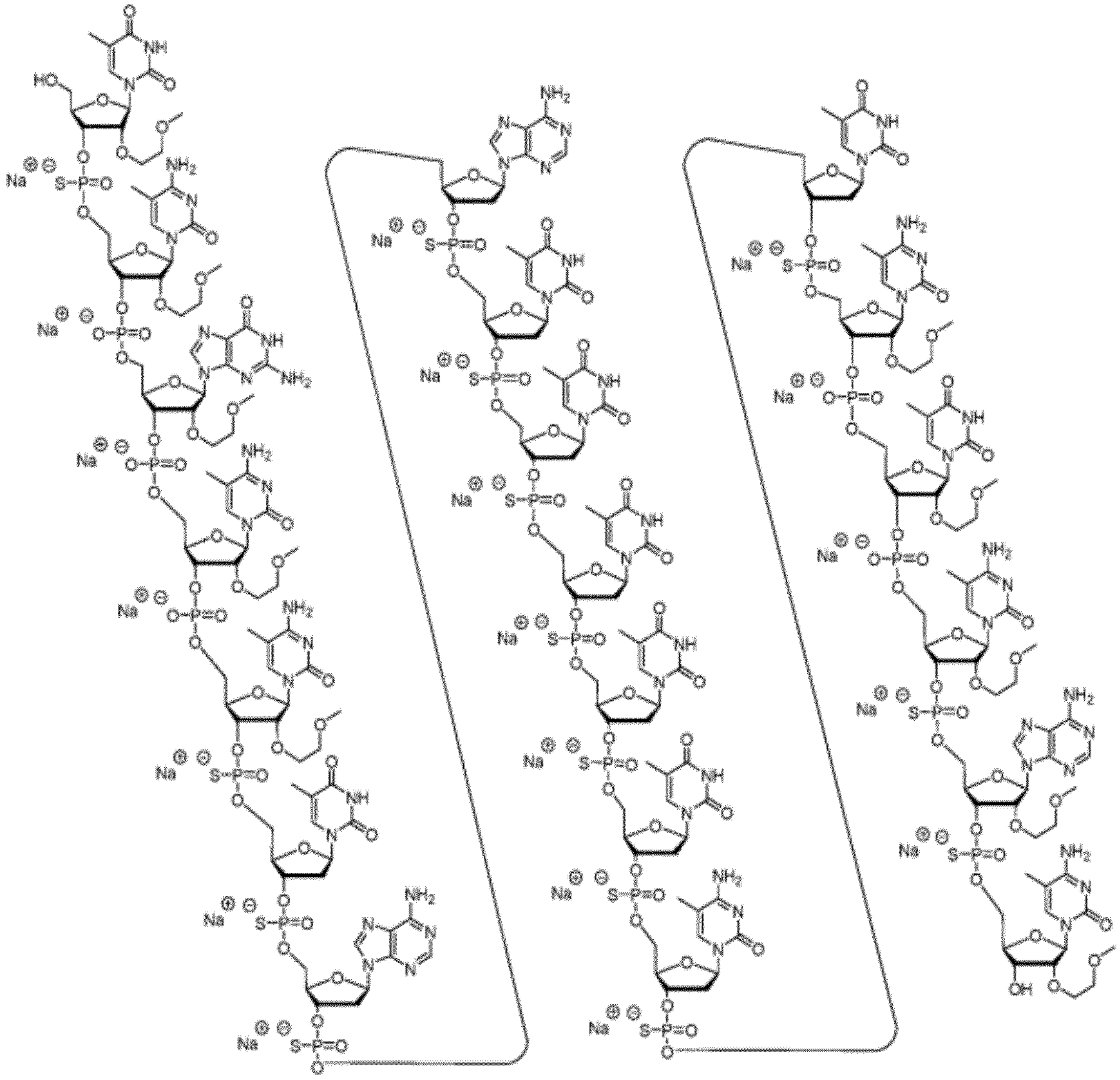
-- --.
Columns 51-52, change:

“ 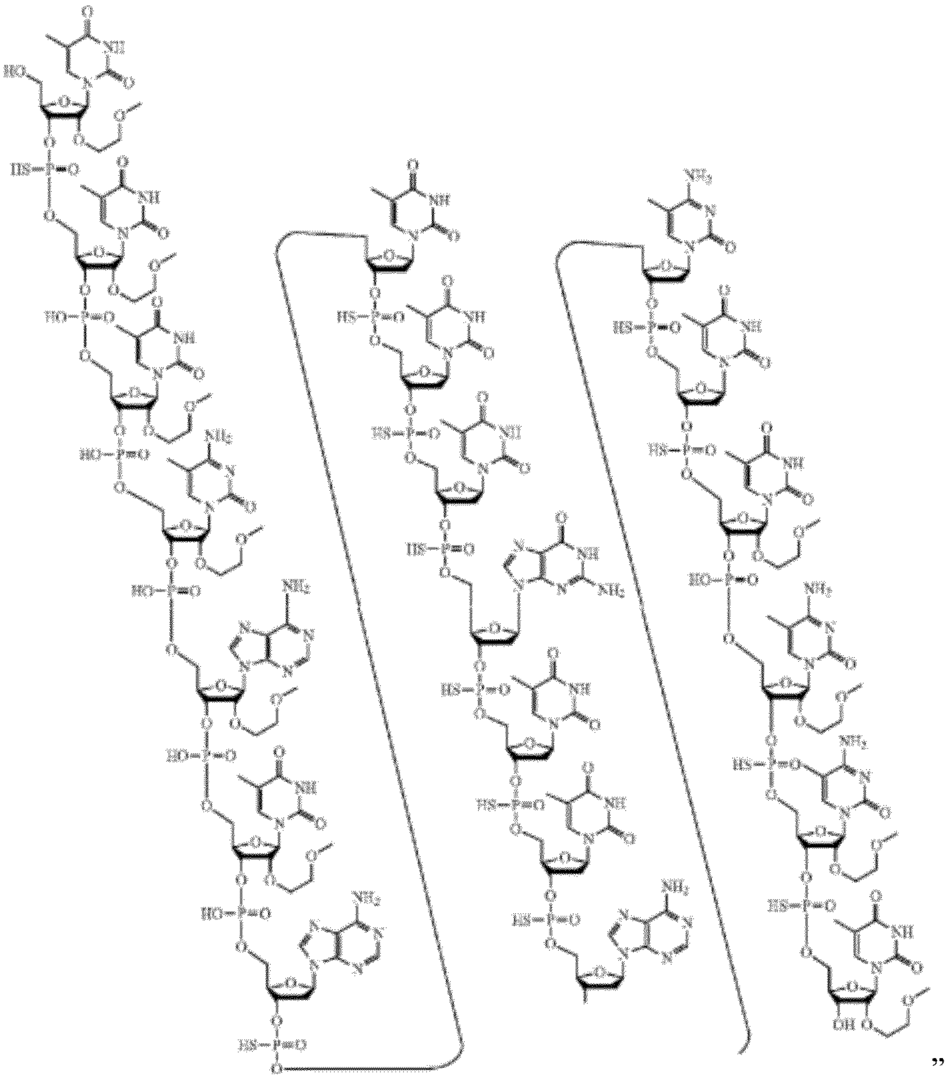 ”
To:

--
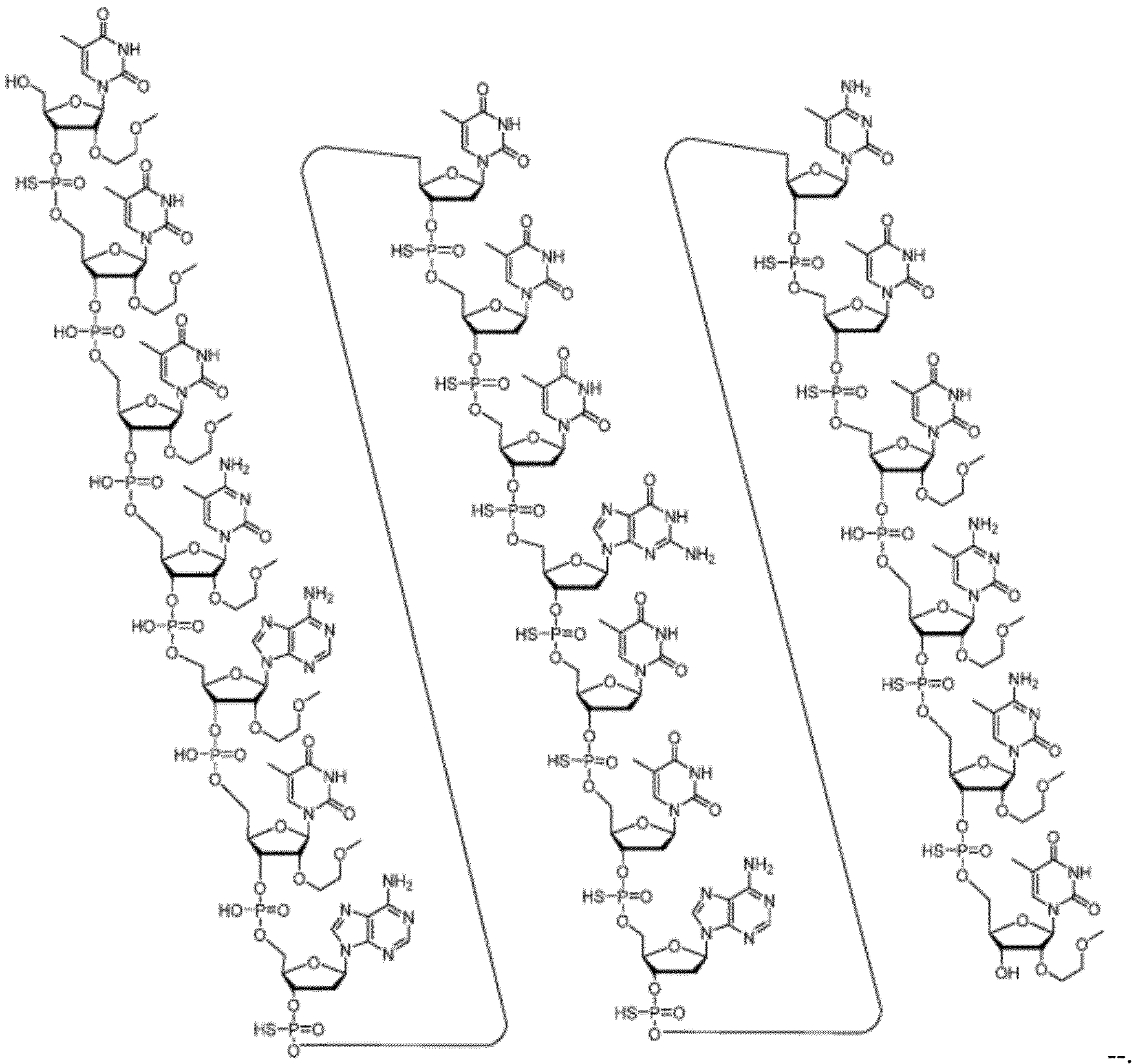
--.
Columns 53-54, change:

“ 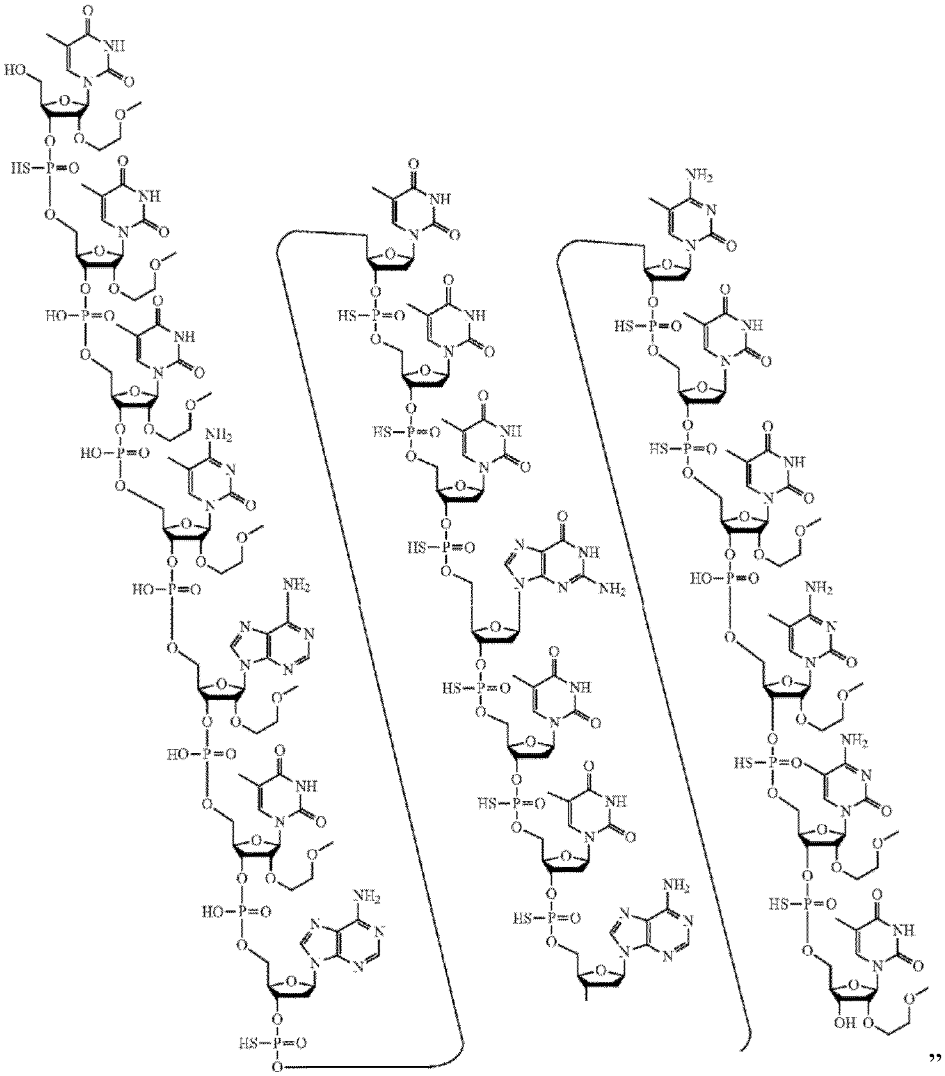 ”
To:

-- 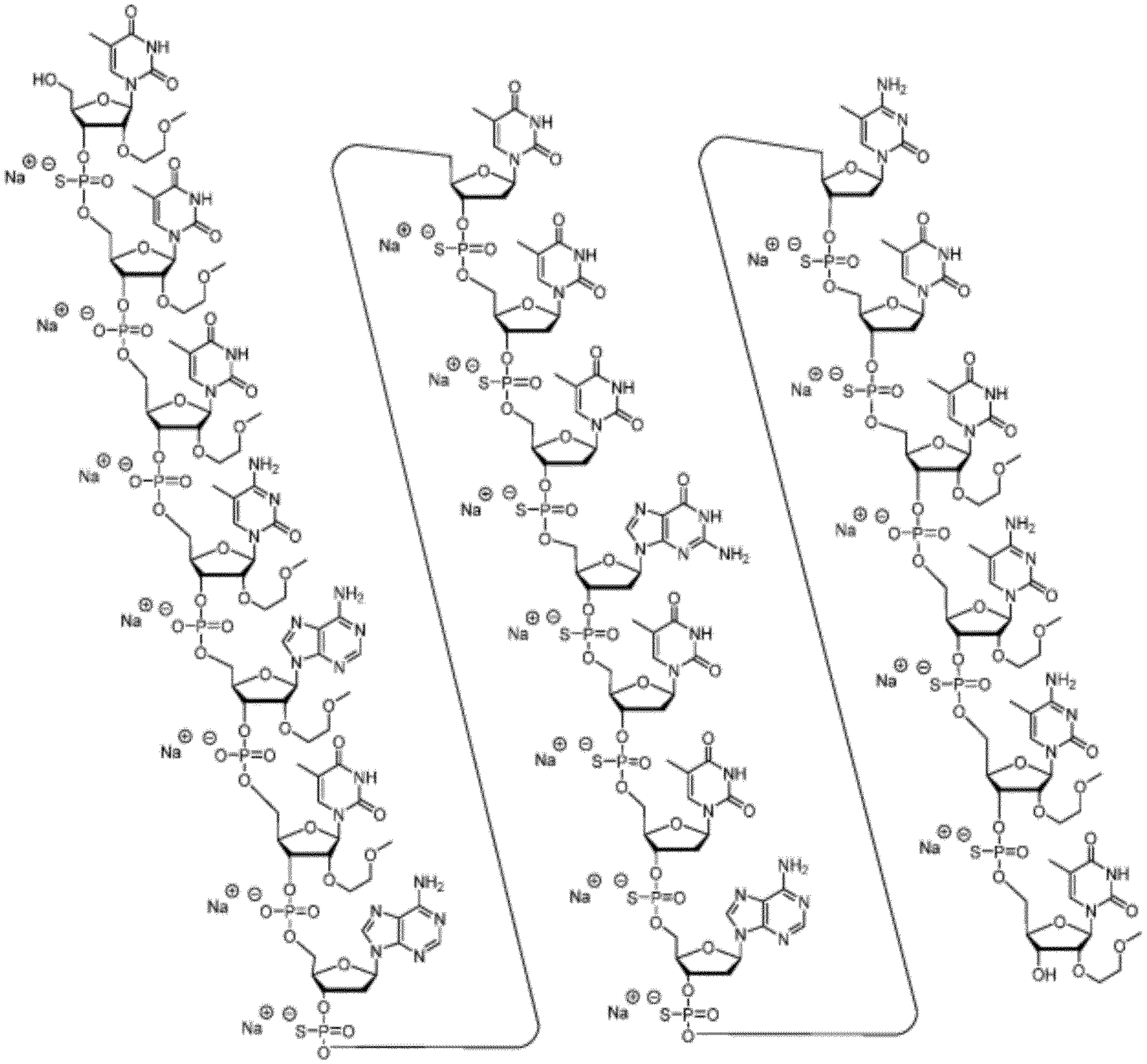 --.
Columns 55-56, change:

"
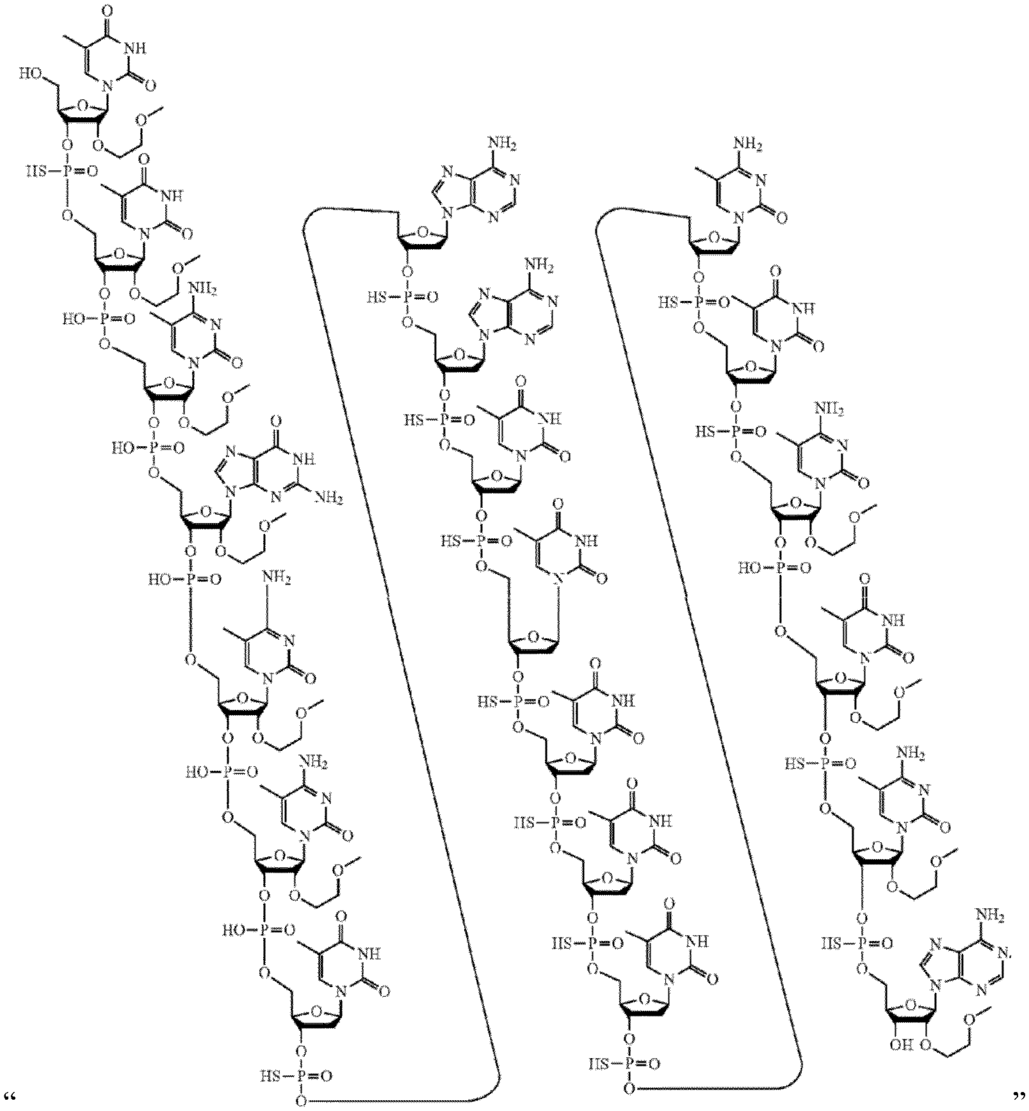
"
To:

-- 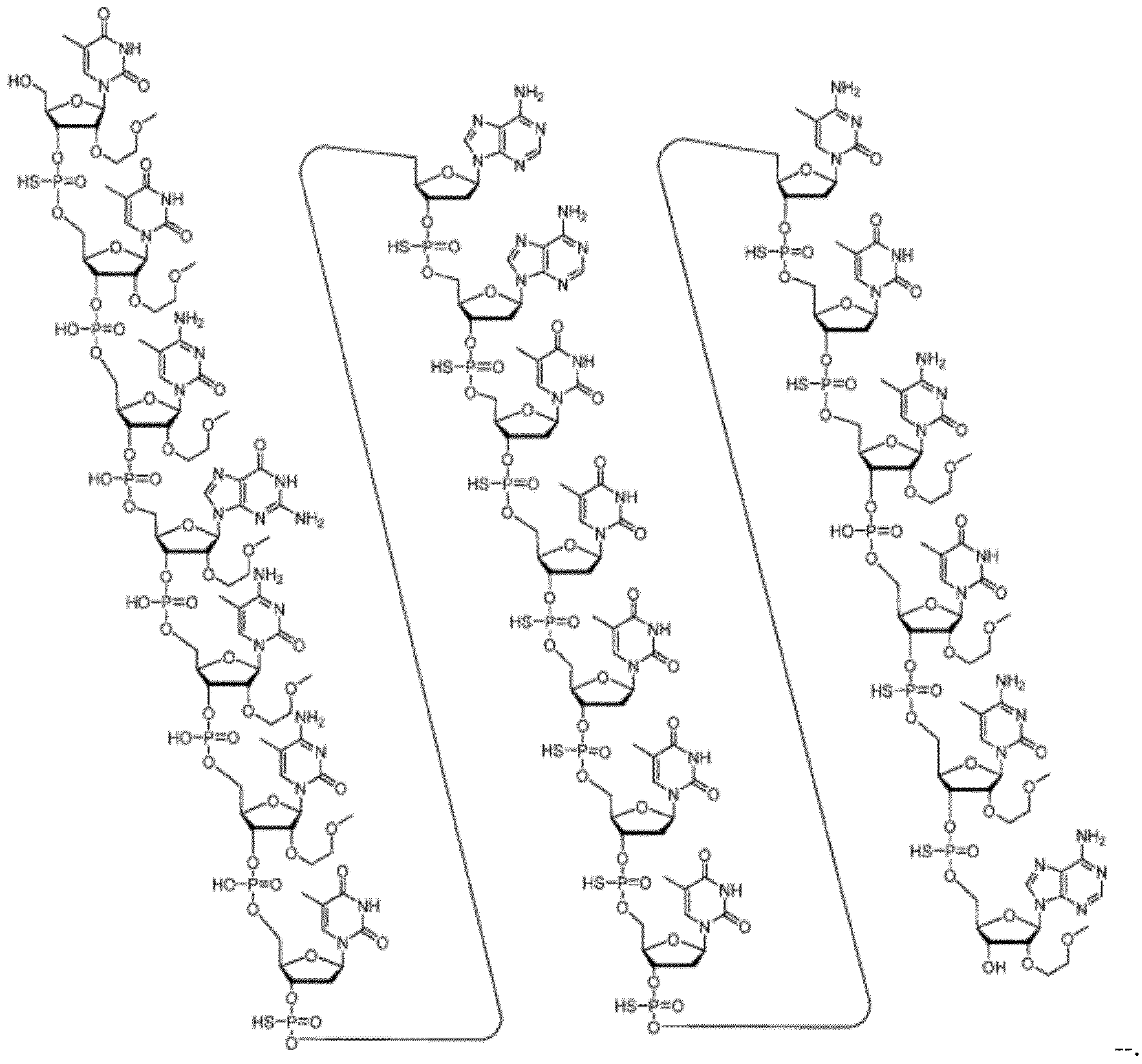 --.
Columns 57-58, change:

“ 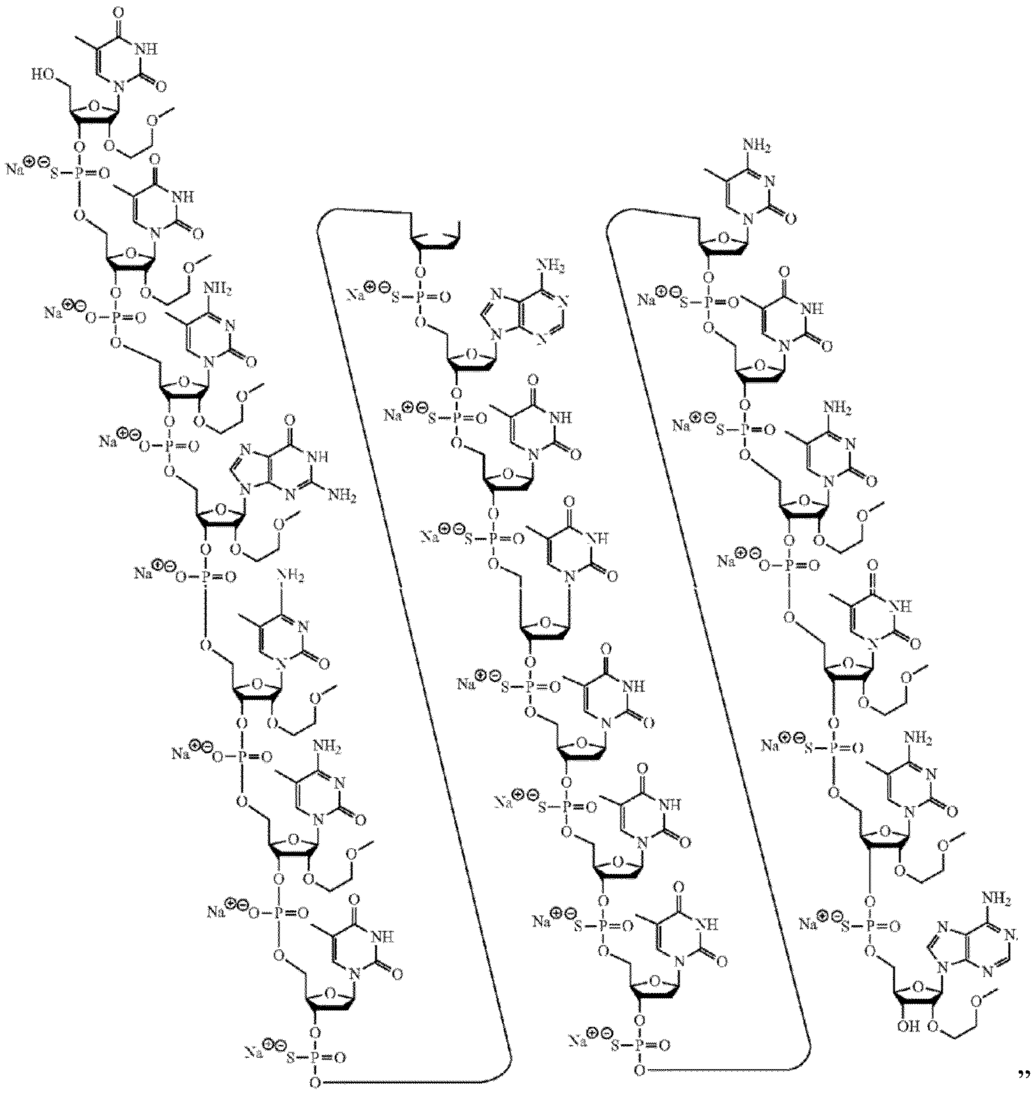 ”
To:

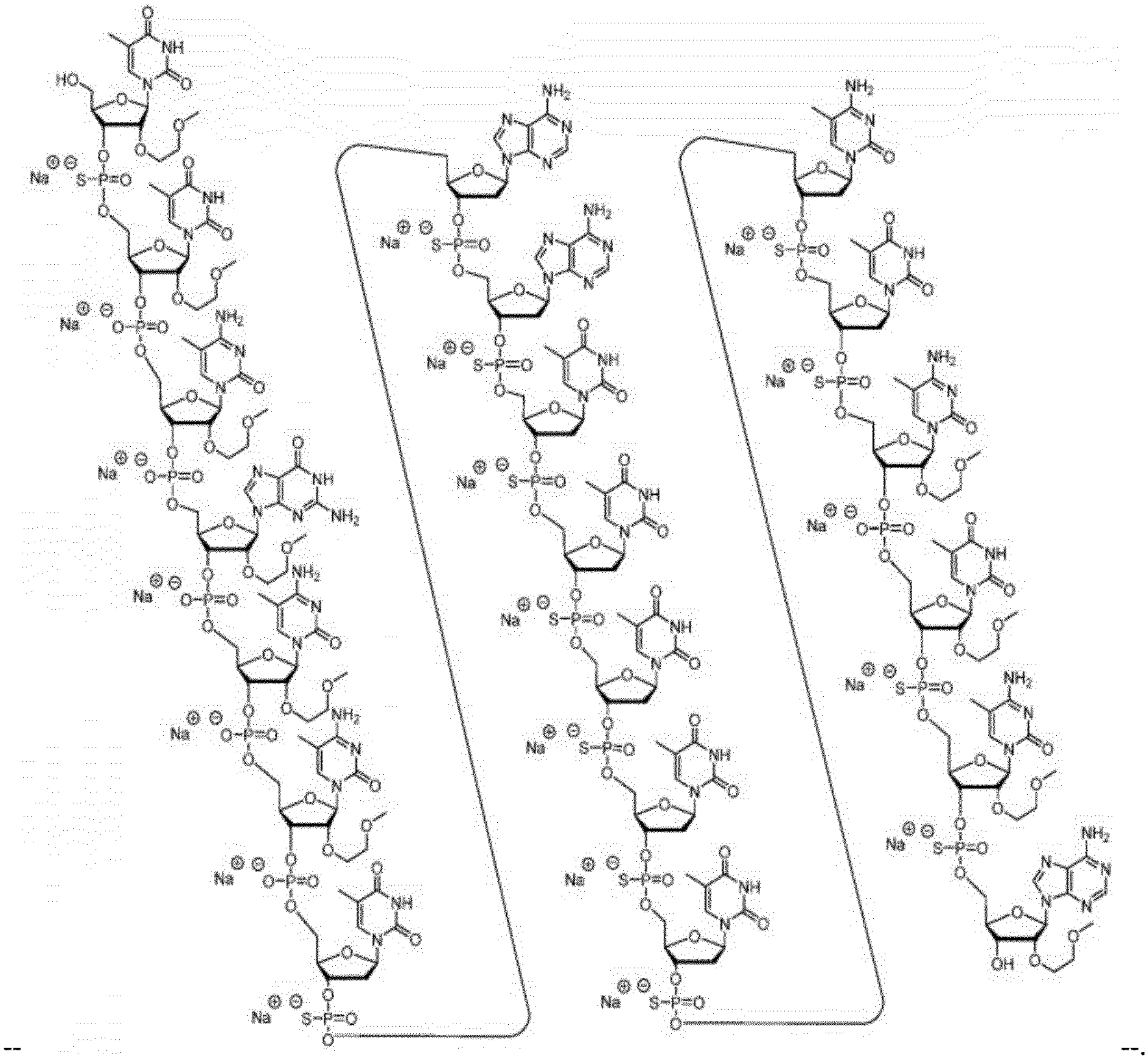
-- --.
Column 79, change:
TABLE 2
6-10-4 MOE gapmers with mixed PO/PS internucleoside linkages complementary to human IFNAR1
| Compound Number | Sequence (5' to 3') | SEQ ID NO 1 Start Site | SEQ ID NO 1 Stop Site | SEQ ID NO 2 Start Site | SEQ ID NO Stop Site | SEQ ID NO |
|---|---|---|---|---|---|---|
| 1489477 | CTTTTTCTGCTCTTATACGC | 20104 | 20123 | 453 | 472 | 11 |
| 1489494 | CTGTTTTACATTTTTTTTCC | 20591 | 20610 | N/A | N/A | 12 |
| 1492082 | TTTCATATTTGTTACTTCCT | 29981 | 30000 | N/A | N/A | 13 |
| 1492131 | TTCGCCTAATTTTTCTCTCA | 22456 | 22475 | N/A | N/A | 14 |
" "
To:

TABLE 2

| 6-10-4 MOE gapmers with mixed PO/PS internucleoside linkages complementary to human IFNAR1 | | | | | | |
|---|---|---|---|---|---|---|
| **Compound Number** | **Sequence (5' to 3')** | **SEQ ID NO 1 Start Site** | **SEQ ID NO 1 Stop Site** | **SEQ ID NO 2 Start Site** | **SEQ ID NO 2 Stop Site** | **SEQ ID NO** |
| 1489477 | CTTTTTCTGCTCTTATACGC | 20104 | 20123 | 453 | 472 | 11 |
| 1489494 | CTGTTTTACATTTTTTTTCC | 20591 | 20610 | N/A | N/A | 12 |
| 1492082 | TTTCATATTTGTTACTTCCT | 29981 | 30000 | N/A | N/A | 13 |
| 1492131 | TTCGCCTAATTTTTCTCTCA | 22456 | 22475 | N/A | N/A | 14 |

-- --.

In the Claims

Columns 127-128, Claim 1, change:

"

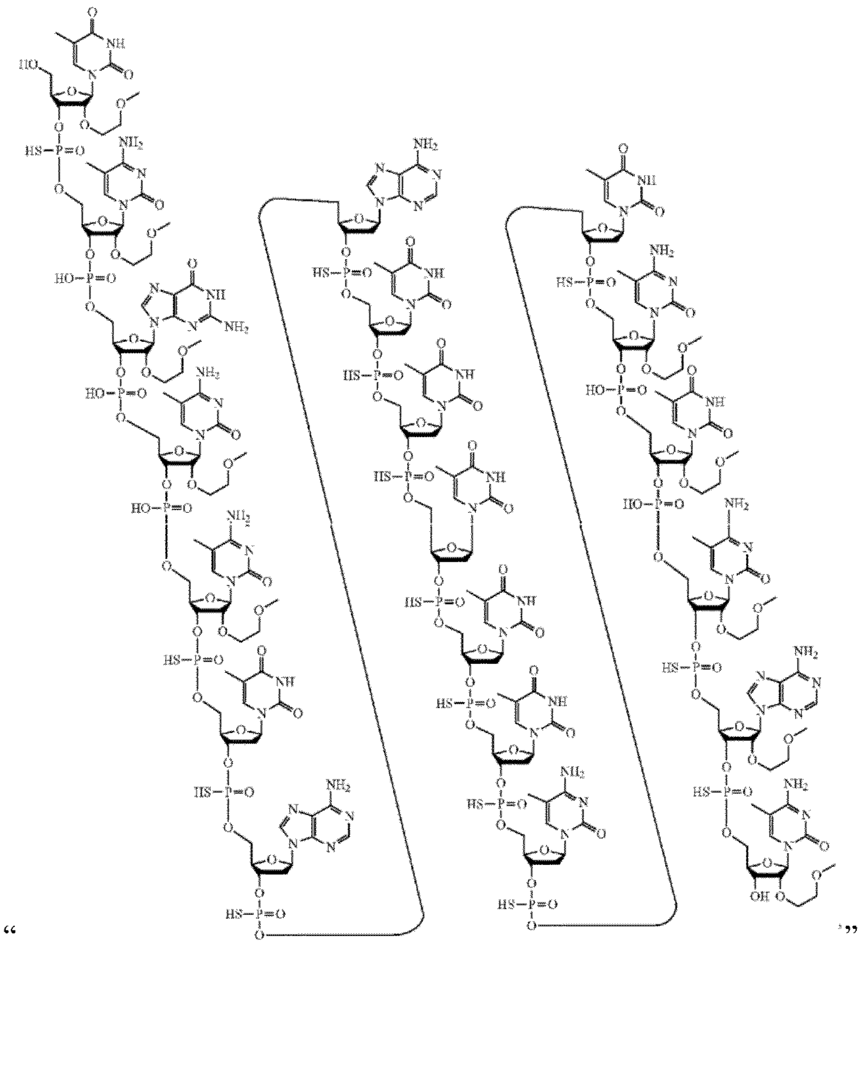

",

To:

-- 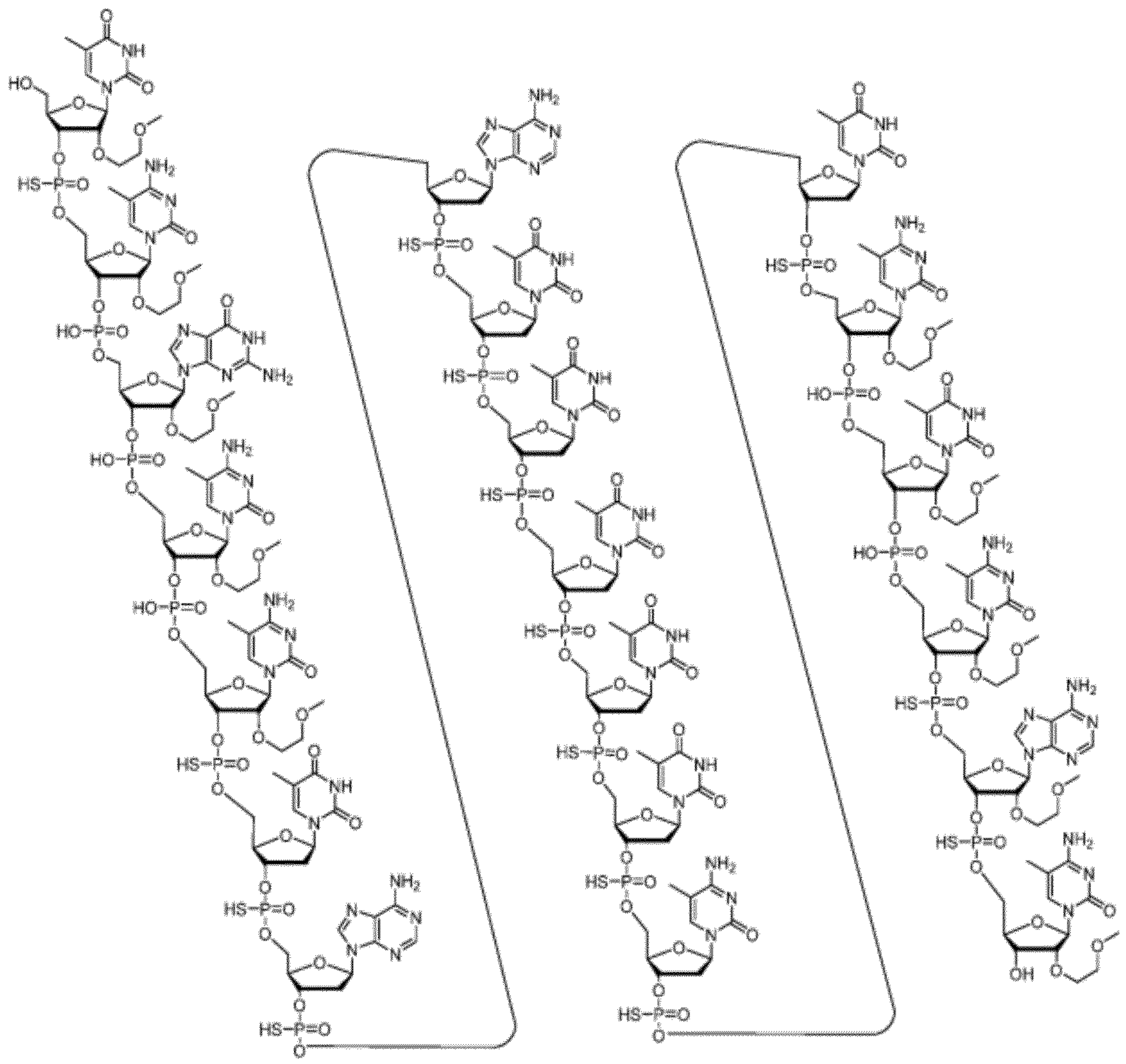 --.
Columns 129-130, Claim 3, change:

"
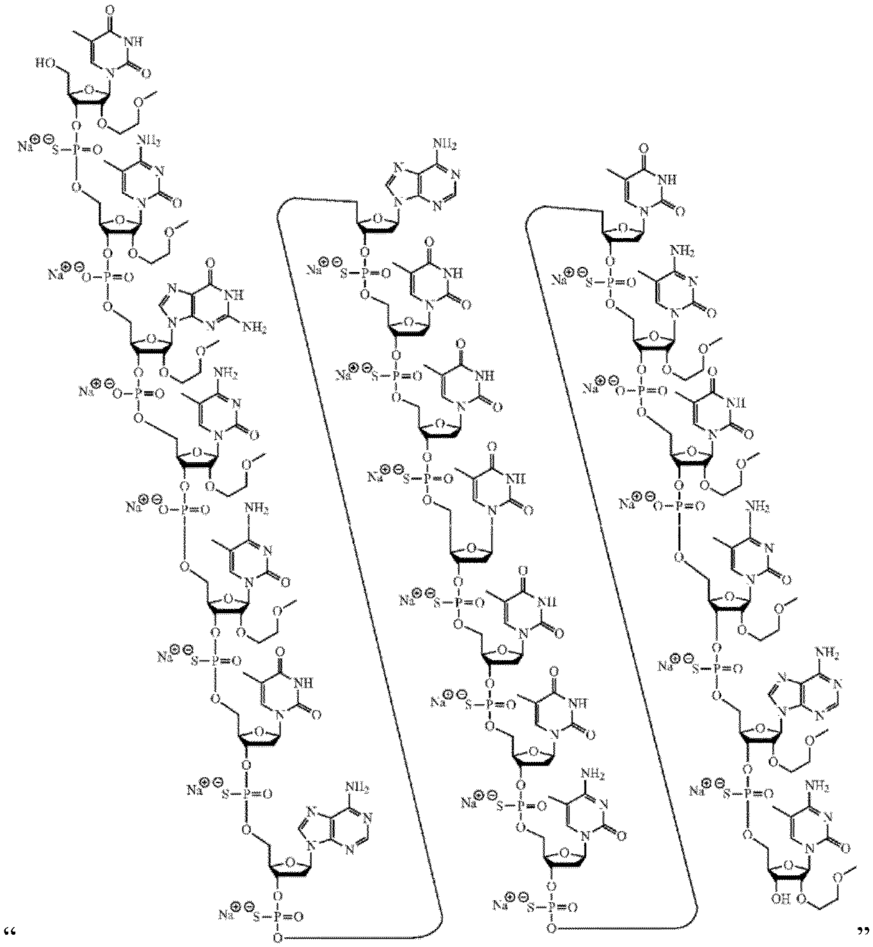
"
To:

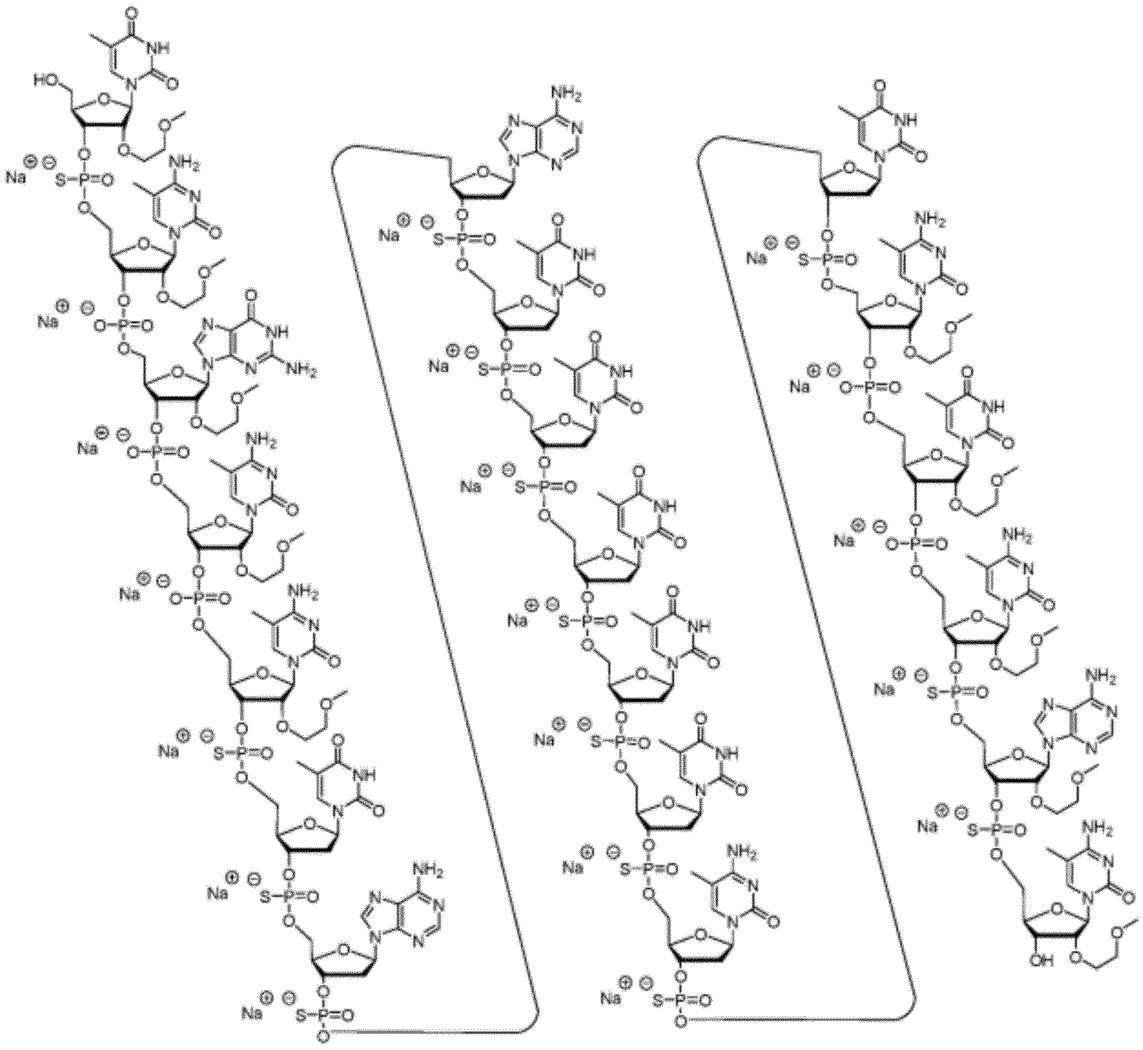
-- --.